United States Patent
Noda et al.

(10) Patent No.: US 10,570,269 B2
(45) Date of Patent: Feb. 25, 2020

(54) COMPOSITION CONTAINING MICROPARTICLES

(71) Applicant: TOKYO OHKA KOGYO CO., LTD., Kawasaki-shi (JP)

(72) Inventors: Kunihiro Noda, Kawasaki (JP); Hiroki Chisaka, Kawasaki (JP); Koichi Misumi, Kawasaki (JP); Dai Shiota, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 95 days.

(21) Appl. No.: 15/746,348

(22) PCT Filed: Jul. 15, 2016

(86) PCT No.: PCT/JP2016/071051
§ 371 (c)(1),
(2) Date: Jan. 19, 2018

(87) PCT Pub. No.: WO2017/014203
PCT Pub. Date: Jan. 26, 2017

(65) Prior Publication Data
US 2018/0194930 A1    Jul. 12, 2018

(30) Foreign Application Priority Data

Jul. 23, 2015 (JP) .................................. 2015-146227

(51) Int. Cl.

| | |
|---|---|
| *C08K 5/3445* | (2006.01) |
| *C07D 233/58* | (2006.01) |
| *C07D 233/60* | (2006.01) |
| *C08L 101/00* | (2006.01) |
| *C08K 3/013* | (2018.01) |
| *C08F 2/48* | (2006.01) |
| *C08F 220/06* | (2006.01) |
| *C08F 220/18* | (2006.01) |
| *C08F 2/44* | (2006.01) |
| *C08F 2/46* | (2006.01) |
| *C08J 3/24* | (2006.01) |

(52) U.S. Cl.
CPC .......... *C08K 5/3445* (2013.01); *C07D 233/58* (2013.01); *C07D 233/60* (2013.01); *C08F 2/44* (2013.01); *C08F 2/46* (2013.01); *C08F 2/48* (2013.01); *C08F 220/06* (2013.01); *C08F 220/18* (2013.01); *C08J 3/24* (2013.01); *C08K 3/013* (2018.01); *C08L 101/00* (2013.01); *C08J 2300/24* (2013.01); *C08J 2363/00* (2013.01); *C08K 2201/003* (2013.01)

(58) Field of Classification Search
None
See application file for complete search history.

(56) References Cited

U.S. PATENT DOCUMENTS

| | | | | | |
|---|---|---|---|---|---|
| 3,356,645 | A | * | 12/1967 | Warren | .................... C07J 75/00 552/576 |
| 3,553,166 | A | * | 1/1971 | Anderson et al. | ... C08G 59/306 528/117 |
| 3,746,686 | A | * | 7/1973 | Marshall et al. | .. C08G 59/5093 528/114 |
| 3,839,573 | A | * | 10/1974 | Buchel et al. | ........ C07D 231/12 514/396 |
| 7,473,310 | B2 | * | 1/2009 | Carlini | .................. C09B 63/005 106/496 |
| 9,725,567 | B2 | * | 8/2017 | Wang | ..................... C08G 59/38 |
| 2006/0207720 | A1 | * | 9/2006 | Yoshizawa | ......... C08G 59/3218 156/325 |
| 2010/0255313 | A1 | * | 10/2010 | Ito | ...................... C08G 59/4021 428/414 |

FOREIGN PATENT DOCUMENTS

| | | |
|---|---|---|
| JP | H08-003529 | 1/1996 |
| JP | H09-040849 | 2/1997 |
| JP | 2005-213405 | 8/2005 |
| JP | 2006-291167 | 10/2006 |
| JP | 2007-322546 | 12/2007 |
| JP | 2011-157491 | 8/2011 |
| JP | 2012-041386 | 3/2012 |

* cited by examiner

*Primary Examiner* — Tae H Yoon
(74) *Attorney, Agent, or Firm* — Knobbe, Martens, Olson & Bear LLP

(57) ABSTRACT

A composition which contains microparticles and does not undergo the long-term process of aggregation of the microparticles during storage of the composition. An imidazole compound having a specific structure is added to a composition containing microparticles having a volume average particle diameter of 3000 nm or less. The composition may contain a base material component. The base material component may be a heat-curable or photocurable base material component. The microparticles may be inorganic particles and/or organic particles.

7 Claims, No Drawings

COMPOSITION CONTAINING MICROPARTICLES

This application is the U.S. National Phase under 35 U.S.C. § 371 of International Application PCT/JP2016/071051, filed Jul. 15, 2016, designating the U.S., and published in Japanese as WO 2017/014203 on Jan. 26, 2017 which claims priority to Japanese Patent Application No. 2015-146227, filed Jul. 23, 2015, the entire content of which is incorporated herein by reference.

TECHNICAL FIELD

The present invention relates to a composition that contains an imidazole compound having a specific structure and contains a fine particle.

BACKGROUND ART

Conventionally, compositions containing various fine particles dispersed therein are used in various applications. Typical examples include compositions containing black fine particles like carbon black and compositions containing white fine particles like titanium oxide or barium sulfate.

For example, liquid compositions containing carbon black dispersed therein are used not only for printing and painting applications, but also as a material for forming a light shielding member such as a black matrix and a black column spacer in various display panels. Similarly, liquid compositions containing titanium oxide dispersed therein are used for forming a white solder resist film on the surface of a substrate on which a light-emitting device is to be mounted. Use of such a liquid composition containing titanium oxide may yield a highly reflective solder resist film that is capable of efficiently reflecting light emitted from a light-emitting device.

Typically, carbon black is often used after it is dispersed in a solvent such as an organic solvent with the use of a dispersant. As an example of a method of dispersing carbon black using a dispersant, a method of dispersing carbon black in an organic solvent such as alcohol, a glycol-based solvent, ketones, and an aprotic polar organic solvent by using a low-molecular compound such as an organic dye derivative and a triazine derivative as a dispersant is known (Patent Document 1). By this method described in Patent Document 1, a carbon black dispersion containing an organic solvent as a dispersion medium is prepared.

As a liquid composition containing titanium oxide for use in solder resist film formation, a curable composition is known that contains a resin containing a carboxy group and no aromatic ring, a photopolymerization initiator, an epoxy compound, a rutile-type titanium oxide, and a diluent (Patent Document 2).

Patent Document 1: Japanese Unexamined Patent Application, Publication No. 2005-213405
Patent Document 2: Japanese Unexamined Patent Application, Publication No. 2007-322546

DISCLOSURE OF THE INVENTION

Problems to be Solved by the Invention

The compositions described in Patent Documents 1 and 2 have problems that fine particles of carbon black, titanium oxide, and the like are hard to disperse at the time of preparation of the compositions and that fine particles of carbon black, titanium oxide, and the like tend to aggregate with time during storage of the compositions.

The present invention has been devised based on the above circumstances, and an object of the present invention is to provide a composition that contains a fine particle and in which aggregation of the fine particle is inhibited from proceeding with time during storage.

Means for Solving the Problems

The inventors of the present invention have solved the above problems by blending an (A) imidazole compound having a specific structure into a composition that contains a (B) fine particle having a volume average particle diameter of 3000 nm or less. Thus, the present invention has now been completed.

A first aspect of the present invention provides a composition comprising an (A) imidazole compound represented by the following formula (1) and a (B) fine particle, the (B) fine particle having a volume average particle diameter of 3000 nm or less.

[Chem. 1]

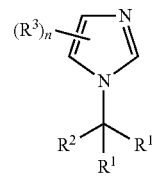

(1)

(In the formula (1), $R^1$ represents each independently a hydrogen atom or a monovalent organic group; $R^2$ represents an optionally substituted aromatic group; $R^3$ represents each independently a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n is an integer of 0 to 3. One $R^1$ is optionally be bonded to the other $R^1$ or $R^2$ to form a ring structure.)

A second aspect of the present invention provides a cured article derived from the composition as described in the first aspect.

A third aspect of the present invention provides a method for producing a cured article, comprising shaping the composition as described in the first aspect containing a (C) thermosetting or photocurable base material into a predetermined shape and then subjecting the shaped composition to heating or light exposure to form a cured article.

Effects of the Invention

According to the present invention, a composition that contains a fine particle and in which aggregation of the fine particle is inhibited from proceeding with time during storage may be provided.

PREFERRED MODE FOR CARRYING OUT THE INVENTION

<<Composition>>

A composition according to the present invention contains an (A) imidazole compound and a (B) fine particle. The (A) imidazole compound has a predetermined structure described below. The (B) fine particle has a volume average particle diameter of 3000 nm or less. In the composition according to the present invention, the (A) imidazole compound acts to make the (B) fine particle stably dispersed in the composition and inhibit aggregation of the (B) fine particle from proceeding during storage of the composition. Next, essential or optional components contained in the composition according to the present invention are described.

<(A) Imidazole Compound>

The composition according to the present invention essentially contains the (A) imidazole compound, which is a compound represented by the following formula (1). The composition contains the (B) fine particle, which is described below. The (B) fine particle has a small particle diameter and therefore tends to aggregate in the composition. However, since the composition contains the (A) imidazole compound, the (B) fine particle is stably dispersed in the composition.

[Chem. 2]

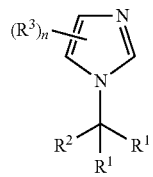

(1)

(In the formula (1), $R^1$ represents each independently a hydrogen atom or a monovalent organic group; $R^2$ represents an optionally substituted aromatic group; $R^3$ represents each independently a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n is an integer of 0 to 3. One $R^1$ may be bonded to the other $R^1$ or $R^2$ to form a ring structure.)

In the case in which the composition contains a (C) thermosetting or photocurable base material described below, particularly a thermosetting base material, the component (A) promotes the curing of the (C) base material. Particularly in the case in which the composition contains the (C) thermosetting base material, thermosetting of the composition tends to proceed at low temperature.

In the formula (1), $R^1$ represents a hydrogen atom or a monovalent organic group. The monovalent organic group is not particularly limited and may be, for example, an optionally substituted alkyl group or an optionally substituted aromatic group. In the case in which $R^1$ represents an alkyl group, the alkyl group may contain an ester bond or the like in the chain.

For example, the alkyl group may be the same as $R^4$ in a formula (1a) described below. The number of carbon atoms in the alkyl group is preferably 1 to 40, more preferably 1 to 30, particularly preferably 1 to 20, most preferably 1 to 10. A substituent that the alkyl group may contain may be the same as a substituent that an alkylene group as $R^5$ in the formula (1a) described below may contain, for example.

The optionally substituted aromatic group is the same as $R^2$ in the formula (1a) described below, preferably an aryl group, more preferably a phenyl group. The optionally substituted aromatic group as $R^1$ may be the same or different from $R^2$. In the formula (1), it is preferable that one $R^1$ be a hydrogen atom, more preferably one $R^1$ be a hydrogen atom and the other $R^1$ be an optionally substituted alkyl group or an optionally substituted aromatic group. In the formula (1), one $R^1$ may be bonded to the other $R^1$ or $R^2$ to form a ring structure. For example, in the case in which at least one $R^1$ is an optionally substituted alkyl group, one $R^1$ may be bonded to the other $R^1$ or $R^2$ to form a ring structure.

The (A) imidazole compound may be a compound represented by the following formula (1a).

[Chem. 3]

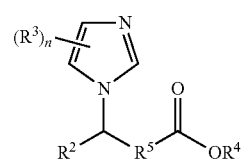

(1a)

(In the formula (1a), $R^4$ is a hydrogen atom or an alkyl group; $R^2$ is an optionally substituted aromatic group; $R^5$ is an optionally substituted alkylene group; $R^3$ is a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n is an integer of 0 to 3. $R^5$ may be bonded to $R^2$ to form a ring structure.)

In the formula (1a), $R^4$ is a hydrogen atom or an alkyl group. In the case in which $R^4$ is an alkyl group, the alkyl group may be either a linear alkyl group or a branched alkyl group. The number of carbon atoms of the alkyl group is not particularly limited, but is preferably 1 to 20, more preferably 1 to 10, particularly preferably 1 to 5.

Specific examples of the alkyl group suitable as $R^4$ include a methyl group, an ethyl group, an n-propyl group, an isopropyl group, an n-butyl group, an isobutyl group, an sec-butyl group, a tert-butyl group, an n-pentyl group, an isopentyl group, a tert-pentyl group, an n-hexyl group, an n-heptyl group, an n-octyl group, a 2-ethyl-n-hexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group.

In the formula (1a), $R^2$ is an optionally substituted aromatic group. The optionally substituted aromatic group may be either an optionally substituted aromatic hydrocarbon group or an optionally substituted aromatic heterocyclic group.

The type of the aromatic hydrocarbon group is not particularly limited as long as the object of the present invention is not impaired. The aromatic hydrocarbon group may be a monocyclic aromatic group, may be formed by fusion of two or more aromatic hydrocarbon groups, or may be formed by bonding of two or more aromatic hydrocarbon groups through a single bond. The aromatic hydrocarbon group is preferably a phenyl group, a naphthyl group, a biphenylyl group, an anthryl group, or a phenanthrenyl group.

The type of the aromatic heterocyclic group is not particularly limited as long as the object of the present invention is not impaired. The aromatic heterocyclic group may be either a monocyclic group or a polycyclic group. The aromatic heterocyclic group is preferably a pyridyl group, a furyl group, a thienyl group, an imidazolyl group, a pyrazolyl group, an oxazolyl group, a thiazolyl group, an isoxazolyl group, an isothiazolyl group, a benzoxazolyl group, a benzothiazolyl group, and a benzoimidazolyl group.

Examples of the substituent, which a phenyl group, a polycyclic aromatic hydrocarbon group, or an aromatic heterocyclic group may have, include a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, and an organic group. When the phenyl group, the polycyclic aromatic hydrocarbon group, or the aromatic heterocyclic group have a plurality of substituents, the plurality of substituents may be the same or different.

When the substituent, which the aromatic group has, is an organic group, examples of the organic group include an alkyl group, an alkenyl group, a cycloalkyl group, a cycloalkenyl group, an aryl group, an aralkyl group, or the like. This organic group may have a bond or a substituent, other than a hydrocarbon group such as a heteroatom, in the organic group. This organic group may be either linear, branched, cyclic, or a combination of these structures. This organic group is usually monovalent, but can be a divalent or higher polyvalent organic group when forming a cyclic structure.

When the aromatic group has a substituent on neighboring carbon atoms, two substituents bonded on neighboring carbon atoms may be bonded to form a cyclic structure. Examples of the cyclic structure include an aliphatic hydrocarbon ring, and an aliphatic ring having a heteroatom.

When the substituent, which the aromatic group has, is an organic group, the bond included in the organic group is not particularly limited, without impairing the effect of the present invention; and the organic group may include a bond containing a heteroatom such as an oxygen atom, a nitrogen atom, or a silicon atom. Specific examples of the bond containing a heteroatom include, an ether bond, a thioether bond, a carbonyl bond, a thiocarbonyl bond, a ester bond, a amide bond, a urethane bond, an imino bond (—N=C(—R)—, —C(=NR)—: R represents a hydrogen atom or an organic group), a carbonate bond, a sulfonyl bond, a sulfinyl bond, an azo bond, and the like.

From the viewpoint of heat resistance of the imidazole compound represented by the formula (1) or the formula (1a), the bond containing a heteroatom, which an organic group may have, is preferably an ether bond, a thioether bond, a carbonyl bond, a thiocarbonyl bond, an ester bond, an amide bond, an amino bond (—NR—: R represents a hydrogen atom or a monovalent organic group), an urethane bond, an imino bond (—N=C(—R)—, —C(=NR)—: R represents a hydrogen atom or a monovalent organic group), a carbonate bond, a sulfonyl bond, or a sulfinyl bond.

When the organic group is a substituent other than the hydrocarbon group, the type of the substituent other than the hydrocarbon group is not particularly limited as long as the object of the present invention is not impaired. Specific examples of the substituent other than the hydrocarbon group include a halogen atom, a hydroxy group, a mercapto group, a sulfide group, a cyano group, an isocyano group, a cyanato group, an isocyanato group, a thiocyanato group, an isothiocyanato group, an silyl group, an silanol group, an alkoxy group, an alkoxycarbonyl group, an amino group, a monoalkylamino group, a dialkylamino group, a monoarylamino group, a diarylamino group, a carbamoyl group, a thiocarbamoyl group, a nitro group, a nitroso group, a carboxylate group, an acyl group, an acyloxy group, a sulfino group, a sulfonato group, a phosphino group, a phosphinyl group, a phosphonato group, an alkyl ether group, an alkenyl ether group, an alkyl thioether group, an alkenyl thioether group, an aryl ether group, an aryl thioether group, and the like. The hydrogen atom included in the substituent mentioned above may be substituted with a hydrocarbon group. The hydrocarbon group included in the substituent mentioned above may be either linear, branched, or cyclic.

The substituent, which a phenyl group, a polycyclic aromatic hydrocarbon group, or an aromatic heterocyclic group has, is preferably an alkyl group having 1 to 12 carbon atoms, an aryl group having 1 to 12 carbon atoms, an alkoxy group having 1 to 12 carbon atoms, an aryloxy group having 1 to 12 carbon atoms, an arylamino group having 1 to 12 carbon atoms, and a halogen atom.

$R^2$ is preferably an optionally substituted phenyl group, an optionally substituted furyl group, or an optionally substituted thienyl group, since an imidazole compound represented by the formula (1) or the formula (1a) can be synthesized inexpensively and easily, and the imidazole compound has satisfactory solubility in water or an organic solvent.

In the formula (1a), $R^5$ is an optionally substituted alkylene group. The substituent, which an alkylene group may have, is not particularly limited, as long as the object of the present invention is not impaired. Specific examples of the substituent, which an alkylene group may have, include a hydroxy group, an alkoxy group, an amino group, a cyano group, a halogen atom, and the like. The alkylene group may be either a linear alkylene group or a branched alkylene group, and is preferably a linear alkylene group. The number of carbon atoms of the alkylene group is not particularly limited, but is preferably 1 to 20, more preferably 1 to 10, and still more preferably 1 to 5. Note that the number of carbon atoms of the alkylene group does not include the number of carbon atoms of the substituent bonded to an alkylene group.

The alkoxy group as the substituent bonded to the alkylene group may be either a linear alkoxy group or a branched alkoxy group. The number of carbon atoms of the alkoxy group as the substituent is not particularly limited, but is preferably 1 to 10, more preferably 1 to 6, and particularly preferably 1 to 3.

The amino group as the substituent bonded to the alkylene group may be a monoalkylamino group or a dialkylamino group. The alkyl group included in the monoalkylamino group or dialkylamino group may be either a linear alkyl group or a branched alkyl group. The number of carbon atoms of the alkyl group included in the monoalkylamino group or dialkylamino group is not particularly limited, but is preferably 1 to 10, more preferably 1 to 6, and particularly preferably 1 to 3.

Specific examples of the alkylene group suitable as $R^5$ include a methylene group, an ethane-1,2-diyl group, an n-propane-1,3-diyl group, an n-propane-2,2-diyl group, an n-butane-1,4-diyl group, an n-pentane-1,5-diyl group, an n-hexane-1,6-diyl group, an n-heptane-1,7-diyl group, an n-octane-1,8-diyl group, an n-nonane-1,9-diyl group, an n-decane-1,10-diyl group, an n-undecane-1,11-diyl group, an n-dodecane-1,12-diyl group, an n-tridecane-1,13-diyl group, an n-tetradecane-1,14-diyl group, an n-pentadecane-1,15-diyl group, an n-hexadecane-1,16-diyl group, an n-heptadecane-1,17-diyl group, an n-octadecane-1,18-diyl group, an n-nonadecane-1,19-diyl group, and an n-icosane-1,20-diyl group.

$R^3$ is a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group, and n is an integer of 0 to 3. When n is an integer of 2 to 3, a plurality of $R^3$s may be the same or different.

When $R^3$ is an organic group, the organic group is the same as an organic group, which an aromatic group may have as a substituent, as for $R^2$.

When $R^3$ is an organic group, the organic group is preferably an alkyl group, an aromatic hydrocarbon group, and an aromatic heterocyclic group. The alkyl group is preferably a linear or branched alkyl group having 1 to 8 carbon atoms, and more preferably a methyl group, an ethyl group, an n-propyl group, and an isopropyl group. The aromatic hydrocarbon group is preferably a phenyl group, a naphthyl group, a biphenylyl group, an anthryl group, and a phenanthrenyl group, more preferably a phenyl group and a naphthyl group, and particularly preferably a phenyl group. The aromatic heterocyclic group is preferably a pyridyl group, a furyl group, a thienyl group, an imidazolyl group, a pyrazolyl group, an oxazolyl group, a thiazolyl group, an isoxazolyl group, an isothiazolyl group, a benzoxazolyl group, a benzothiazolyl group, and a benzoimidazolyl group, and more preferably a furyl group and a thienyl group.

When $R^3$ is an alkyl group, the position of the alkyl group bonding on an imidazole ring is preferably any one of 2-, 4-, and 5-positions, and more preferably 2-position. When $R^3$ is an aromatic hydrocarbon group and an aromatic heterocyclic group, the position of these groups bonding on imidazole is preferably 2-position.

Among the imidazole compounds represented by the formula (1), a compound represented by the following formula (1-1a) is preferable because it can be synthesized inexpensively and easily.

[Chem. 4]

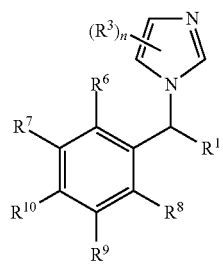

(1-1a)

(In the formula (1-1a), $R^1$, $R^3$, and n are the same as those in the formula (1); and $R^6$, $R^7$, $R^8$, $R^9$, and $R^{10}$ are each independently a hydrogen atom, a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group. At least one of $R^6$, $R^7$, $R^8$, $R^9$, and $R^{10}$ is a group other than a hydrogen atom. At least two of $R^6$, $R^7$, $R^8$, $R^9$, and $R^{10}$ may be bonded to form a ring structure. $R^1$ may be bonded to $R^8$ to form a ring structure.)

$R^6$, $R^7$, $R^8$, $R^9$, and $R^{10}$ are the same as those in the formula (1-1) described below. In the formula (1-1a), $R^1$ may be bonded to $R^8$ to form a ring structure, and in the case in which $R^1$ is an optionally substituted alkyl group, for example, $R^1$ may be bonded to $R^8$ to form a ring structure.

Among imidazole compounds represented by the formula (1a) or the formula (1-1a), a compound represented by the following formula (1-1) is preferable, and a compound represented by the formula (1-1), in which $R^3$ is a methylene group, is more preferable, since these compounds can be synthesized inexpensively and easily, and have excellent solubility in water or an organic solvent.

[Chem. 5]

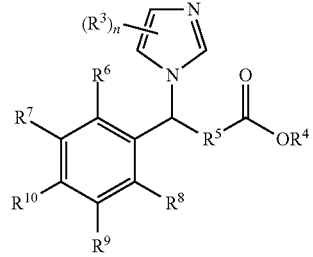

(1-1)

In the formula (1-1), $R^3$, $R^4$, $R^5$, and n are the same as those defined in the formula (1a); and $R^6$, $R^7$, $R^8$, $R^9$, and $R^{10}$ are each independently a hydrogen atom, a halogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group, provided that at least one of $R^6$, $R^7$, $R^8$, $R^9$, and $R^{10}$ is a group other than a hydrogen atom. At least two of $R^6$, $R^7$, $R^8$, $R^9$, and $R^{10}$ may be bonded to form a ring structure. $R^5$ may be bonded to $R^8$ to form a ring structure.

When $R^6$, $R^7$, $R^8$, $R^9$, and $R^{10}$ are organic groups, the organic group is the same as an organic group, which $R^2$ in the formula (1a) has as a substituent. $R^6$, $R^7$, $R^8$, and $R^9$ are preferably hydrogen atoms in view of solubility of an imidazole compound in solvent.

Among these, at least one of $R^6$, $R^7$, $R^8$, $R^9$, and $R^{10}$ is preferably the following substituent; and $R^{10}$ is particularly preferably the following substituent. When $R^{10}$ is the following substituent, $R^6$, $R^7$, $R^8$, and $R^9$ are preferably hydrogen atom.

—O—$R^{11}$ ($R^{11}$ is a hydrogen atom or an organic group.)

When $R^{11}$ is an organic group, the organic group is the same as an organic group, which $R^2$ in the formula (1a) has as a substituent. $R^{11}$ is preferably an alkyl group, more preferably, an alkyl group having 1 to 8 carbon atoms, particularly preferably an alkyl group having 1 to 3 carbon atoms, and most preferably a methyl group.

Among the compounds represented by the formula (1-1) mentioned above, a compound represented by the following formula (1-1-1) is preferable.

[Chem. 6]

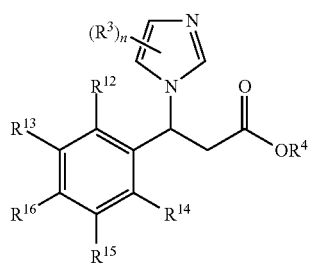

(1-1-1)

In the formula (1-1-1), $R^3$, $R^4$, and n are the same as those defined in the formula (1a); and $R^{12}$, $R^{13}$, $R^{14}$, $R^{15}$, and $R^{16}$ are each independently a hydrogen atom, a hydroxy group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, an amino group, an ammonio group, or an organic group, provided that at least one of $R^{12}$, $R^{13}$, $R^{14}$, $R^{15}$, and $R^{16}$ is a group other than a hydrogen atom.

Among the compounds represented by the formula (1-1-1), at least one of $R^{12}$, $R^{13}$, $R^{14}$, $R^{15}$, and $R^{16}$ is preferably a group represented by the above-mentioned —O—$R^{11}$; and $R^{16}$ is particularly preferably a group represented by —O—$R^{11}$. When $R^{16}$ is a group represented by —O—$R^{11}$, $R^{12}$, $R^{13}$, $R^{14}$, and $R^{15}$ are preferably hydrogen atoms.

The method for synthesizing the imidazole compound represented by the formula (1) is not particularly limited. For example, imidazolylation is performed by reacting a halide represented by $R^2CR^1(Hal)R^1$ ($R^1$ and $R^2$ are the same as those in the formula (1) and Hal is a halogen atom) with an imidazole compound represented by the formula (II) described below in accordance with a conventional method, thereby making it possible to synthesize the imidazole compound represented by the formula (1).

The method for synthesizing the imidazole compound represented by the formula (1a) is not particularly limited. For example, imidazolylation is performed by reacting a halogen-containing carboxylic acid derivative represented by the following formula (I) with an imidazole compound represented by the following formula (II) in accordance with a conventional method, thereby making it possible to synthesize the imidazole compound represented by the formula (1a).

[Chem. 7]

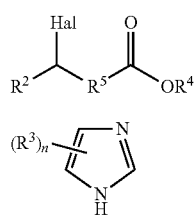

(I)

(II)

In the formulas (I) and (II), $R^2$, $R^3$, $R^4$, $R^5$ and n are the same as those defined in the formula (1a). In the formula (I), Hal is a halogen atom.

When the imidazole compound is a compound represented by the formula (1a) in which $R^5$ is a methylene group, that is, the imidazole compound is a compound represented by the following formula (1-2), it is also possible to synthesize the imidazole compound by the Michael addition reaction which will be described below.

[Chem. 8]

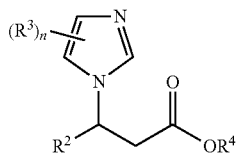

(1-2)

In the formula (1-2), $R^2$, $R^3$, $R^4$ and n are the same as those defined in the formula (1a).

Specifically, for example, a 3-substituted acrylic acid derivative represented by the following formula (III) is mixed with an imidazole compound represented by the above-mentioned formula (II) in a solvent to cause a Michael addition reaction, thereby obtaining an imidazole compound represented by the formula (1-2).

[Chem. 9]

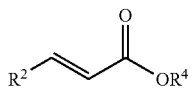

(III)

In the formula (III), $R^2$ and $R^4$ are the same as those defined in the formula (1a).

3-Substituted acrylic acid derivative having an imidazolyl group represented by the following formula (IV) is added in a solvent containing water, thereby obtaining an imidazole compound represented by the following formula (1-3).

[Chem. 10]

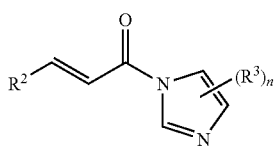

(IV)

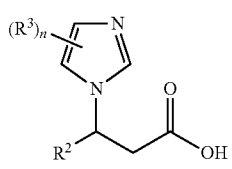

(1-3)

In the formulas (IV) and (1-3), $R^2$, $R^3$ and n are the same as those defined in the formula (1).

In this case, hydrolysis of the 3-substituted acrylic acid derivative represented by the formula (IV) leads to production of the imidazole compound represented by the formula (II) and 3-substituted acrylic acid represented by the following formula (V). Then, the Michael addition reaction occurs between the 3-substituted acrylic acid represented by the following formula (V) and the imidazole compound represented by the formula (II) to produce the above-mentioned imidazole compound represented by the formula (1-3).

[Chem. 11]
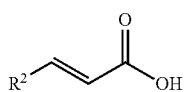
(V)
In the formula (V), R² is the same as those defined in the formula (1a).
Suitable specific examples of the imidazole compound represented by the formula (1) or the formula (1a) include the following.
[Chem. 12]
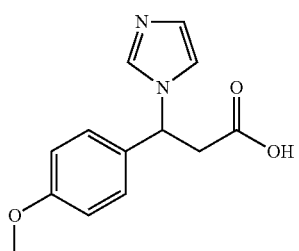
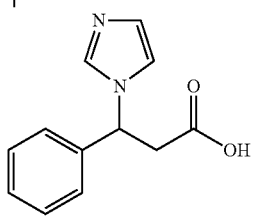
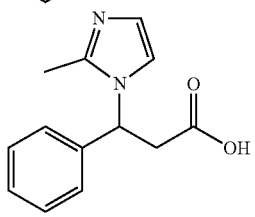
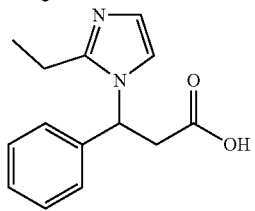
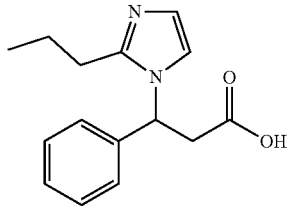
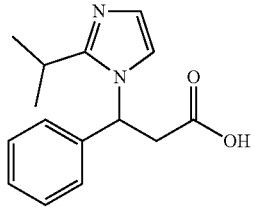
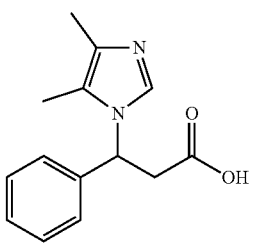
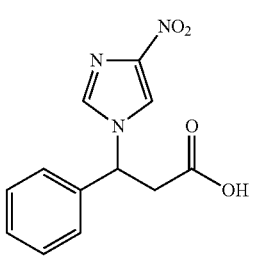
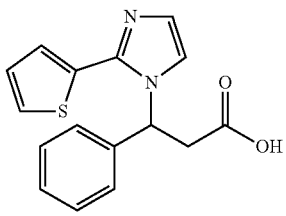
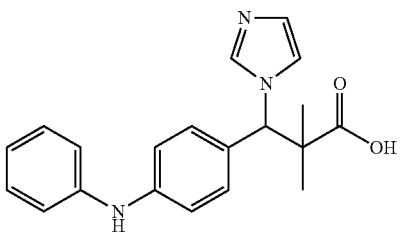
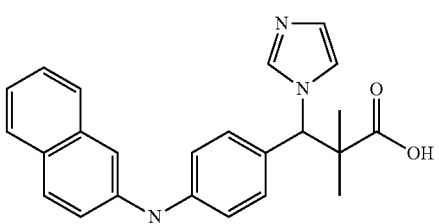
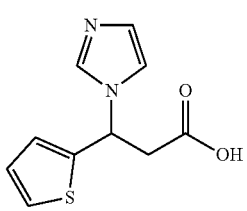
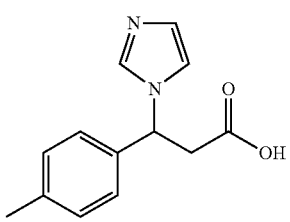

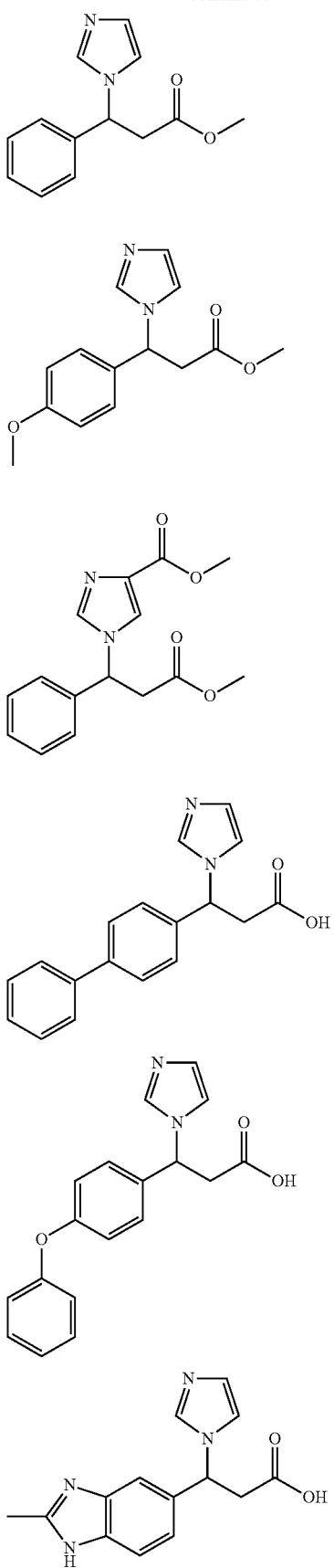

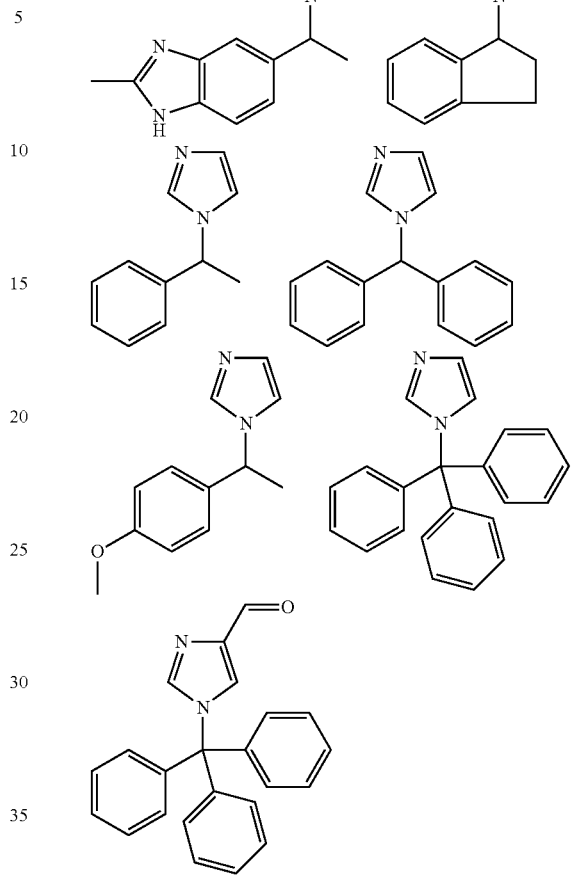

A suitable content of the component (A) in the composition is preferably 0.1 to 20 parts by mass, more preferably 0.5 to 15 parts by mass, particularly preferably 1 to 10 parts by mass with respect to 100 parts by mass of the (B) fine particle. In the case in which the composition contains the component (A) in an amount within the above range, aggregation of the (B) fine particles in the composition with time is excellently inhibited.

<(B) Fine Particle>

The type of the (B) fine particle (hereinafter, also referred to as component (B)) is not particularly limited as long as the volume average particle diameter is 3000 nm or less. The volume average particle diameter of the (B) fine particle is selected as appropriate depending on the intended use of the (B) fine particle. For example, the volume average particle diameter of the (B) fine particle may be 1 to 800 nm, may be 5 to 500 nm, may be 10 to 300 nm, or may be 10 to 100 nm.

The material of the (B) fine particle is not limited to one type of material, and two or more types of materials may be used in combination. In the case in which the fine particle is a particle containing two or more types of materials, the structure of the fine particle may be either a sea-island structure in which a non-matrix material (island component) is dispersed in a matrix (sea component) or a core-shell structure in which a core particle is coated with one or more shell layers.

The fine particle may be an inorganic fine particle, an organic fine particle, or a composite particle consisting of an inorganic material and an organic material.

The shape of the (B) fine particle is not particularly limited as long as the particle is generally recognized as a fine particle. Typical examples of the shape of the (B) fine particle include, but are not limited to, a spherical shape, a columnar shape such as a cylindrical shape or a polygonal-column shape, a polyhedral shape except for a polygonal-column shape, and a plate-like shape. The fine particle may have space inside, that is, may be a porous particle or a hollow particle. In the case in which the fine particle is a hollow particle, the inner space may be filled with liquid. The ratio of the longer diameter to the shorter diameter of the (B) fine particle is not particularly limited but is preferably 1 to 50, more preferably 1 to 10.

From the viewpoints of availability, easy dispersion, and the like, the (B) fine particle is preferably an inorganic fine particle or an organic fine particle. A combination of an inorganic fine particle and an organic fine particle may be used as well.

Specific examples of the particle suitable as the (B) particle include:

white colorant fine particles such as titanium oxide, barium sulfate, magnesium oxide, calcium carbonate, silica, talc, aluminum hydroxide, alumina, and clay;

black colorant fine particles such as perylene-based pigments, C. I. Pigment Black 1, C. I. Pigment Black 7, silver-tin alloy, black titanium oxide, metal oxides, complex inorganic color pigments, metal sulfides, metal sulfates, and metal carbonates of metals such as copper, iron, manganese, cobalt, chromium, nickel, zinc, calcium, and silver;

yellow colorant fine particles such as C. I. Pigment Yellow 1 (the same "C. I. Pigment Yellow" applies to the rest and therefore respective numbers alone are listed below), 3, 11, 12, 13, 14, 15, 16, 17, 20, 24, 31, 53, 55, 60, 61, 65, 71, 73, 74, 81, 83, 86, 93, 95, 97, 98, 99, 100, 101, 104, 106, 108, 109, 110, 113, 114, 116, 117, 119, 120, 125, 126, 127, 128, 129, 137, 138, 139, 147, 148, 150, 151, 152, 153, 154, 155, 156, 166, 167, 168, 175, 180, and 185;

orange colorant fine particles such as C. I. Pigment Orange 1 (the same "C. I. Pigment Orange" applies to the rest and therefore respective numbers alone are listed below), 5, 13, 14, 16, 17, 24, 34, 36, 38, 40, 43, 46, 49, 51, 55, 59, 61, 63, 64, 71, and 73;

purple colorant fine particles such as C. I. Pigment Violet 1 (the same "C. I. Pigment Violet" applies to the rest and therefore respective numbers alone are listed below), 19, 23, 29, 30, 32, 36, 37, 38, 39, 40, and 50;

red colorant fine particles such as C. I. Pigment Red 1 (the same "C. I. Pigment Red" applies to the rest and therefore respective numbers alone are listed below), 2, 3, 4, 5, 6, 7, 8, 9, 10, 11, 12, 14, 15, 16, 17, 18, 19, 21, 22, 23, 30, 31, 32, 37, 38, 40, 41, 42, 48:1, 48:2, 48:3, 48:4, 49:1, 49:2, 50:1, 52:1, 53:1, 57, 57:1, 57:2, 58:2, 58:4, 60:1, 63:1, 63:2, 64:1, 81:1, 83, 88, 90:1, 97, 101, 102, 104, 105, 106, 108, 112, 113, 114, 122, 123, 144, 146, 149, 150, 151, 155, 166, 168, 170, 171, 172, 174, 175, 176, 177, 178, 179, 180, 185, 187, 188, 190, 192, 193, 194, 202, 206, 207, 208, 209, 215, 216, 217, 220, 223, 224, 226, 227, 228, 240, 242, 243, 245, 254, 255, 264, and 265;

blue colorant fine particles such as C. I. Pigment Blue 1 (the same "C. I. Pigment Blue" applies to the rest and therefore respective numbers alone are listed below), 2, 15, 15:3, 15:4, 15:6, 16, 22, 60, 64, and 66;

green colorant fine particles such as C. I. Pigment Green 7, C. I. Pigment Green 36, and C. I. Pigment Green 37; brown colorant fine particles such as C. I. Pigment Brown 23, C. I. Pigment Brown 25, C. I. Pigment Brown 26, and C. I. Pigment Brown 28;

insulating inorganic-oxide fine particles such as $La_2O_3$, $CeO_2$, $Nd_2O_3$, $Gd_2O_3$, $Ho_2O_3$, $Lu_2O_3$, $Hf_2r$, and $Ta_2O_5$;

metal fine particles consisting of gold, silver, copper, nickel, platinum, and aluminum, and alloys of these metals; and resin fine particles consisting of polystyrene, polymethyl (meth)acrylate, a styrene-(methyl (meth)acrylate) copolymer, and the like.

The content of the (B) fine particle in the composition is not particularly limited as long as the object of the present invention is not impaired. The content of the (B) fine particle is preferably 50 to 90% by mass, more preferably 60 to 99% by mass, particularly preferably 70 to 98% by mass with respect to the solid content (mass) of the composition in the case in which the composition does not contain the component (C) described below. In the case in which the composition contains the component (C) described below, the content of the fine particle in the composition is preferably 1 to 60% by mass, more preferably 5 to 50% by mass, further preferably 10 to 40% by mass.

<(C) Base Material>

The composition according to the present invention may contain the (C) base material (hereinafter, also referred to as component (C)) from the viewpoints of shapability and film formation properties. The (C) base material is typically a resin material consisting of a polymer compound or a reactive low-molecular compound that forms crosslinking in response to heat or light exposure to give a polymer compound. The resin material used as the (C) base material may contain a functional group that forms crosslinking in response to heat or light exposure. In other words, a thermosetting or photocurable resin may also be used as the (C) base material.

It is preferable that the (C) base material be a thermosetting or photocurable base material because a shaped body excellent in physical properties such as hardness and tensile elongation tends to be formed. In the case in which the composition contains a thermosetting or photocurable base material as the component (C), subjecting a cured article having a desired shape to heating or light exposure may give a cured article with a desired shape, such as a cured film. Next, specific examples of the component (C) are described in order.

[Resin Material]

A non-curable resin material used as the (C) base material is described. The non-curable resin material is not particularly limited provided that it is a non-curable resin material capable of giving the resulting composition with shapability such as film formation properties. Specific examples of the resin material include polyacetal resin, polyamide resin, polycarbonate resin, polyester resin (polybutylene terephthalate, polyethylene terephthalate, polyarylate and the like), FR-AS resin, FR-ABS resin, AS resin, ABS resin, polyphenylene oxide resin, polyphenylene sulfide resin, polysulfone resin, polyethersulfone resin, polyetheretherketone resin, fluorine-based resin, polyimide resin, polyamideimide resin, polyamide bismaleimide resin, polyetherimide resin, polybenzoxazole resin, polybenzothiazole resin, polybenzimidazole resin, silicone resin, BT resin, polymethylpentene, ultra high molecular weight polyethylene, FR-polypropylene, (meta)acrylic resin (polymethylmethacrylate and the like), polystyrene, and the like. Two or more of these resin materials may be used in combination.

[Thermosetting Low-Molecular Compound]

Examples of the thermosetting low-molecular compound as the component (C) that forms crosslinking in response to heat to give a polymer compound include a polyfunctional (difunctional or more) epoxy compound or a polyfunctional (difunctional or more) oxetane compound. When the composition containing a polyfunctional epoxy compound or a polyfunctional oxetane compound as the (C) base material is heated to a predetermined temperature or higher, epoxy groups or oxetanyl groups of the polyfunctional epoxy compound or the polyfunctional oxetane compound form crosslinking to each other by the action of the component (A) as described above and thereby the resulting shaped body becomes excellent in heat resistance and mechanical properties.

The polyfunctional epoxy compound or the polyfunctional oxetane compound is basically used as the (C) thermosetting base material. However, in the case in which the polyfunctional epoxy compound or the polyfunctional oxetane compound is used in combination with a (D2) acid generator described below that generates an acid by the action of light, the polyfunctional epoxy compound or the polyfunctional oxetane compound may be photo-cured.

The polyfunctional epoxy compound is not particularly limited provided that it is a difunctional or more epoxy compound. Examples of the polyfunctional epoxy compound include difunctional epoxy resins such as a bisphenol A type epoxy resin, a bisphenol F type epoxy resin, a bisphenol S type epoxy resin, a bisphenol AD type epoxy resin, a naphthalene type epoxy resin, and a biphenyl type epoxy resin; glycidyl ester type epoxy resins such as a dimer acid glycidyl ester and a triglycidyl ester; glycidylamine type epoxy resins such as tetraglycidyl aminodiphenylmethane, triglycidyl-p-aminophenol, tetraglycidyl metaxylylenediamine, and tetraglycidyl bisaminomethylcyclohexane; heterocyclic epoxy resins such as triglycidyl isocyanurate; trifunctional type epoxy resins such as phloroglucinol triglycidyl ether, trihydroxybiphenyl triglycidyl ether, trihydroxyphenylmethane triglycidyl ether, glycerin triglycidyl ether, 2-[4-(2,3-epoxypropoxy)phenyl]-2-[4-[1,1-bis[4-(2,3-epoxypropoxy)phenyl]ethyl]phenyl]propane, and 1,3-bis[4-[1-[4-(2,3-epoxypropoxy)phenyl]-1-[4-[1-[4-(2,3-epoxypropoxy)phenyl]-1-methylethyl]phenyl]ethyl]phenoxy]-2-propanol; and tetrafunctional type epoxy resins such as tetrahydroxyphenylethane tetraglycidyl ether, tetraglycidyl-benzophenone, bisresorcinol tetraglycidyl ether, and tetraglycidoxybiphenyl.

An alicyclic epoxy compound is also preferable as the polyfunctional epoxy compound from the viewpoint that the resulting cured article has a high hardness. Specific examples of the alicyclic epoxy compound include 2-(3,4-epoxycyclohexyl-5,5-spiro-3,4-epoxy)cyclohexane-meta-dioxane, bis(3,4-epoxycyclohexylmethyl)adipate, bis(3,4-epoxy-6-methylcyclohexylmethyl)adipate, 3,4-epoxy-6-methylcyclohexyl-3',4'-epoxy-6'-methylcyclohexane carboxylate, ε-caprolactone-modified 3,4-epoxycyclohexylmethyl-3',4'-epoxycyclohexane carboxylate, trimethyl-caprolactone-modified 3,4-epoxycyclohexylmethyl-3',4'-epoxycyclohexane carboxylate, β-methyl-5-valerolactone-modified 3,4-epoxycyclohexylmethyl-3',4'-epoxycyclohexane carboxylate, methylenebis(3,4-epoxycyclohexane), di(3,4-epoxycyclohexylmethyl)ether of ethylene glycol, ethylenebis(3,4-epoxycyclohexane carboxylate), dioctyl epoxycyclohexahydrophthalate, di-2-ethylhexyl epoxycyclohexahydrophthalate, an epoxy resin having a tricyclodecene oxide group, and a compound represented by the following formula (a1).

An epoxy-group-containing fluorene compound may also be suitable for use as the polyfunctional epoxy compound. Examples of the epoxy-group-containing fluorene compound include 9,9-bis[4-(glycidyloxy)phenyl]-9H-fluorene, 9,9-bis[4-(2-(glycidyloxy)ethoxy]phenyl]-9H-fluorene, 9,9-bis[4-[2-(glycidyloxy)ethyl]phenyl]-9H-fluorene, 9,9-bis[4-(glycidyloxy)-3-methylphenyl]-9H-fluorene, 9,9-bis[4-(glycidyloxy)-3,5-dimethylphenyl]-9H-fluorene, and 9,9-bis(6-glycidyloxynaphthalen-2-yl)-9H-fluorene.

Of these specific examples of the epoxy compound, an alicyclic epoxy compound represented by the following formula (c1) is preferable since it gives a cured article which has high hardness.

[Chem. 13]

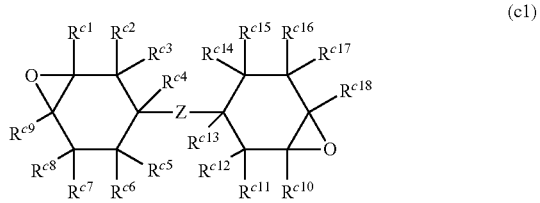

(c1)

In the formula (c1), Z is a single bond, or a divalent group selected from the group consisting of —O—, —O—CO—, —S—, —SO—, —SO$_2$—, —CH$_2$—, —C(CH$_3$)$_2$—, —CBr$_2$—, —C(CBr$_3$)$_2$—, —C(CF$_3$)$_2$—, and —R$^{c19}$—O—CO—; R$^{c19}$ is an alkylene group having 1 to 8 carbon atoms; and R$^{c1}$ to R$^{c18}$ each independently represent a group selected from the group consisting of a hydrogen atom, a halogen atom, and an organic group.

In the formula (c1), R$^{c19}$ is an alkylene group having 1 to 8 carbon atoms, and is preferably a methylene group or an ethylene group.

When R$^{c1}$ to R$^{c18}$ are organic groups, the organic group is not particularly limited as long as the object of the present invention is not impaired, and may be a hydrocarbon group, or a group consisting of a carbon atom and a halogen atom, or a group having heteroatoms such as a halogen atom, an oxygen atom, a sulfur atom, a nitrogen atom, and a silicon atom, together with a carbon atom and a hydrogen atom. Examples of the halogen atom include a chlorine atom, a bromine atom, an iodine atom, and a fluorine atom.

The organic group is preferably a group consisting of a hydrocarbon group, a carbon atom, a hydrogen atom, and an oxygen atom; a group consisting of a halogenated hydrocarbon group, a carbon atom, an oxygen atom, and a halogen atom; and a group consisting of a carbon atom, a hydrogen atom, an oxygen atom, and a halogen atom. When the organic group is a hydrocarbon group, the hydrocarbon group may be an aromatic hydrocarbon group, or an aliphatic hydrocarbon group, or a group including an aromatic skeleton and an aliphatic skeleton. The number of carbon atoms of the organic group is preferably 1 to 20, more preferably 1 to 10, and particularly preferably 1 to 5.

Specific examples of the hydrocarbon group include chain alkyl groups such as a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, a 2-ethylhexyl group, an n-nonyl group, an n-decyl group, an n-undecyl group, an n-tridecyl group, an n-tetradecyl group, an n-pentadecyl group, an n-hexadecyl group, an n-heptadecyl group, an n-octadecyl group, an n-nonadecyl group, and an n-icosyl group; chain alkenyl groups such as a vinyl group, a 1-propenyl group, a 2-n-propenyl group (allyl group), a 1-n-butenyl group, a 2-n-butenyl group, and a 3-n-butenyl group; cycloalkyl groups such as a cyclopropyl group, a cyclobutyl group, a cyclopentyl group, a cyclohexyl group, and a cycloheptyl group; aryl groups such as a phenyl group, an o-tolyl group, an m-tolyl group, a p-tolyl group, an α-naphthyl group, a β-naphthyl group, a biphenyl-4-yl group, a biphenyl-3-yl group, a biphenyl-2-yl group, an anthryl group, and a phenanthryl group; and aralkyl groups such as a benzyl group, a phenethyl group, an α-naphthylmethyl group, a β-naphthylmethyl group, an α-naphthylethyl group, and a β-naphthylethyl group.

Specific examples of the halogenated hydrocarbon group include halogenated chain alkyl groups such as a chloromethyl group, a dichloromethyl group, a trichloromethyl group, a bromomethyl group, a dibromomethyl group, a tribromomethyl group, a fluoromethyl group, a difluoromethyl group, a trifluoromethyl group, a 2,2,2-trifluoroethyl group, a pentafluoroethyl group, a heptafluoropropyl group, a perfluorobutyl group, and a perfluoropentyl group, a perfluorohexyl group, a perfluoroheptyl group, a perfluorooctyl group, a perfluorononyl group, and a perfluorodecyl group; halogenated cycloalkyl groups such as a 2-chlorocyclohexyl group, a 3-chlorocyclohexyl group, a 4-chlorocyclohexyl group, a 2,4-dichlorocyclohexyl group, a 2-bromocyclohexyl group, a 3-bromocyclohexyl group, and a 4-bromocyclohexyl group; halogenated aryl groups such as a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2-bromophenyl group, a 3-bromophenyl group, a 4-bromophenyl group, a 2-fluorophenyl group, a 3-fluorophenyl group, and a 4-fluorophenyl group; and halogenated aralkyl groups such as a 2-chlorophenylmethyl group, a 3-chlorophenylmethyl group, a 4-chlorophenylmethyl group, a 2-bromophenylmethyl group, a 3-bromophenylmethyl group, a 4-bromophenylmethyl group, a 2-fluorophenylmethyl group, a 3-fluorophenylmethyl group, and a 4-fluorophenylmethyl group.

Specific examples of the group consisting of a carbon atom, a hydrogen atom, and an oxygen atom include hydroxy chain alkyl groups such as a hydroxymethyl group, a 2-hydroxyethyl group, a 3-hydroxy-n-propyl group, and a 4-hydroxy-n-butyl group; hydroxycycloalkyl groups such as a 2-hydroxycyclohexyl group, a 3-hydroxycyclohexyl group, and a 4-hydroxycyclohexyl group; hydroxyaryl groups such as a 2-hydroxyphenyl group, a 3-hydroxyphenyl group, a 4-hydroxyphenyl group, a 2,3-dihydroxyphenyl group, a 2,4-dihydroxyphenyl group, a 2,5-dihydroxyphenyl group, a 2,6-dihydroxyphenyl group, a 3,4-dihydroxyphenyl group, and a 3,5-dihydroxyphenyl group; hydroxyaralkyl groups such as a 2-hydroxyphenylmethyl group, a 3-hydroxyphenylmethyl group, and a 4-hydroxyphenylmethyl group; chain alkoxy groups such as a methoxy group, an ethoxy group, an n-propyloxy group, an isopropyloxy group, an n-butyloxy group, an isobutyloxy group, a sec-butyloxy group, a tert-butyloxy group, an n-pentyloxy group, an n-hexyloxy group, an n-heptyloxy group, an n-octyloxy group, a 2-ethylhexyloxy group, an n-nonyloxy group, an n-decyloxy group, an n-undecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group, and an n-icosyloxy group; chain alkenyloxy groups such as a vinyloxy group, a 1-propenyloxy group, a 2-n-propyloxy group (allyloxy group), a 1-n-butenyloxy group, a 2-n-butenyloxy group, and a 3-n-butenyloxy group; aryloxy groups such as a phenoxy group, an o-tolyloxy group, an m-tolyloxy group, a p-tolyloxy group, an α-naphthyloxy group, a β-naphthyloxy group, a biphenyl-4-yloxy group, a biphenyl-3-yloxy group, a biphenyl-2-yloxy group, an anthryloxy group, and a phenanthryloxy group; aralkyloxy groups such as a benzyloxy group, a phenethyloxy group, an α-naphthylmethyloxy group, a β-naphthylmethyloxy group, an α-naphthylethyloxy group, and a β-naphthylethyloxy group; alkoxyalkyl groups such as a methoxymethyl group, an ethoxymethyl group, an n-propyloxymethyl group, a 2-methoxyethyl group, a 2-ethoxyethyl group, a 2-n-propyloxyethyl group, a 3-methoxy-n-propyl group, a 3-ethoxy-n-propyl group, a 3-n-propyloxy-n-propyl group, a 4-methoxy-n-butyl group, a 4-ethoxy-n-butyl group, and a 4-n-propyloxy-n-butyl group; alkoxyalkoxy groups such as a methoxymethoxy group, an ethoxymethoxy group, an n-propyloxymethoxy group, a 2-methoxyethoxy group, a 2-ethoxyethoxy group, a 2-n-propyloxyethoxy group, a 3-methoxy-n-propyloxy group, a 3-ethoxy-n-propyloxy group, a 3-n-propyloxy-n-propyloxy group, a 4-methoxy-n-butyloxy group, a 4-ethoxy-n-butyloxy group, and a 4-n-propyloxy-n-butyloxy group; alkoxyaryl groups such as a 2-methoxyphenyl group, a 3-methoxyphenyl group, and a 4-methoxyphenyl group; alkoxyaryloxy groups such as a 2-methoxyphenoxy group, a 3-methoxyphenoxy group, and a 4-methoxyphenoxy group; aliphatic acyl groups such as a formyl group, an acetyl group, a propionyl group, a butanoyl group, a pentanoyl group, a hexanoyl group, a heptanoyl group, an octanoyl group, a nonanoyl group, and a decanoyl group; aromatic acyl groups such as a benzoyl group, an α-naphthoyl group, and a β-naphthoyl group; chain alkyloxycarbonyl groups such as a methoxycarbonyl group, an ethoxycarbonyl group, an n-propyloxycarbonyl group, an n-butyloxycarbonyl group, an n-pentyloxycarbonyl group, an n-hexylcarbonyl group, an n-heptyloxycarbonyl group, an n-octyloxycarbonyl group, an n-nonyloxycarbonyl group, and an n-decyloxycarbonyl group; aryloxycarbonyl groups such as a phenoxycarbonyl group, an α-naphthoxycarbonyl group, and a β-naphthoxycarbonyl group; aliphatic acyloxy groups such as a formyloxy group, an acetyloxy group, a propionyloxy group, a butanoyloxy group, a pentanoyloxy group, a hexanoyloxy group, a heptanoyloxy group, an octanoyloxy group, a nonanoyloxy group, and a decanoyloxy group; and aromatic acyloxy groups such as a benzoyloxy group, an α-naphthoyloxy group, and a β-naphthoyloxy group.

$R^{c1}$ to $R^{c18}$ are preferably each independently a group selected from the group consisting of a hydrogen atom, a halogen atom, an alkyl group having 1 to 5 carbon atoms, and an alkoxy group having 1 to 5 carbon atoms and, particularly, all $R^{c1}$ to $R^{c18}$ are more preferably hydrogen atoms in view of the hardness of a cured article obtained by using the composition.

Specific examples of a suitable compound for the alicyclic epoxy compounds represented by the formula (c1) include the following compounds 1 and 2.

[Chem. 14]

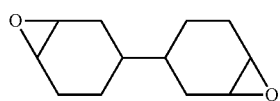

Compound 1

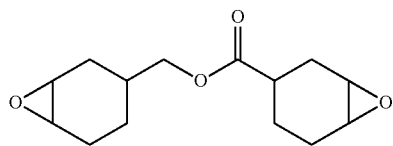

Compound 2

Examples of the polyfunctional (difunctional or more) oxetane compound include 3,3'-(oxybismethylene)bis(3-ethyloxetane), 4,4-bis[(3-ethyl-3-oxetanyl)methyl]biphenyl, 3,7-bis(3-oxetanyl)-5-oxanonane, 3,3'-[1,3-(2-methylenyl)propanediylbis(oxymethylene)]bis(3-ethyloxetane), 1,4-bis[(3-ethyl-3-oxetanyl)methoxymethyl]benzene, 1,2-bis[(3-ethyl-3-oxetanyl)methoxymethyl]ethane, 1,3-bis[(3-ethyl-3-oxetanyl)methoxymethyl]propane, ethyleneglycolbis[(3-ethyl-3-oxetanyl)methyl] ether, dicyclopentenylbis[(3-ethyl-3-oxetanyl)methyl] ether, triethyleneglycolbis[(3-ethyl-3-oxetanyl)methyl] ether, tetraethyleneglycolbis[(3-ethyl-3-oxetanyl)methyl] ether, tricyclodecanediyldimethylenebis[(3-ethyl-3-oxetanyl)methyl] ether, trimethylolpropanetris[(3-ethyl-3-oxetanyl)methyl] ether, 1,4-bis[(3-ethyl-3-oxetanyl)methoxy]butane, 1,6-bis[(3-ethyl-3-oxetanyl)methoxy]hexane, pentaerythritoltris[(3-ethyl-3-oxetanyl)methyl] ether, pentaerythritoltetrakis[(3-ethyl-3-oxetanyl)methyl] ether, polyethyleneglycolbis[(3-ethyl-3-oxetanyl)methyl] ether, dipentaerythritolhexakis[(3-ethyl-3-oxetanyl)methyl] ether, dipentaerythritolpentakis[(3-ethyl-3-oxetanyl)methyl] ether, and dipentaerythritoltetrakis[(3-ethyl-3-oxetanyl)methyl] ether.

The polyfunctional oxetane compound may also be, for example, a reaction product of dipentaerythritolhexakis[(3-ethyl-3-oxetanyl)methyl] ether and caprolactone, a reaction product of dipentaerythritolpentakis[(3-ethyl-3-oxetanyl)methyl] ether and caprolactone, a reaction product of ditrimethylolpropanetetrakis[(3-ethyl-3-oxetanyl)methyl] ether, bisphenol A bis[(3-ethyl-3-oxetanyl)methyl] ether, and ethylene oxide, a reaction product of bisphenol A bis[(3-ethyl-3-oxetanyl)methyl] ether and propylene oxide, a reaction product of hydrogenated bisphenol A bis[(3-ethyl-3-oxetanyl)methyl] ether and ethylene oxide, a reaction product of hydrogenated bisphenol A bis[(3-ethyl-3-oxetanyl)methyl]ether and propylene oxide, or a reaction product of bisphenol F bis[(3-ethyl-3-oxetanyl)methyl] ether and ethylene oxide.

[Thermosetting Polymer Compound]

Examples of the thermosetting polymer compound that may be used as the component (C) include a resin that causes an aromatic ring formation reaction within a molecule and/or a crosslinking reaction between molecules in response to heat. The composition according to the present invention contains the (A) imidazole compound described above and therefore in the composition according to the present invention, an aromatic ring formation reaction within a molecule and/or a crosslinking reaction between molecules tends to occur in the component (C) in response to heat.

In the case in which an aromatic ring formation reaction within a molecule occurs, the structure of a molecular chain constituting the resin becomes rigid and therefore the resulting composition tends to give a shaped body excellent in heat resistance and mechanical properties. Examples of a preferable reaction as the aromatic ring formation reaction within a molecule include reactions shown by the following formulae (I) to (VI). The reactions in the following formulae are mere examples of the aromatic ring formation reaction. The structure of the resin used as the (A) base material that causes an aromatic ring formation reaction within a molecule in response to heat is not limited to the structures of the precursor polymers shown in the following formulae.

[Chem. 15]

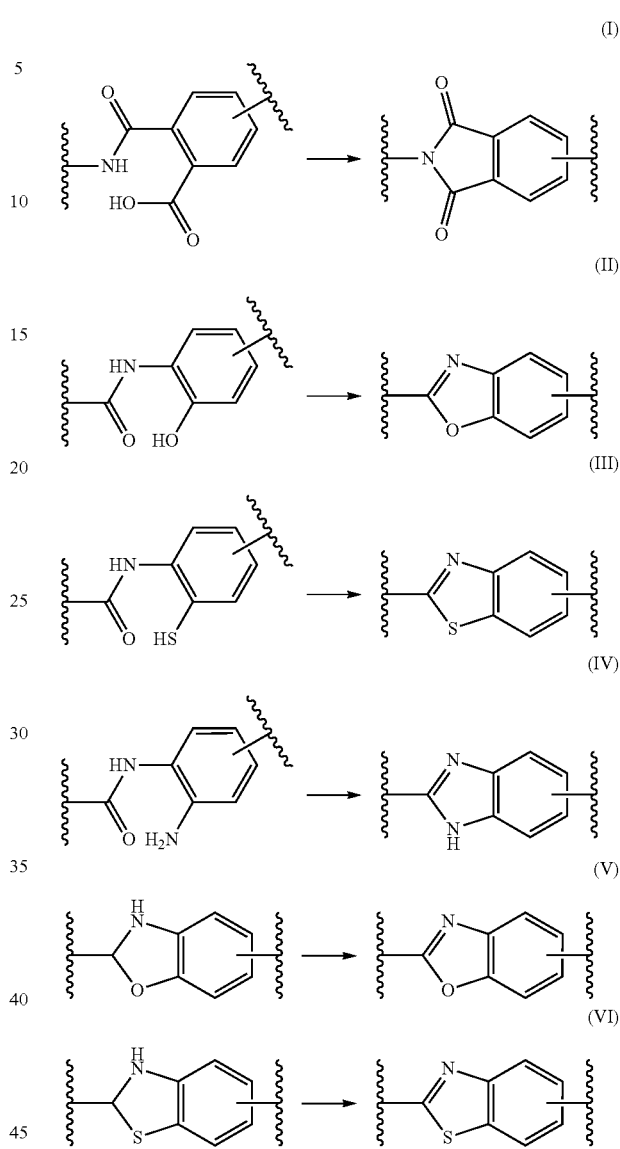

In the case in which a crosslinking reaction between molecules occurs, molecular chains constituting the resin crosslink to each other and thereby a three-dimensional crosslinked structure is formed. Therefore, by using the composition containing a resin that causes a crosslinking reaction in response to heat as the component (C), a shaped body excellent in heat resistance and mechanical properties tends to be obtained.

As the resin that causes a crosslinking reaction between molecules in response to heat, a resin containing a group selected from a hydroxy group, a carboxylic anhydride group, a carboxy group, and an epoxy group in the molecule is preferable. In the case in which a resin containing a hydroxy group is used, the action of the component (A) causes dehydration condensation between hydroxy groups and thereby causes crosslinking between molecules in the resin. In the case in which a resin containing a carboxylic anhydride group is used, acid anhydride groups are hydrolyzed and the resulting carboxy groups undergo dehydration condensation by the action of the component (A) and thereby form crosslinking. In the case in which a resin containing a carboxy group is used, the action of the component (A) causes dehydration condensation between carboxy groups and thereby causes crosslinking between molecules in the resin. In the case in which a resin containing an epoxy group is used, the action of the component (A) causes a polyaddition reaction between epoxy groups and thereby causes crosslinking between molecules in the resin.

Among these compounds that cause an aromatic ring formation reaction within a molecule or a crosslinking reaction between molecules in response to heat, polyamic acid, a polybenzoxazole precursor, a polybenzothiazole precursor, a polybenzimidazole precursor, a styrene-(maleic acid) copolymer, and an epoxy-group-containing resin are preferable because a shaped body excellent in heat resistance tends to be formed. Next, specific examples of a suitable thermosetting polymer compound are described.

(Hydroxy-Group-Containing Resin)

Examples of a resin containing a hydroxy group in the molecule include a novolac resin. The novolac resin is not particularly limited but it is preferable that the novolac resin be obtained by condensation reaction of 1 mol of phenol with 0.5 to 1.0 mol of a condensation agent such as formaldehyde or paraformaldehyde in the presence of an acidic catalyst.

Examples of the phenol include phenol, cresols such as o-cresol, m-cresol, and p-cresol; xylenols such as 2,3-xylenol, 2,4-xylenol, 2,5-xylenol, 2,6-xylenol, 3,4-xylenol, and 3,5-xylenol; ethylphenols such as o-ethylphenol, m-ethylphenol, and p-ethylphenol, alkylphenols such as 2-isopropylphenol, 3-isopropylphenol, 4-isopropylphenol, o-butylphenol, m-butylphenol, p-butylphenol, and p-tert-butylphenol; trialkylphenols such as 2,3,5-trimethylphenol and 3,4,5-trimethylphenol; polyphenols such as resorcinol, catechol, hydroquinone, hydroquinone monomethyl ether, pyrogallol, and fluoroglycinol; and alkyl polyphenols such as alkylresorcins, alkylcatechols, and alkylhydroquinones (respective alkyl groups have 1 to 4 carbon atoms), α-naphthol, β-naphthol, hydroxydiphenyl, and bisphenol A. The phenol may be used either singly or in combination of two or more.

Among these phenols, m-cresol and p-cresol are preferable and a combination of m-cresol and p-cresol is more preferable. By adjusting the blending ratio between m-cresol and p-cresol, various properties such as photoresist sensitivity and heat resistance may be adjusted. The blending ratio of m-cresol to p-cresol is not particularly limited but m-cresol/p-cresol=3/7 to 8/2 (mass ratio) is preferable. In the case in which the ratio of m-cresol is lower than the lower limit described above, sensitivity may decrease. In the case in which the ratio of m-cresol is higher than the upper limit described above, heat resistance may decrease.

Examples of the acidic catalyst used for production of the novolac resin include inorganic acids such as hydrochloric acid, sulfuric acid, nitric acid, phosphoric acid, and phosphorous acid, organic acids such as formic acid, oxalic acid, acetic acid, diethyl sulfate, and p-toluenesulfonic acid, and metal salts such as zinc acetate. The acidic catalyst may be used either singly or in combination of two or more.

The mass average molecular weight of the novolac resin in terms of polystyrene measured by gel permeation chromatography (GPC) is preferably 1000 to 50000.

(Carboxylic-Anhydride-Group-Containing Resin)

As a resin containing a carboxylic anhydride group in the molecule, a copolymer obtained by polymerizing a mixture of unsaturated-double-bond-containing monomers is preferable. The mixture contains one or more monomers selected from maleic anhydride, citraconic anhydride, and itaconic anhydride. The polymer is preferably a styrene-(maleic acid) copolymer.

As a resin containing a carboxy group in the molecule, a resin obtained by hydrolyzing an acid anhydride group in the resin containing a carboxylic anhydride group in the molecule described above and a copolymer obtained by polymerizing a mixture of unsaturated-double-bond-containing monomers are preferable. The mixture contains one or more monomers selected from (meth)acrylic acid, crotonic acid, maleic acid, fumaric acid, citraconic acid, mesaconic acid, and itaconic acid.

(Polyamic Acid)

The polyamic acid is a base material that serves as a precursor of a polyimide resin. In the case in which the composition is shaped into a desired shape and then the shaped composition is heated to an appropriate temperature, the action of the component (A) promotes a ring closure reaction in which a polyimide resin is produced from polyamic acid and, thereby, a shaped body containing a polyimide resin excellent in heat resistance as a matrix is formed.

Molecular weight (mass average molecular weight) of the polyamic acid is preferably 5,000 to 30,000, and more preferably 10,000 to 20,000. In the case in which a polyamic acid having a mass average molecular weight within this range is used, a shaped body excellent in heat resistance tends to be formed.

As a preferred polyamic acid, polyamic acid consisting of a constituent unit represented by the following formula (C1) can be exemplified.

[Chem. 16]

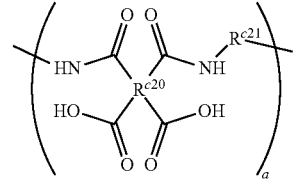

(C1)

(In the formula (C1), $R^{c20}$ is a tetravalent organic group; $R^{c21}$ is a divalent organic group; and a is the number of repetitions of the constituent unit represented by the formula (C1).)

In the formula (C1), the number of carbon atoms of each of $R^{c20}$ and $R^{c21}$ is preferably 2 to 50, and more preferably 2 to 30. Each of $R^{c20}$ and $R^{c21}$ may be either an aliphatic group, an aromatic group, or a group with a combination of these structures. $R^{c20}$ and $R^{c21}$ may include, in addition to a carbon atom and a hydrogen atom, a halogen atom, an oxygen atom, and a sulfur atom. In a case in which $R^{c20}$ and $R^{c21}$ include an oxygen atom, a nitrogen atom or a sulfur atom, the oxygen atom, the nitrogen atom or the sulfur atom may be included in $R^{c20}$ and $R^{c21}$ as a group selected from: a nitrogen-containing heterocyclic group; —CONH—; —NH—; —N=N—; —CH=N—; —COO—; —O—; —CO—; —SO—; —SO$_2$—; —S—; and —S—S—, and more preferably included in $R^{c20}$ and $R^{c21}$ as a group selected from: —O—; —CO—; —SO—; —SO$_2$—; —S—; and —S—S—.

Polyamic acid is generally prepared by reacting a tetracarboxylic dianhydride component with a diamine component. Hereinafter, the tetracarboxylic dianhydride component and the diamine component used for preparation of the polyamic acid, and a manufacturing method of the polyamic acid are described.

Tetracarboxylic Dianhydride Component

The tetracarboxylic dianhydride component, which is a synthesis material for the polyamic acid, is not particularly limited as long as it can generate the polyamic acid by reacting with the diamine component. The tetracarboxylic dianhydride component can be appropriately selected from tetracarboxylic dianhydrides which are conventionally used as a synthesis material for the polyamic acid. The tetracarboxylic dianhydride component may be either an aromatic tetracarboxylic dianhydride or an aliphatic tetracarboxylic dianhydride; however, an aromatic tetracarboxylic dianhydride is preferable. The tetracarboxylic dianhydride component may be used in combination of two or more.

Specific examples of preferred aromatic tetracarboxylic dianhydride include: pyromellitic dianhydride; 3,3',4,4'-biphenyl tetra carboxylic dianhydride; 2,3,3',4'-biphenyl tetra carboxylic dianhydride; 3,3',4,4'-benzophenone tetra carboxylic dianhydride; 4,4'-oxydiphthalic anhydride; 3,3',4,4'-diphenyl sulfone tetra carboxylic dianhydride; and the like. Among these, 3,3',4,4'-biphenyl tetra carboxylic dianhydride and pyromellitic dianhydride are preferable from the viewpoint of price, availability, and the like.

Diamine Component

The diamine component, which is a synthesis material for the polyamic acid, is not particularly limited as long as it can generate the polyamic acid by reacting with the tetracarboxylic dianhydride component. The diamine component can be appropriately selected from diamines which are conventionally used as a synthesis material for the polyamic acid. The diamine component may be either an aromatic diamine or an aliphatic diamine; however, an aromatic diamine is preferable. The diamine component may be used in combination of two or more.

Specific examples of preferred aromatic diamine include: p-phenylenediamine; m-phenylenediamine; 2,4-diamino toluene; 4,4'-diamino biphenyl; 4,4'-diamino-2,2'-bis (trifluoromethyl) biphenyl; 3,3'-diaminodiphenyl sulfone; 4,4'-diaminodiphenyl sulfone; 4,4'-diaminodiphenyl sulfide; 4,4'-diaminodiphenylmethane; 4,4'-diamino diphenyl ether; 3,4'-diamino diphenyl ether; 3,3'-diamino diphenyl ether; 1,4-bis (4-aminophenoxy) benzene; 1,3-bis (4-aminophenoxy) benzene; 1,3-bis (3-aminophenoxy) benzene; 4,4'-bis (4-aminophenoxy) biphenyl; bis[4-(4-aminophenoxy) phenyl] sulfone; bis[4-(3-aminophenoxy) phenyl] sulfone; 2,2-bis[4-(4-aminophenoxy) phenyl] propane; 2,2-bis[4-(4-amino phenoxy) phenyl]hexafluoropropane; 9,9-bis(4-aminophenyl)-9H-fluorene; 9,9-bis(4-amino-3-methylphenyl)-9H-fluorene; 4,4'-[1,4-phenylenebis(1-methylethane-1,1-diyl)]dianiline; and the like. Among these, p-phenylenediamine, m-phenylenediamine, 2,4-diamino toluene, and 4,4'-diamino diphenyl ether are preferable from the viewpoint of price, availability, and the like.

Manufacturing Method of Polyamic Acid

The polyamic acid can be obtained by reacting the above described tetracarboxylic dianhydride component with the diamine component in solvent in which both of the components are soluble. Amounts of the tetracarboxylic dianhydride component and the diamine component to be used upon synthesis of the polyamic acid are not particularly limited; however, it is preferable to use 0.50 to 1.50 moles, and more preferable to use 0.60 to 1.30 moles, and particularly preferable to use 0.70 to 1.20 moles of the diamine component with respect to 1 mole of the tetracarboxylic dianhydride component.

Solvents which can be used for synthesis of the polyamic acid include, for example: aprotic polar organic solvents such as N,N,N',N'-tetramethyl urea, N-methyl-2-pyrrolidone, N,N-dimethylformamide, N,N-dimethylacetamide, hexamethylphosphoramide, 1,3-dimethyl-2-imidazolidinone and the γ-butyrolactone; and glycol ethers such as diethyleneglycol dialkyl ether, ethyleneglycol monoalkyl ether acetate, diethyleneglycol monoalkyl ether acetate, propylene glycol monoalkyl ether acetate and propylene glycol monoalkyl ether propionate. These solvents can be used in combining two or more types. Among these, it is preferable to use N,N,N',N'-tetramethyl urea.

An amount of the solvent to be used upon synthesis of the polyamic acid is not particularly limited as long as the polyamic acid of a desired molecular weight can be synthesized. Typically, the amount of the solvent to be used is preferably 100 to 4000 parts by mass and more preferably 150 to 2000 parts by mass with respect to 100 parts by mass of a combination of the tetracarboxylic dianhydride component and the diamine component.

The temperature at which the reaction between the tetracarboxylic dianhydride component and the diamine component is carried out is not particularly limited as long as the reaction proceeds preferably. Typically, the temperature at which the reaction between the tetracarboxylic dianhydride component and the diamine component is carried out is preferably −5 to 150° C., more preferably 0 to 120° C., and particularly preferably 0 to 70° C. The duration of the reaction between the tetracarboxylic dianhydride component and the diamine component depends on the reaction temperature; however, the duration is preferably 1 to 50 hours, more preferably 2 to 40 hours, and particularly preferably 5 to 30 hours.

By the above method, a solution or a paste of polyamic acid is obtained. The resulting solution or paste may be used as it is for preparation of the composition. Alternatively, the resulting solution or paste of polyamic acid may be subjected to solvent removal and then the resulting solid polyamic acid may be used for preparation of the composition.

(Polybenzoxazole Precursor)

The polybenzoxazole precursor is typically produced by reaction of an aromatic diamine diol with a dicarbonyl compound having a specific structure. Next, the aromatic diamine diol, the dicarbonyl compound, a solvent used for synthesis of the polybenzoxazole precursor, and the method for producing the polybenzoxazole precursor are described.

Aromatic Diamine Diol

The aromatic diamine diol may be any aromatic diamine diol that is conventionally used in polybenzoxazole synthesis. A preferable aromatic diamine diol is a compound represented by the following formula (c2). The aromatic diamine diol may be used either singly or in combination of two or more.

[Chem. 17]

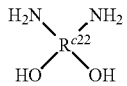

(c2)

(In the formula (c2), $R^{c22}$ is a tetravalent organic group containing one or more aromatic rings; and in either of the two pairs of an amino group and a hydroxy group in the aromatic diamine diol represented by the formula (c2), the amino group and the hydroxy group are bonded to two carbon atoms that are adjacent to each other on an aromatic ring in $R^{c22}$.)

In the formula (c2), $R^{c22}$ is a tetravalent organic group containing one or more aromatic rings and the number of carbon atoms is preferably 6 to 50, more preferably 6 to 30. $R^{c22}$ may be an aromatic group or may be a group having two or more aromatic groups bonded to each other via an aliphatic hydrocarbon group and a halogenated aliphatic hydrocarbon group, or a bond containing a heteroatom such as an oxygen atom, a sulfur atom, or a nitrogen atom. Examples of the bond containing a heteroatom such as an oxygen atom, a sulfur atom, or a nitrogen atom in $R^{c22}$ include —CONH—, —NH—, —N=N—, —CH=N—, —COO—, —O—, —CO—, —SO—, —SO$_2$—, —S—, and —S—S—, and —O—, —CO—, —SO—, —SO$_2$—, —S—, and —S—S— are preferable.

The aromatic ring in $R^{c22}$ may be an aromatic heterocycle. The aromatic ring that is bonded to an amino group and a hydroxy group in $R^{c22}$ is preferably a benzene ring. In the case in which a ring that is bonded to an amino group and a hydroxy group in $R^{c22}$ is a condensed ring containing two or more rings, the ring that is bonded to an amino group and a hydroxy group in the condensed ring is preferably a benzene ring.

Suitable examples of $R^{c22}$ include groups represented by the following formulae (c1-1) to (c1-9).

[Chem. 18]

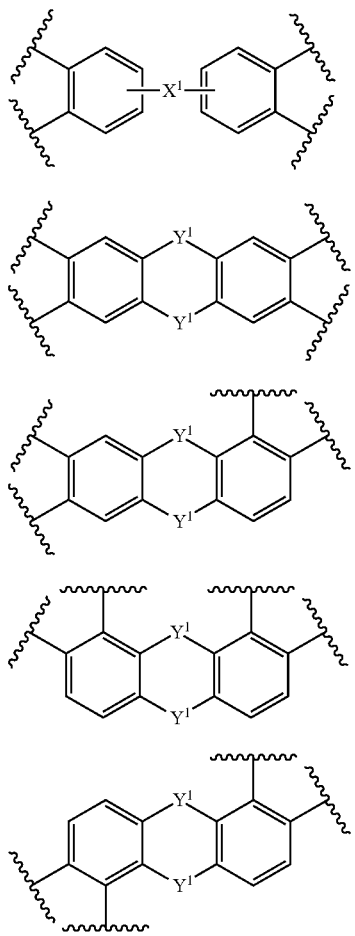

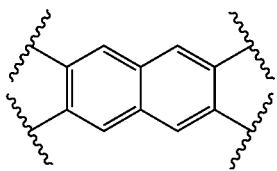
(c1-6)

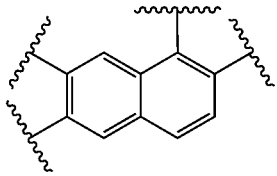
(c1-7)

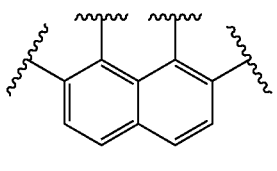
(c1-8)

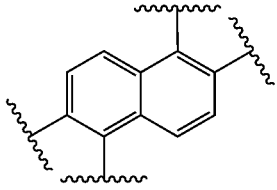
(c1-9)

(In the formula (c1-1), $X^1$ is one selected from the group consisting of an alkylene group having 1 to 10 carbon atoms, a fluorinated alkylene group having 1 to 10 carbon atoms, —O—, —S—, —SO—, —SO$_2$—, —CO—, —COO—, —CONH—, and a single bond. In the formulae (c1-2) to (c1-5), each $Y^1$ may be the same as or different from each other, and examples thereof include one selected from the group consisting of —CH$_2$—, —O—, —S—, —SO—, —SO$_2$—, —CO—, and a single bond.)

Each of the groups represented by the formulae (c1-1) to (c1-9) may have one or a plurality of substituents on the aromatic ring. As a suitable substituent, a fluorine atom, an alkyl group having 1 to 6 carbon atoms, an alkoxy group having 1 to 6 carbon atoms, a fluorinated alkyl group having 1 to 6 carbon atoms, or a fluorinated alkoxy group having 1 to 6 carbon atoms is preferable. In the case in which the substituent is a fluorinated alkyl group or a fluorinated alkoxy group, the substituent is preferably a perfluoroalkyl group or a perfluoroalkoxy group.

Specific examples of the compound represented by the formula (c2) include 2,4-diamino-1,5-benzenediol, 2,5-diamino-1,4-benzenediol, 2,5-diamino-3-fluoro-1,4-benzenediol, 2,5-diamino-3,6-difluoro-1,4-benzenediol, 2,6-diamino-1,5-dihydroxynaphthalene, 1,5-diamino-2,6-dihydroxynaphthalene, 2,6-diamino-3,7-dihydroxynaphthalene, 1,6-diamino-2,5-dihydroxynaphthalene, 4,4'-diamino-3,3'-dihydroxybiphenyl, 3,3'-diamino-4,4'-dihydroxybiphenyl, 2,3'-diamino-3,2'-dihydroxybiphenyl, 3,4'-diamino-4,3'-dihydroxybiphenyl, 4,4'-diamino-3,3'-dihydroxy-6,6'-ditrifluoromethylbiphenyl, 3,3'-diamino-4,4'-dihydroxy-6,6'-ditrifluoromethylbiphenyl, 2,3'-diamino-3,2'-dihydroxy-6,6'-ditrifluoromethylbiphenyl, 3,4'-diamino-4,3'-dihydroxy-6,6'-ditrifluoromethylbiphenyl, 4,4'-diamino-3,3'-dihydroxy-5,5'-ditrifluoromethylbiphenyl, 3,3'-diamino-4,4'-dihydroxy-5,5'-ditrifluoromethylbiphenyl, 2,3'-diamino- 3,2'-dihydroxy-5,5'-ditrifluoromethylbiphenyl, 3,4'-diamino-4,3'-dihydroxy-5,5'-ditrifluoromethylbiphenyl, bis(4-amino-3-hydroxyphenyl)methane, bis(3-amino-4-hydroxyphenyl)methane, 3,4'-diamino-4,3'-dihydroxydiphenylmethane, bis(4-amino-3-hydroxy-6-trifluoromethyl)methane, bis(3-amino-4-hydroxy-6-trifluoromethyl)methane, 3,4'-diamino-4,3'-dihydroxy-6,6'-ditrifluoromethyldiphenylmethane, bis(4-amino-3-hydroxyphenyl)difluoromethane, bis(3-amino-4-hydroxyphenyl)difluoromethane, 3,4'-diamino-4,3'-dihydroxydiphenyldifluoromethane, bis(4-amino-3-hydroxy-6-trifluoromethylphenyl)difluoromethane, bis(3-amino-4-hydroxy-6-trifluoromethylphenyl)difluoromethane, 3,4'-diamino-4,3'-dihydroxy-6,6'-ditrifluoromethyldiphenyldifluoromethane, bis(4-amino-3-hydroxyphenyl) ether, bis(3-amino-4-hydroxyphenyl) ether, 3,4'-diamino-4,3'-dihydroxydiphenyl ether, bis(4-amino-3-hydroxy-6-trifluoromethylphenyl) ether, bis(3-amino-4-hydroxy-6-trifluoromethylphenyl) ether, 3,4'-diamino-4,3'-dihydroxy-6,6'-ditrifluoromethyldiphenyl ether, bis(4-amino-3-hydroxyphenyl) ketone, bis(3-amino-4-hydroxyphenyl) ketone, 3,4'-diamino-4,3'-dihydroxydiphenyl ketone, bis(4-amino-3-hydroxy-6-trifluoromethyl) ketone, bis(3-amino-4-hydroxy-6-trifluoromethyl) ketone, 3,4'-diamino-4,3'-dihydroxy-6,6'-ditrifluoromethyldiphenyl ketone, 2,2-bis(4-amino-3-hydroxyphenyl)propane, 2,2-bis(3-amino-4-hydroxyphenyl)propane, 2-(3-amino-4-hydroxyphenyl)-2-(4'-amino-3'-hydroxyphenyl)propane, 2,2-bis(4-amino-3-hydroxy-6-trifluoromethylphenyl)propane, 2,2-bis(3-amino-4-hydroxy-6-trifluoromethylphenyl)propane, 2-(3-amino-4-hydroxy-6-trifluoromethylphenyl)-2-(4'-amino-3'-hydroxy-6'-trifluoromethylphenyl)propane, 2,2-bis(3-amino-4-hydroxy-5-trifluoromethylphenyl)propane, 2,2-bis(4-amino-3-hydroxyphenyl)hexafluoropropane, 2,2-bis(3-amino-4-hydroxyphenyl)hexafluoropropane, 2-(3-amino-4-hydroxyphenyl)-2-(4'-amino-3'-hydroxyphenyl)hexafluoropropane, 2,2-bis(4-amino-3-hydroxy-6-trifluoromethylphenyl)hexafluoropropane, 2,2-bis(3-amino-4-hydroxy-6-trifluoromethylphenyl)hexafluoropropane, 2-(3-amino-4-hydroxy-6-trifluoromethylphenyl)-2-(4'-amino-3'-hydroxy-6'-trifluoromethylphenyl)hexafluoropropane, 2,2-bis(3-amino-4-hydroxy-5-trifluoromethylphenyl)hexafluoropropane, bis(4-amino-3-hydroxyphenyl)sulfone, bis(3-amino-4-hydroxyphenyl)sulfone, 3,4'-diamino-4,3'-dihydroxydiphenyl sulfone, bis(4-amino-3-hydroxy-6-trifluoromethyl)sulfone, bis(3-amino-4-hydroxy-6-trifluoromethyl)sulfone, 3,4'-diamino-4,3'-dihydroxy-6,6'-ditrifluoromethyldiphenyl sulfone, bis(4-amino-3-hydroxyphenyl) sulfide, bis(3-amino-4-hydroxyphenyl) sulfide, 3,4'-diamino-4,3'-dihydroxydiphenyl sulfide, bis(4-amino-3-hydroxy-6-trifluoromethyl) sulfide, bis(3-amino-4-hydroxy-6-trifluoromethyl) sulfide, 3,4'-diamino-4,3'-dihydroxy-6,6'-ditrifluoromethyldiphenyl sulfide, (4-amino-3-hydroxyphenyl) 4-amino-3-hydroxyphenyl benzoate, (3-amino-4-hydroxyphenyl) 3-amino 4-hydroxyphenyl benzoate, (3-amino-4-hydroxyphenyl) 4-amino-3-hydroxyphenyl benzoate, (4-amino-3-hydroxyphenyl) 3-amino-4-hydroxyphenyl benzoate, N-(4-amino-3-hydroxyphenyl) 4-amino-3-hydroxy benzamide, N-(3-amino-4-hydroxyphenyl) 3-amino 4-hydroxyphenyl benzamide, N-(3-amino-4-hydroxyphenyl) 4-amino-3-hydroxyphenyl benzamide, N-(4-amino-3-hydroxyphenyl) 3-amino-4-hydroxyphenyl benzamide, 2,4'-bis(4-amino-3-hydroxyphenoxy)biphenyl, 2,4'-bis(3-amino-4-hydroxyphenoxy)biphenyl, 4,4'-bis(4-amino-3-hydroxyphenoxy)biphenyl, 4,4'-bis(3-amino-4-hydroxyphenoxy)biphenyl, di[4-(4-amino-3-hydroxyphenoxy)phenyl] ether, di[4-(3-amino-4-hydroxyphenoxy)phenyl] ether, 2,4'-bis(4-amino-3-hydroxyphenoxy)benzophenone, 2,4'-bis(3-amino-4-hydroxyphenoxy)benzophenone, 4,4'-bis(4-amino-3-hydroxyphenoxy)benzophenone, 4,4'-bis(3-amino-4-hydroxyphenoxy)benzophenone, 2,4'-bis(4-amino-3-hydroxyphenoxy)octafluorobiphenyl, 2,4'-bis(3-amino-4-hydroxyphenoxy)octafluorobiphenyl, 4,4'-bis(4-amino-3-hydroxyphenoxy)octafluorobiphenyl, 4,4'-bis(3-amino-4-hydroxyphenoxy)octafluorobiphenyl, 2,4'-bis(4-amino-3-hydroxyphenoxy)octafluorobenzophenone, 2,4'-bis(3-amino-4-hydroxyphenoxy)octafluorobenzophenone, 4,4'-bis(4-amino-3-hydroxyphenoxy)octafluorobenzophenone, 4,4'-bis(3-amino-4-hydroxyphenoxy)octafluorobenzophenone, 2,2-bis[4-(4-amino-3-hydroxyphenoxy)phenyl]propane, 2,2-bis[4-(3-amino-4-hydroxyphenoxy)phenyl]propane, 2,2-bis[4-(4-amino-3-hydroxyphenoxy)phenyl]hexafluoropropane, 2,2-bis[4-(3-amino-4-hydroxyphenoxy)phenyl]hexafluoropropane, 2,8-diamino-3,7-dihydroxydibenzofuran, 2,8-diamino-3,7-dihydroxyfluorene, 2,6-diamino-3,7-dihydroxyxanthene, 9,9-bis-(4-amino-3-hydroxyphenyl)fluorene, and 9,9-bis-(3-amino-4-hydroxyphenyl)fluorene.

Among these, 4,4'-diamino-3,3'-dihydroxybiphenyl and 2,2-bis(3-amino-4-hydroxyphenyl)hexafluoropropane are preferable.

Dicarbonyl Compound

As a raw material for use in synthesis of the polybenzoxazole precursor, the aromatic diamine diol described above as well as a dicarbonyl compound represented by the following formula (c3) are used. By condensation of the aromatic diamine diol described above and a dicarbonyl compound represented by the following formula (c3), a polybenzoxazole precursor is obtained.

[Chem. 19]

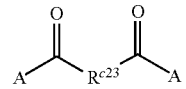

(c3)

(In the formula (c3), $R^{c23}$ is a divalent organic group; and A represents a hydrogen atom or a halogen atom.)

$R^{c23}$ in the formula (c3) may be an aromatic group, an aliphatic group, or a group consisting of a combination of an aromatic group and an aliphatic group. From the viewpoint that the resulting polybenzoxazole resin is excellent in heat resistance, mechanical properties, chemical resistance, and the like, $R^{c23}$ is preferably a group containing an aromatic group and/or an alicyclic group. The aromatic group in $R^{c23}$ may be an aromatic hydrocarbon group or an aromatic heterocyclic group.

$R^{c23}$ may contain a halogen atom, an oxygen atom, and/or a sulfur atom in addition to a carbon atom and a hydrogen atom. In the case in which $R^{c23}$ contains an oxygen atom, a nitrogen atom, or a sulfur atom, the oxygen atom, the nitrogen atom, or the sulfur atom may be contained in $R^{c23}$ in a form of a group selected from a nitrogen-containing heterocyclic group, —CONH—, —NH—, —N=N—, —CH=N—, —COO—, —O—, —CO—, —SO—, —SO$_2$—, —S—, and —S—S—, more preferably may be contained in $R^{c23}$ in a form of a group selected from —O—, —CO—, —SO—, —SO$_2$—, —S—, and —S—S—.

In the formula (c3), one of the two As may be a hydrogen atom and the other may be a halogen atom, and it is preferable that both of the two As are hydrogen atoms or both of the two As are halogen atoms. In the case in which A is a halogen atom, A is preferably chlorine, bromine, or iodine, more preferably chlorine.

In the case in which the dicarbonyl compound represented by the formula (c3) is a dialdehyde compound in which both of the two As are hydrogen atoms, a polybenzoxazole precursor represented by the following formula (C2) is produced.

[Chem. 20]

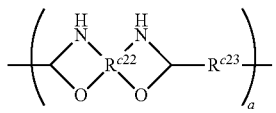

(C2)

(In the formula (C2), each of $R^{c22}$ and $R^{c23}$ is the same as those in the formula (c2) and the formula (c3); and a is the number of the repeating of a unit represented by the formula (C2).)

In the case in which the dicarbonyl compound represented by the formula (c3) is a dicarboxylic dihalide in which both of the two As are halogen atoms, a polybenzoxazole precursor represented by the following formula (C3) is produced.

[Chem. 21]

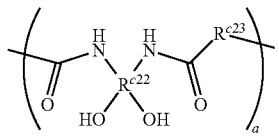

(C3)

(In the formula (C3), each of $R^{c22}$ and $R^{c23}$ is the same as those in the formula (c2) and the formula (c3); and a is the number of the repeating of a unit represented by the formula (C3).)

Next, the dialdehyde compound and the dicarboxylic dihalide, which are suitable as a dicarbonyl compound, are described.

Dialdehyde Compound

The dialdehyde compound used as a raw material of the polybenzoxazole precursor is a compound represented by the following formula (c2-1). The dialdehyde compound may be used either singly or in combination of two or more.

[Chem. 22]

(c2-1)

(In the formula (c2-1), $R^{c23}$ is the same as that in the formula (c3).)

Examples of an aromatic group or an aromatic-ring-containing group suitable as $R^{c23}$ in the formula (c2-1) include the following groups.

[Chem. 23]

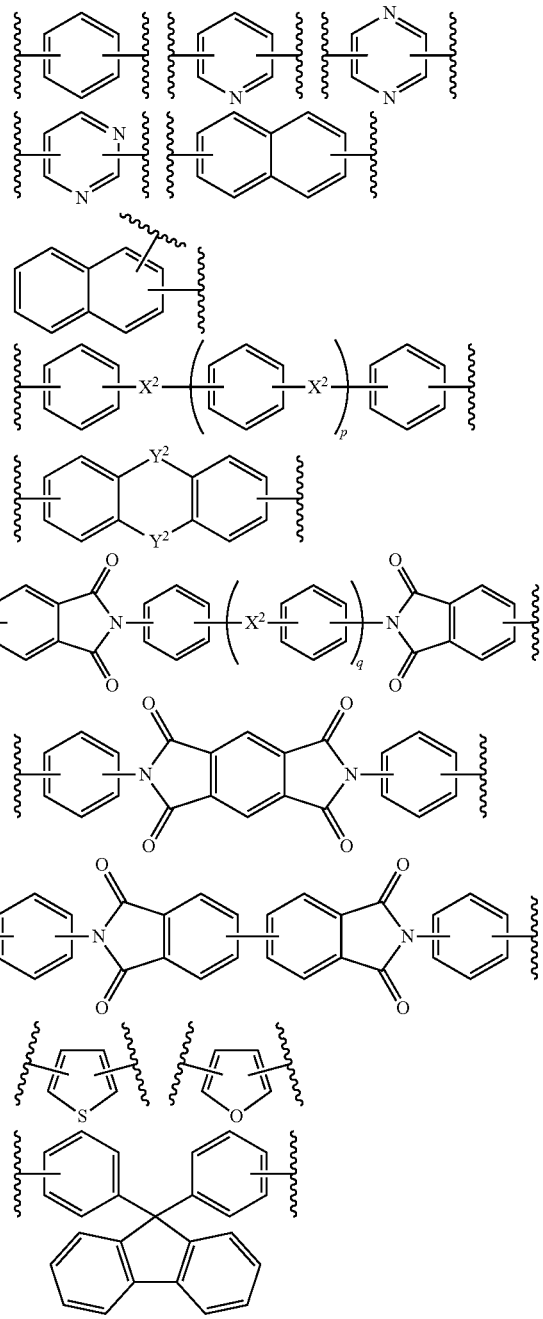

(In the formula, $X^2$ is one selected from the group consisting of an alkylene group having 1 to 10 carbon atoms, a fluorinated alkylene group having 1 to 10 carbon atoms, —O—, —S—, —SO—, —SO$_2$—, —CO—, —COO—, —CONH—, and a single bond; in the case in which a plurality of $X^2$s are contained, the plurality of $X^2$s may be the same as or different from each other; each $Y^2$ may be the same as or different from each other and is one selected from the group consisting of —CH$_2$—, —O—, —S—, —SO—, —SO$_2$—, —CO—, and a single bond; and each of p and q is an integer of 0 to 3.)

Examples of an alicyclic group or an alicyclic-ring-containing group suitable as $R^{c23}$ in the formula (c2-1) include the following groups.

[Chem. 24]

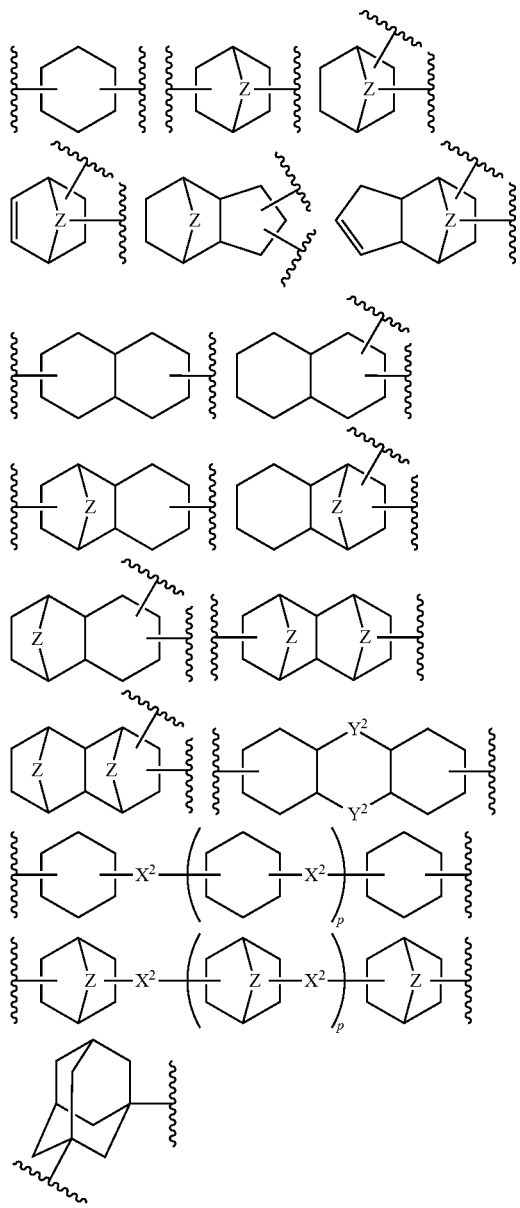

(In the formula, $X^2$ is one selected from the group consisting of an alkylene group having 1 to 10 carbon atoms, a fluorinated alkylene group having 1 to 10 carbon atoms, —O—, —S—, —SO—, —SO$_2$—, —CO—, —COO—, —CONH—, and a single bond; in the case in which a plurality of $X^2$s are contained, the plurality of $X^2$s may be the same as or different from each other; each $Y^2$ may be the same as or different from each other and is one selected from the group consisting of —CH$_2$—, —O—, —S—, —SO—, —SO$_2$—, —CO—, and a single bond; Z is one selected from the group consisting of —CH$_2$—, —CH$_2$CH$_2$—, and —CH=CH—; and each p is an integer of 0 to 3.)

An aromatic ring or an alicyclic ring contained in the above group suitable as $R^{c23}$ may have one or a plurality of substituents on the ring. A suitable and preferable substituent is a fluorine atom, an alkyl group having 1 to 6 carbon atoms, an alkoxy group having 1 to 6 carbon atoms, a fluorinated alkyl group having 1 to 6 carbon atoms, or a fluorinated alkoxy group having 1 to 6 carbon atoms. In the case in which the substituent is a fluorinated alkyl group or a fluorinated alkoxy group, the substituent is preferably a perfluoroalkyl group or a perfluoroalkoxy group.

In the case in which the dialdehyde compound represented by the formula (c2-1) is an aromatic dialdehyde, suitable examples thereof include benzenedialdehydes, pyridinedialdehydes, pyrazinedialdehydes, pyrimidinedialdehydes, naphthalenedialdehydes, biphenyldialdehydes, diphenyl ether dialdehydes, diphenyl sulfone dialdehydes, diphenyl sulfide dialdehydes, bis(formylphenoxy)benzenes, [1,4-phenylenebis(1-methylethylidene)]bisbenzaldehydes, 2,2-bis[4-(formylphenoxy)phenyl]propanes, bis[4-(formylphenoxy)phenyl]sulfides, bis[4-(formylphenoxy)phenyl]sulfones, and fluorene-containing dialdehydes.

Specific examples of the benzenedialdehydes include phthalaldehyde, isophthalaldehyde, terephthalaldehyde, 3-fluorophthalaldehyde, 4-fluorophthalaldehyde, 2-fluoroisophthalaldehyde, 4-fluoroisophthalaldehyde, 5-fluoroisophthalaldehyde, 2-fluoroterephthalaldehyde, 3-trifluoromethylphthalaldehyde, 4-trifluoromethylphthalaldehyde, 2-trifluoromethylisophthalaldehyde, 4-trifluoromethylisophthalaldehyde, 5-trifluoromethylisophthalaldehyde, 2-trifluoromethylterephthalaldehyde, 3,4,5,6-tetrafluorophthalaldehyde, 2,4,5,6-tetrafluoroisophthalaldehyde, and 2,3,5,6-tetrafluoroterephthalaldehyde.

Specific examples of the pyridinedialdehydes include pyridine-2,3-dialdehyde, pyridine-3,4-dialdehyde, and pyridine-3,5-dialdehyde. Specific examples of the pyrazinedialdehydes include pyrazine-2,3-dialdehyde, pyrazine-2,5-dialdehyde, and pyrazine-2,6-dialdehyde. Specific examples of the pyrimidinedialdehydes include pyrimidine-2,4-dialdehyde, pyrimidine-4,5-dialdehyde, and pyrimidine-4,6-dialdehyde.

Specific examples of the naphthalenedialdehydes include naphthalene-1,5-dialdehyde, naphthalene-1,6-dialdehyde, naphthalene-2,6-dialdehyde, naphthalene-3,7-dialdehyde, 2,3,4,6,7,8-hexafluoronaphthalene-1,5-dialdehyde, 2,3,4,5,6,8-hexafluoronaphthalene-1,6-dialdehyde, 1,3,4,5,7,8-hexafluoronaphthalene-2,6-dialdehyde, 1-trifluoromethylnaphthalene-2,6-dialdehyde, 1,5-bis(trifluoromethyl)naphthalene-2,6-dialdehyde, 1-trifluoromethylnaphthalene-3,7-dialdehyde, 1,5-bis(trifluoromethyl)naphthalene-3,7-dialdehyde, 1-trifluoromethyl-2,4,5,6,8-pentafluoronaphthalene-3,7-dialdehyde, 1-bis(trifluoromethyl)methoxy-2,4,5,6,8-pentafluoronaphthalene-3,7-dialdehyde, 1,5-bis(trifluoromethyl)-2,4,6,8-tetrafluoronaphthalene-3,7-dialdehyde, and 1,5-bis[bis(trifluoromethyl)methoxy]-2,4,6,8-tetrafluoronaphthalene-3,7-dialdehyde.

Specific examples of the biphenyldialdehydes include biphenyl-2,2'-dialdehyde, biphenyl-2,4'-dialdehyde, biphenyl-3,3'-dialdehyde, biphenyl-4,4'-dialdehyde, 6,6'-difluorobiphenyl-3,4'-dialdehyde, 6,6'-difluorobiphenyl-2,4'-dialdehyde, 6,6'-difluorobiphenyl-3,3'-dialdehyde, 6,6'-difluorobiphenyl-3,4'-dialdehyde, 6,6'-difluorobiphenyl-4,4'-dialdehyde, 6,6'-ditrifluoromethylbiphenyl-2,2'-dialdehyde, 6,6'-ditrifluoromethylbiphenyl-2,4'-dialdehyde, 6,6'-ditrifluoromethylbiphenyl-3,3'-dialdehyde, 6,6'-ditrifluoromethylbiphenyl-3,4'-dialdehyde, and 6,6'-ditrifluoromethylbiphenyl-4,4'-dialdehyde.

Specific examples of the diphenyl ether dialdehydes include diphenyl ether-2,4'-dialdehyde, diphenyl ether-3,3'-dialdehyde, diphenyl ether-3,4'-dialdehyde, and diphenyl ether-4,4'-dialdehyde.

Specific examples of the diphenyl sulfone dialdehydes include diphenyl sulfone-3,3'-dialdehyde, diphenyl sulfone-3,4'-dialdehyde, and diphenyl sulfone-4,4'-dialdehyde.

Specific examples of the diphenyl sulfide dialdehydes include diphenyl sulfide-3,3'-dialdehyde, diphenyl sulfide-3,4'-dialdehyde, and diphenyl sulfide-4,4'-dialdehyde.

Specific examples of the diphenyl ketone dialdehydes include diphenyl ketone-3,3'-dialdehyde, diphenyl ketone-3,4'-dialdehyde, and diphenyl ketone-4,4'-dialdehyde.

Specific examples of the bis(formylphenoxy)benzenes include benzene 1,3-bis(3-formylphenoxy)benzene, 1,4-bis(3-formylphenoxy)benzene, and 1,4-bis(4-formylphenoxy)benzene.

Specific examples of the [1,4-phenylenebis(1-methylethylidene)]bisbenzaldehydes include 3,3'-[1,4-phenylenebis(1-methylethylidene)]bisbenzaldehyde, 3,4'-[1,4-phenylenebis(1-methylethylidene)]bisbenzaldehyde, and 4,4'-[1,4-phenylenebis(1-methylethylidene)]bisbenzaldehyde.

Specific examples of the 2,2-bis[4-(formylphenoxy)phenyl]propanes include 2,2-bis[4-(2-formylphenoxy)phenyl]propane, 2,2-bis[4-(3-formylphenoxy)phenyl]propane, 2,2-bis[4-(4-formylphenoxy)phenyl]propane, 2,2-bis[4-(3-formylphenoxy)phenyl]hexafluoropropane, and 2,2-bis[4-(4-formylphenoxy)phenyl]hexafluoropropane.

Specific examples of the bis[4-(formylphenoxy)phenyl] sulfides include bis[4-(3-formylphenoxy)phenyl] sulfide and bis[4-(4-formylphenoxy)phenyl] sulfide.

Specific examples of the bis[4-(formylphenoxy)phenyl] sulfones include bis[4-(3-formylphenoxy)phenyl] sulfone and bis[4-(4-formylphenoxy)phenyl] sulfone.

Specific examples of the fluorene-containing dialdehydes include fluorene-2,6-dialdehyde, fluorene-2,7-dialdehyde, dibenzofuran-3,7-dialdehyde, 9,9-bis(4-formylphenyl)fluorene, 9,9-bis(3-formylphenyl)fluorene, and 9-(3-formylphenyl)-9-(4'-formylphenyl)fluorene.

A diphenylalkanedialdehyde or a diphenylfluoroalkanedialdehyde represented by the following formulae may also be suitable for use as the aromatic dialdehyde compound.

[Chem. 25]

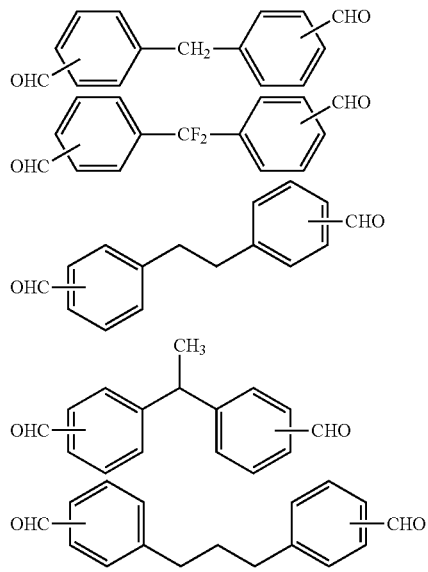

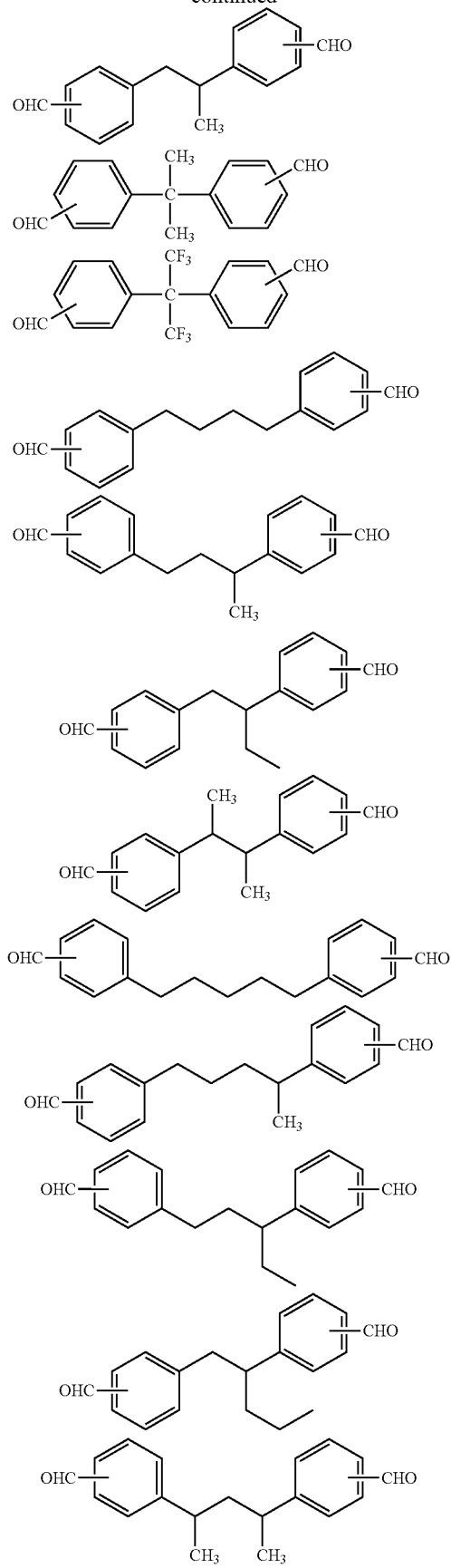

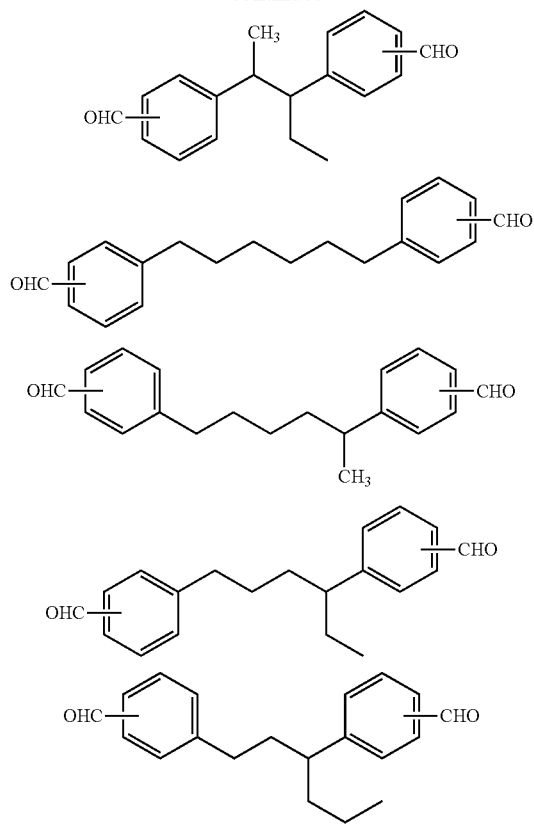

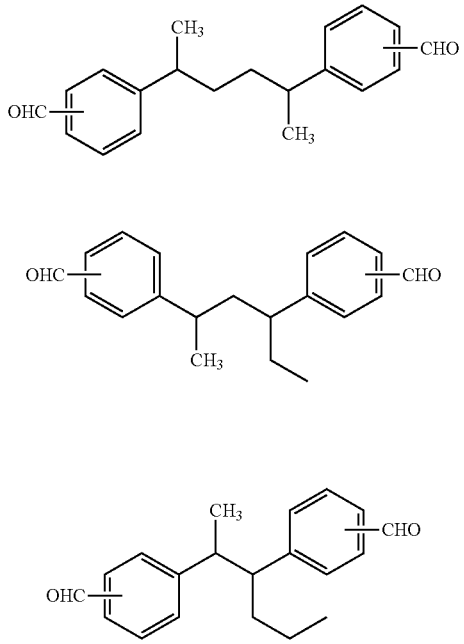

A compound having an imide bond represented by the following formulae may be suitable for use as the aromatic dialdehyde compound.

[Chem. 26]

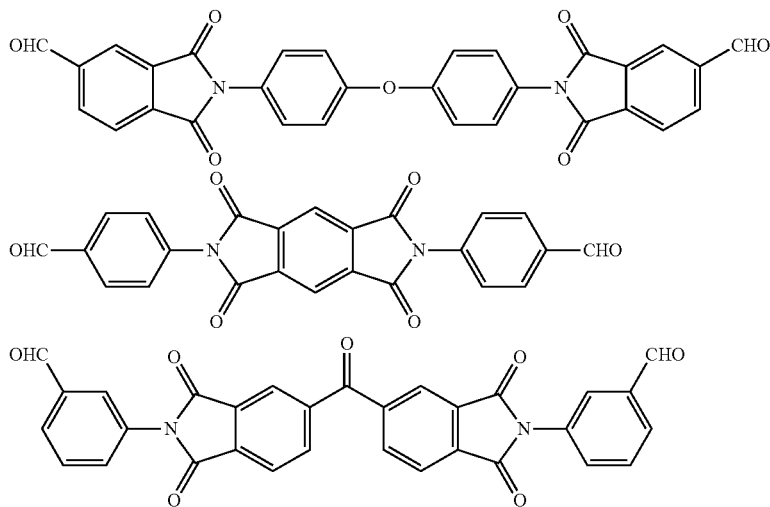

-continued

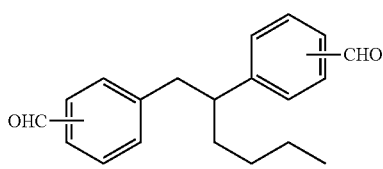

In the case in which the dicarbonyl compound represented by the formula (c2-1) is an alicyclic dialdehyde having an alicyclic group, suitable examples thereof include cyclohexane-1,4-dialdehyde, cyclohexane-1,3-dialdehyde, bicyclo[2.2.1]heptane-2,5-dialdehyde, bicyclo[2.2.2]octane-2,5-dialdehyde, bicyclo[2.2.2]oct-7-ene-2,5-dialdehyde, bicyclo[2.2.1]heptane-2,3-dialdehyde, bicyclo[2.2.1]hept-5-ene-2,3-dialdehyde, tricyclo[5.2.1.0$^{2,6}$]decane-3,4-dialdehyde, tricyclo[5.2.1.0$^{2,6}$]dec-4-ene-8,9-dialdehyde, perhydronaphthalene-2,3-dialdehyde, perhydronaphthalene-1,4- dialdehyde, perhydronaphthalene-1,6-dialdehyde, perhydro-1,4-methanonaphthalene-2,3-dialdehyde, perhydro-1,4-methanonaphthalene-2,7-dialdehyde, perhydro-1,4-methanonaphthalene-7,8-dialdehyde, perhydro-1,4:5,8-dimethanonaphthalene-2,3-dialdehyde, perhydro-1,4:5,8-dimethanonaphthalene-2,7-dialdehyde, perhydro-1,4:5,8:9,10-trimethanoanthracene-2,3-dialdehyde, bicyclohexyl-4,4'-dialdehyde, dicyclohexyl ether-3,4'-dialdehyde, dicyclohexylmethane-3,3'-dialdehyde, dicyclohexylmethane-3,4'-dialdehyde, dicyclohexylmethane-4,4'-dialdehyde, dicyclohexyldifluoromethane-3,3'-dialdehyde, dicyclohexyldifluoromethane-3,4'-dialdehyde, dicyclohexyldifluoromethane-4,4'-dialdehyde, dicyclohexyl sulfone-3,3'-dialdehyde, dicyclohexyl sulfone-3,4'-dialdehyde, dicyclohexyl sulfone-4,4'-dialdehyde, dicyclohexyl sulfide-3,3'-dialdehyde, dicyclohexyl sulfide-3,4'-dialdehyde, dicyclohexyl sulfide-4,4'-dialdehyde, dicyclohexyl ketone-3,3'-dialdehyde, dicyclohexyl ketone-3,4'-dialdehyde, dicyclohexyl ketone-4,4'-dialdehyde, 2,2-bis(3-formylcyclohexyl)propane, 2,2-bis(4-formylcyclohexyl)propane, 2,2-bis(3-formylcyclohexyl)hexafluoropropane, 2,2-bis(4-formylcyclohexyl)hexafluoropropane, 1,3-bis(3-formylcyclohexyl)benzene, 1,4-bis(3-formylcyclohexyl)benzene, 1,4-bis(4-formylcyclohexyl)benzene, 3,3'-[1,4-cyclohexylenebis(1-methylethylidene)]biscyclohexane carbaldehyde, 3,4'-[1,4-cyclohexylenebis(1-methylethylidene)]biscyclohexane carbaldehyde, 4,4'-[1,4-cyclohexylenebis(1-methylethylidene)]biscyclohexane carbaldehyde, 2,2-bis[4-(3-formylcyclohexyl)cyclohexyl]propane, 2,2-bis[4-(4-formylcyclohexyl)cyclohexyl]propane, 2,2-bis[4-(3-formylcyclohexyl)cyclohexyl]hexafluoropropane, 2,2-bis[4-(4-formylphenoxy)cyclohexyl]hexafluoropropane, bis[4-(3-formylcyclohexyloxy)cyclohexyl] sulfide, bis[4-(4-formylcyclohexyloxy)cyclohexyl] sulfide, bis[4-(3-formylcyclohexyloxy)cyclohexyl] sulfone, bis[4-(4-formylcyclohexyloxy)cyclohexyl] sulfone, 2,2'-bicyclo[2.2.1]heptane-5,6'-dialdehyde, 2,2'-bicyclo[2.2.1]heptane-6,6'-dialdehyde, and 1,3-diformyladamantane.

Among these dialdehyde compounds described above, isophthalaldehyde is preferable because it is easily synthesized and readily available and also tends to give a polybenzoxazole precursor that is capable of yielding a polybenzoxazole resin excellent in heat resistance and mechanical characteristics.

Dicarboxylic Dihalide

A dicarboxylic dihalide used as a raw material of the polybenzoxazole precursor is a compound represented by the following formula (c2-2). The dicarboxylic dihalide may be used either singly or in combination of two or more.

[Chem. 27]

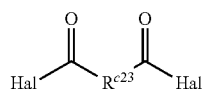

(c2-2)

(In the formula (c2-2), $R^{c23}$ is the same as that in the formula (c3); and Hal is a halogen atom.)

In the formula (c2-2), Hal is preferably chlorine, bromine, and iodine, more preferably chlorine.

Examples of a compound suitable as a compound represented by the formula (c2-2) include a compound obtained by substituting two aldehyde groups of the compound described above suitable as the dialdehyde compound with halocarbonyl groups, preferably with chlorocarbonyl groups.

Among the dicarboxylic dihalides described above, terephthaloyl dichloride is preferable because it is easily synthesized and readily available and also tends to give a polybenzoxazole precursor that is capable of yielding a polybenzoxazole resin excellent in heat resistance and mechanical characteristics.

Solvent

The solvent used for preparation of the polybenzoxazole precursor is not particularly limited and may be selected as appropriate from solvents conventionally used for preparation of a polybenzoxazole precursor. The solvent used for preparation of the polybenzoxazole precursor is preferably a solvent that contains a compound represented by the following formula (c4).

[Chem. 28]

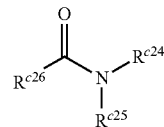

(c4)

(In the formula (c4), $R^{c24}$ and $R^{c25}$ are each independently an alkyl group having 1 to 3 carbon atoms; and $R^{c26}$ is a group represented by the following formula (c4-1) or the following formula (c4-2).

[Chem. 29]

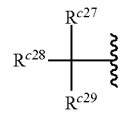

(c4-1)

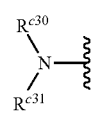

(c4-2)

In the formula (c4-1), $R^{c27}$ is a hydrogen atom or a hydroxy group, and $R^{c28}$ and $R^{c29}$ are each independently an alkyl group having 1 to 3 carbon atoms. In the formula (c4-2), $R^{c30}$ and $R^{c31}$ are each independently a hydrogen atom or an alkyl group having 1 to 3 carbon atoms.)

In the case in which the polybenzoxazole precursor is synthesized by using a solvent that contains a compound represented by the formula (c4), discoloration of the resin and the resulting decrease in transparency of the resin may be inhibited from occurring when the polybenzoxazole precursor is heated at low temperature and the resulting polybenzoxazole resin may be excellent in mechanical properties such as tensile elongation as well as in chemical resistance.

In the case in which the polybenzoxazole resin is produced by heating the polybenzoxazole precursor synthesized by using a solvent that contains a compound represented by the formula (c4), a surface defect of the polybenzoxazole resin such as swelling, cracks, and foaming may be inhibited. For this reason, by producing a polybenzoxazole resin film by heating a film that contains the polybenzoxazole precursor synthesized by using a solvent that contains a compound represented by the formula (c4), the resulting film tends to be excellent in appearance free of defects such as cracks, blistering, or pinholes.

Specific examples of the compound represented by the formula (c4) in which $R^{c26}$ is a group represented by the formula (c4-1) include N,N,2-trimethylpropionamide, N-ethyl,N,2-dimethylpropionamide, N,N-diethyl-2-methylpropionamide, N,N,2-trimethyl-2-hydroxypropionamide, N-ethyl-N,2-dimethyl-2-hydroxypropionamide, and N,N-diethyl-2-hydroxy-2-methylpropionamide.

Specific examples of the compound represented by the formula (c4) in which $R^{c26}$ is a group represented by the formula (c4-2) include N,N,N',N'-tetramethylurea and N,N,N',N'-tetraethylurea.

Among the compounds represented by the formula (c4), N,N,2-trimethylpropionamide and N,N,N',N'-tetramethylurea are particularly preferable. N,N,2-trimethylpropionamide has a boiling point under atmospheric pressure of 175° C., and N,N,N',N'-tetramethylurea has a boiling point under atmospheric pressure of 177° C. In this way, each of N,N,2-trimethylpropionamide and N,N,N',N'-tetramethylurea has a relatively low boiling point among other solvents that are capable of dissolving the aromatic diamine diol, the dicarbonyl compound, and the resulting polybenzoxazole precursor. Therefore, in the case in which a polybenzoxazole resin is formed by using the polybenzoxazole precursor synthesized by using a solvent that contains at least one type selected from N,N,2-trimethylpropionamide and N,N,N',N'-tetramethylurea, a solvent tends not to remain in the resulting polybenzoxazole resin while the polybenzoxazole precursor is heated and thereby the resulting polybenzoxazole resin tends not to have a decrease in tensile elongation.

Furthermore, both of N,N,2-trimethylpropionamide and N,N,N',N'-tetramethylurea have low hazard potential, as is obvious from the fact that neither of these substances is listed as an SVHC (Substance of Very High Concern) which is considered as a hazardous substance under the EU (the European Union) REACH Regulation. This is another reason that these substances are useful.

In the case in which the solvent used for preparation of the polybenzoxazole precursor contains a compound represented by the formula (c4), the content of the compound represented by the formula (c4) in the solvent is preferably 70% by mass or more, more preferably 80% by mass or more, particularly preferably 90% by mass or more, most preferably 100% by mass.

In the case in which the solvent contains a compound represented by the formula (c4), examples of an organic solvent that may be used together with a compound represented by the formula (c4) include nitrogen-containing polar solvents such as N,N-dimethylformamide, N,N-dimethylacetamide, N-methyl-2-pyrrolidone, hexamethylphosphoramide, and 1,3-dimethyl-2-imidazolidinone; ketones such as methyl ethyl ketone, methyl isobutyl ketone, cyclohexanone, and isophorone; esters such as γ-butyrolactone, γ-valerolactone, δ-valerolactone, γ-caprolactone, ε-caprolactone, α-methyl-γ-butyrolactone, ethyl lactate, methyl acetate, ethyl acetate, and n-butyl acetate; cyclic ethers such as dioxane and tetrahydrofuran; cyclic esters such as ethylene carbonate and propylene carbonate; aromatic hydrocarbons such as toluene and xylene; and sulfoxides such as dimethyl sulfoxide.

Method for Producing Polybenzoxazole Precursor

The polybenzoxazole precursor is produced by subjecting the aromatic diamine diol described above and the dicarbonyl compound to reaction in a solvent by a well-known method. Next, a typical method for producing a polybenzoxazole precursor is described, in which the dicarbonyl compound is a dialdehyde compound or the dicarbonyl compound is a dicarboxylic halide.

Reaction between the aromatic diamine diol and the dialdehyde compound is Schiff base formation reaction and may be allowed to proceed by a well-known method. The reaction temperature is not particularly limited but typically, it is preferably 20 to 200° C., more preferably 20 to 160° C., particularly preferably 100 to 160° C.

The reaction between the aromatic diamine diol and the dialdehyde compound may be allowed to proceed while reflux and dehydration are being conducted with the addition of an entrainer to the solvent. The entrainer is not particularly limited and is selected as appropriate from any organic solvent that is capable of forming an azeotrope with water and forming a two-phase system with water at room temperature. Examples of a suitable entrainer include esters such as isobutyl acetate, allyl acetate, n-propyl propionate, isopropyl propionate, n-butyl propionate, and isobutyl propionate; ethers such as dichloromethyl ether and ethylisoamyl ether; ketones such as ethylpropyl ketone; and aromatic hydrocarbons such as toluene.

The time of reaction between the aromatic diamine diol and the dialdehyde compound is not particularly limited but typically, it is preferable that the time be about 2 to 72 hours.

The amount of the dialdehyde compound used for production of the polybenzoxazole precursor is preferably 0.5 to 1.5 mol, more preferably 0.7 to 1.3 mol with respect to 1 mol of the aromatic diamine diol.

The amount of the solvent used is not particularly limited as long as the reaction between the aromatic diamine diol and the dialdehyde compound proceeds well. Typically, the mass of the solvent used is 1 to 40 times, preferably 1.5 to 20 times the total mass of the aromatic diamine diol and the dialdehyde compound.

It is preferable that the reaction between the aromatic diamine diol and the dialdehyde compound be allowed to proceed until the number average molecular weight of the polybenzoxazole precursor thus produced reaches 1000 to 20000, preferably 1200 to 5000.

The temperature for the reaction between the aromatic diamine diol and the dicarboxylic dihalide is not particularly limited but typically, it is preferable that the temperature be −20 to 150° C., more preferably −10 to 150° C., particularly preferably −5 to 70° C. The reaction between the aromatic diamine diol and the dicarboxylic dihalide generates a hydrogen halide as a by-product. So as to neutralize the hydrogen halide, a small amount of an organic base such as triethylamine, pyridine, or N,N-dimethyl-4-aminopyridine or an alkali metal hydroxide such as sodium hydroxide or potassium hydroxide may be added to the reaction fluid.

The time for the reaction between the aromatic diamine diol and the dicarboxylic dihalide is not particularly limited and typically, it is preferable that the time be about 2 to 72 hours.

The amount of the dicarboxylic dihalide used for production of the polybenzoxazole precursor is preferably 0.5 to 1.5 mol, more preferably 0.7 to 1.3 mol with respect to 1 mol of the aromatic diamine diol.

The amount of the solvent used is not particularly limited as long as the reaction between the aromatic diamine diol and the dicarboxylic dihalide proceeds well. Typically, the mass of the solvent is 1 to 40 times, preferably 1.5 to 20 times the total mass of the aromatic diamine diol and the dicarboxylic dihalide.

It is preferable that the reaction between the aromatic diamine diol and the dicarboxylic dihalide be allowed to proceed until the number average molecular weight of the polybenzoxazole precursor thus produced reaches 1000 to 20000, preferably 1200 to 5000.

By the method described above, a solution of the polybenzoxazole precursor is obtained. This solution of the polybenzoxazole precursor may be used as it is for blending the polybenzoxazole precursor with the composition according to the present invention. Alternatively, the solvent may be at least partially removed from the solution of the polybenzoxazole precursor under reduced pressure at a low temperature at which the polybenzoxazole precursor does not become converted into a polybenzoxazole resin, and the resulting paste or solid of the polybenzoxazole precursor may be used for the preparation of the composition.

(Polybenzothiazole Precursor)

The polybenzothiazole precursor is typically produced by reaction of an aromatic diaminedithiol and a dicarbonyl compound having a specific structure. As the aromatic diaminedithiol, a compound that is obtained by substituting a hydroxy group of the aromatic diamine diol used for synthesis of the polybenzoxazole precursor with a mercapto group may be used. As the dicarbonyl compound, the same compound as that used in the synthesis of the polybenzoxazole precursor may be used.

The reaction method, reaction conditions, and the like for synthesizing the polybenzothiazole precursor by reaction between the aromatic diaminedithiol and the dicarbonyl compound are the same as those in the synthesis of the polybenzoxazole precursor by reaction between the aromatic diamine diol and the dicarbonyl compound.

(Polybenzimidazole Precursor)

The polybenzimidazole precursor is typically produced by reaction of an aromatic tetraamine and a dicarboxylic dihalide. As the aromatic tetraamine, a compound that is obtained by substituting a hydroxy group of the aromatic diamine diol used for synthesis of the polybenzoxazole precursor with an amino group may be used. As the dicarboxylic dihalide, the same compound as that used in the synthesis of the polybenzoxazole precursor may be used.

The reaction method, reaction conditions, and the like for synthesizing the polybenzimidazole precursor by reaction between the aromatic tetraamine and the dicarboxylic dihalide are the same as those in the synthesis of the polybenzoxazole precursor by reaction between the aromatic diamine diol and the dicarboxylic dihalide.

(Styrene-(Maleic Acid) Copolymer)

The type of the styrene-(maleic acid) copolymer is not particularly limited as long as the object of the present invention is not impaired. The ratio (mass ratio) of styrene to maleic acid in the styrene-(maleic acid) copolymer is preferably 1/9 to 9/1, more preferably 2/8 to 8/1, particularly preferably 1/1 to 8/1. The molecular weight of the styrene-(maleic acid) copolymer is not particularly limited but is preferably 1000 to 100000, more preferably 5000 to 12000 in terms of the mass average molecular weight of polystyrene.

(Epoxy-Group-Containing Resin)

The epoxy-group-containing resin may be a polymer that is obtained by polymerizing a monomer having an epoxy group or a monomer mixture containing a monomer having an epoxy group. The epoxy-group-containing resin may be obtained by introducing an epoxy group into a polymer having a functional reactive group such as a hydroxy group, a carboxy group, or an amino group by using, for example, a compound having an epoxy group such as epichlorohydrin. As the polymer having an epoxy group, a polymer that is obtained by polymerizing a monomer having an epoxy group or a monomer mixture containing a monomer having an epoxy group is preferable because use of this polymer is advantageous in terms of, for example, availability, easy preparation, and easy adjustment of the amount of epoxy groups in the polymer.

Examples of a preferable epoxy-group-containing resin include novolac epoxy resins such as a phenol novolac type epoxy resin, a brominated phenol novolac type epoxy resin, an orthocresol novolac type epoxy resin, a bisphenol A novolac type epoxy resin, and a bisphenol AD novolac type epoxy resin; cyclic aliphatic epoxy resins such as an epoxidized product of a dicyclopentadiene type phenolic resin; and aromatic epoxy resins such as an epoxidized product of a naphthalene type phenolic resin.

Among the epoxy-group-containing resins, the polymer having an epoxy group is preferably a homopolymer of a (meth)acrylic acid ester having an epoxy group, or a copolymer of a (meth)acrylic acid ester having an epoxy group with the other monomer in view of ease of preparation and the like.

The (meth)acrylic acid ester having an epoxy group may be either a (meth)acrylic acid ester having a chain aliphatic epoxy group, or the below-mentioned (meth)acrylic acid ester having an alicyclic epoxy group. The (meth)acrylic acid ester having an epoxy group may have an aromatic group. The (meth)acrylic acid ester having an epoxy group is preferably an aliphatic (meth)acrylic acid ester having a chain aliphatic epoxy group or an aliphatic (meth)acrylic acid ester having an alicyclic epoxy group, and more preferably an aliphatic (meth)acrylic acid ester having an alicyclic epoxy group.

Examples of the (meth)acrylic acid ester, which has an aromatic group and an epoxy group, include 4-glycidyloxyphenyl (meth)acrylate, 3-glycidyloxyphenyl (meth)acrylate, 2-glycidyloxyphenyl (meth)acrylate, 4-glycidyloxyphenylmethyl (meth)acrylate, 3-glycidyloxyphenylmethyl (meth)acrylate, and 2-glycidyloxyphenylmethyl (meth)acrylate.

Examples of the aliphatic (meth)acrylic acid ester having a chain aliphatic epoxy group include (meth)acrylic acid esters in which a chain aliphatic epoxy group is combined with an oxy group (—O—) in an ester group (—O—CO—), such as epoxyalkyl (meth)acrylate and epoxyalkyloxyalkyl (meth)acrylate. Such a chain aliphatic epoxy group possessed by the (meth)acrylic acid ester may have one or a plurality of oxy groups (—O—) in a chain. The number of carbon atoms of the chain aliphatic epoxy group is not particularly limited, and is preferably 3 to 20, more preferably 3 to 15, and particularly preferably 3 to 10.

Specific examples of the aliphatic (meth)acrylic acid ester having a chain aliphatic epoxy group include epoxyalkyl (meth)acrylates such as glycidyl (meth)acrylate, 2-methyl glycidyl (meth)acrylate, 3,4-epoxybutyl (meth)acrylate, and 6,7-epoxyheptyl (meth)acrylate; and epoxyalkyloxyalkyl (meth)acrylates such as 2-glycidyloxyethyl (meth)acrylate, 3-glycidyloxy-n-propyl (meth)acrylate, 4-glycidyloxy-n-butyl (meth)acrylate, 5-glycidyloxy-n-hexyl (meth)acrylate, and 6-glycidyloxy-n-hexyl (meth)acrylate.

Specific examples of the aliphatic (meth)acrylic acid ester having an alicyclic epoxy group include compounds represented by the following formulae (c5-1) to (c5-15). Of these compounds, compounds represented by the following formulae (c5-1) to (c5-5) are preferable, and compounds represented by the following formulae (c5-1) to (c5-3) are more preferable.

[Chem. 30]
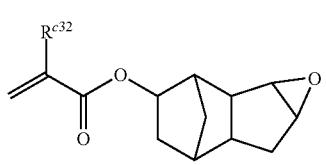 (c5-1)
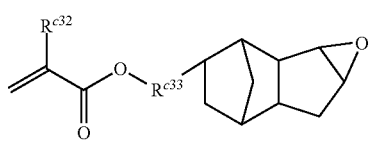 (c5-2)
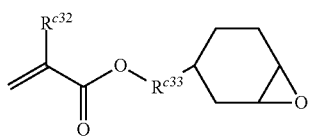 (c5-3)
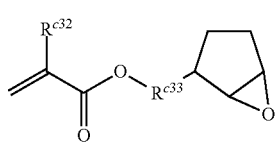 (c5-4)
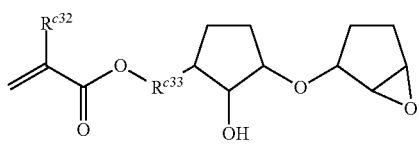 (c5-5)
[Chem. 31]
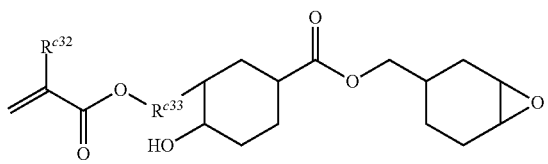 (c5-6)
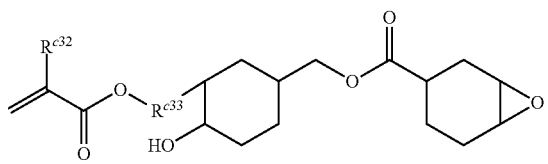 (c5-7)
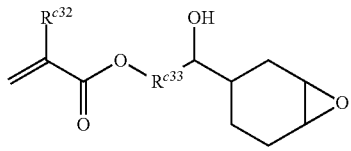 (c5-8)
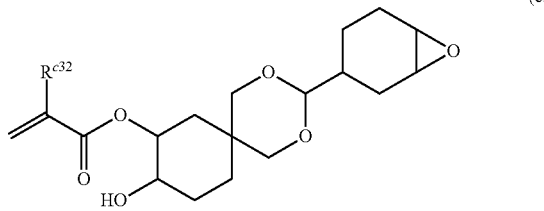 (c5-9)
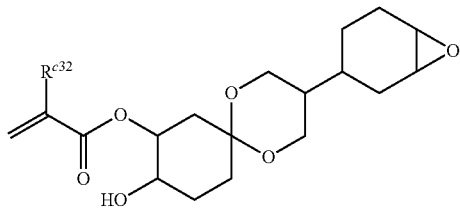 (c5-10)
[Chem. 32]
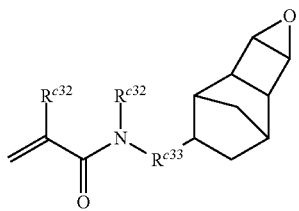 (c5-11)
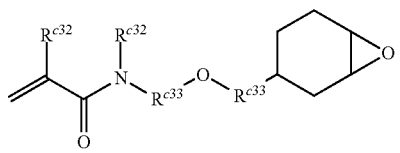 (c5-12)
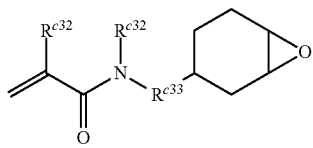 (c5-13)

-continued

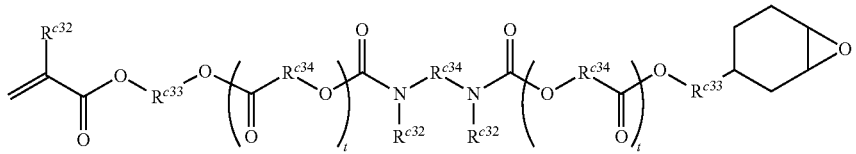
(c5-14)

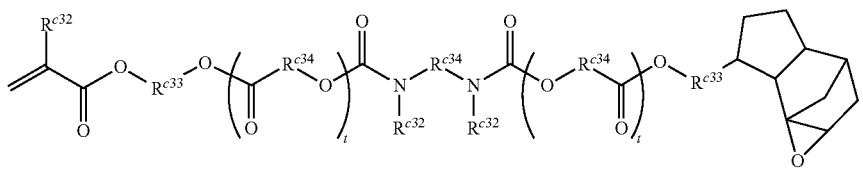
(c5-15)

In the above formulae, $R^{c32}$ represents a hydrogen atom or a methyl group; $R^{c33}$ represents a divalent aliphatic saturated divalent hydrocarbon group having 1 to 10 carbon atoms; and t represents an integer of 0 to 10. $R^{c33}$ is a linear or branched alkylene group and is preferably, for example, a methylene group, an ethylene group, a propylene group, a tetramethylene group, an ethylethylene group, a pentamethylene group, or a hexamethylene group. $R^{c34}$ is preferably, for example, a methylene group, an ethylene group, a propylene group, a tetramethylene group, an ethylethylene group, a pentamethylene group, a hexamethylene group, a phenylene group, or a cyclohexylene group.

It is possible to use, as the polymer having an epoxy group, both of a homopolymer of a (meth)acrylic acid ester having an epoxy group, and a copolymer of a (meth)acrylic acid ester having an epoxy group with the other monomer. The content of a unit derived from the (meth)acrylic acid ester having an epoxy group in the polymer having an epoxy group is preferably 70% by mass or more, more preferably 80% by mass or more, particularly preferably 90% by mass or more, and most preferably 100% by mass.

When the polymer having an epoxy group is a copolymer of the (meth)acrylic acid ester having an epoxy group with the other monomer, examples of the other monomer include an unsaturated carboxylic acid, a (meth)acrylic acid ester having no epoxy group, (meth)acrylamides, an allyl compound, vinyl ethers, vinyl esters, styrenes, and the like. These compounds can be used singly, or two or more thereof can be used in combination. In view of storage stability of a composition, and chemical resistance of a shaped body formed using the composition against alkali, it is preferred that the copolymer of the (meth)acrylic acid ester having an epoxy group with the other monomer does not include a unit derived from an unsaturated carboxylic acid.

Examples of the unsaturated carboxylic acid include (meth)acrylic acid; (meth)acrylic acid amide; crotonic acid; maleic acid, fumaric acid, citraconic acid, mesaconic acid, itaconic acid, and anhydrides of these dicarboxylic acids.

Examples of the (meth)acrylic acid ester having no epoxy group include linear or branched alkyl (meth)acrylates such as methyl (meth)acrylate, ethyl (meth)acrylate, propyl (meth)acrylate, amyl (meth)acrylate, and t-octyl (meth)acrylate; chloroethyl (meth)acrylate, 2,2-dimethylhydroxypropyl (meth)acrylate, 2-hydroxyethyl (meth)acrylate, trimethylolpropane mono(meth)acrylate, benzyl (meth)acrylate, furfuryl (meth)acrylate; and a (meth)acrylic acid ester having a group with an alicyclic skeleton. Of (meth)acrylic acid esters having no epoxy group, a (meth)acrylic acid ester having a group with an alicyclic skeleton is preferable.

In a (meth)acrylic acid ester having a group with an alicyclic skeleton, an alicyclic group composing the alicyclic skeleton may be either monocyclic or polycyclic. Examples of the monocyclic alicyclic group include a cyclopentyl group, a cyclohexyl group, and the like. Examples of the polycyclic alicyclic group include a norbornyl group, an isobornyl group, a tricyclononyl group, a tricyclodecyl group, a tetracyclododecyl group, and the like.

Examples of the (meth)acrylic acid ester having a group with an alicyclic skeleton include compounds represented by the following formulae (c6-1) to (c6-8). Of these compounds, compounds represented by the following formulae (c6-3) to (c6-8) are preferable, and compounds represented by the following formulae (c6-3) or (c6-4) are more preferable.

[Chem. 33]

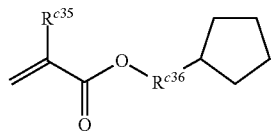
(c6-1)

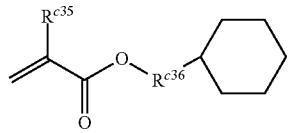
(c6-2)

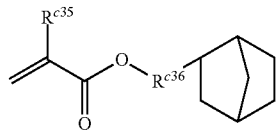
(c6-3)

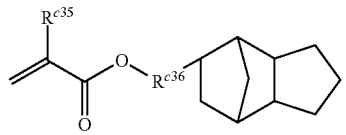
(c6-4)

[Chem. 34]

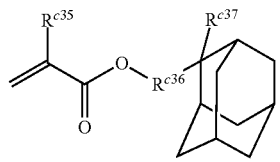
(c6-5)

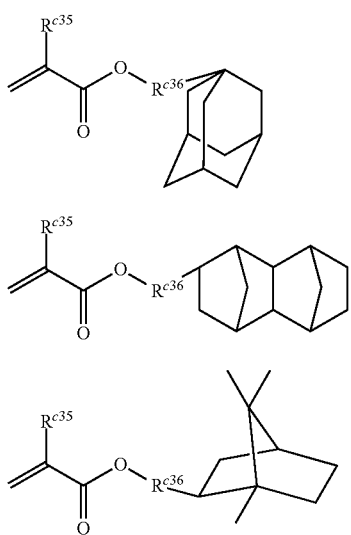

(c6-6)

(c6-7)

(c6-8)

In the above formulae, $R^{c35}$ represents a hydrogen atom or a methyl group; $R^{c36}$ represents a single bond or a divalent aliphatic saturated hydrocarbon group having 1 to 6 carbon atoms; and $R^{c37}$ represents a hydrogen atom or an alkyl group having 1 to 5 carbon atoms. $R^{c36}$ is preferably a single bond, or a linear or branched alkylene group, for example, a methylene group, an ethylene group, a propylene group, a tetramethylene group, an ethylethylene group, a pentamethylene group, or a hexamethylene group. $R^{c37}$ is preferably a methyl group or an ethyl group.

Examples of (meth)acrylamides include (meth)acrylamide, N-alkyl(meth)acrylamide, N-aryl(meth)acrylamide, N,N-dialkyl(meth)acrylamide, N,N-aryl(meth)acrylamide, N-methyl-N-phenyl(meth)acrylamide, N-hydroxyethyl-N-methyl(meth)acrylamide, and the like.

Examples of the allyl compound include allyl esters such as allyl acetate, allyl caproate, allyl caprylate, allyl laurate, allyl palmitate, allyl stearate, allyl benzoate, allyl acetoacetate, and allyl lactate; allyloxyethanol, and the like.

Examples of vinyl ethers include aliphatic vinyl ethers such as hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, and tetrahydrofurfuryl vinyl ether; vinylaryl ethers such as vinyl phenyl ether, vinyl tolyl ether, vinyl chlorophenyl ether, vinyl-2,4-dichlorophenyl ether, vinyl naphthyl ether, and vinyl anthranyl ether; and the like.

Examples of vinyl esters include vinyl butyrate, vinyl isobutyrate, vinyl trimethyl acetate, vinyl diethyl acetate, vinyl valerate, vinyl caproate, vinyl chloroacetate, vinyl dichloroacetate, vinyl methoxyacetate, vinyl butoxyacetate, vinyl phenylacetate, vinyl acetoacetate, vinyl lactate, vinyl-β-phenyl butyrate, vinyl benzoate, vinyl salicylate, vinyl chlorobenzoate, vinyl tetrachlorobenzoate, vinyl naphthoate, and the like.

Examples of styrenes include styrene; alkylstyrenes such as methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, and acetoxymethylstyrene; alkoxystyrenes such as methoxystyrene, 4-methoxy-3-methylstyrene, and dimethoxystyrene; halostyrenes such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, and 4-fluoro-3-trifluoromethylstyrene; and the like.

The molecular weight of the epoxy-group-containing resin is not particularly limited as long as the object of the present invention is not impaired, but the molecular weight is preferably 3,000 to 30,000, more preferably 5,000 to 15,000 in terms of the mass average molecular weight of polystyrene.

[Photocurable Low-Molecular Compound]

The composition may contain a photopolymerizable low-molecular compound (photopolymerizable monomer) as the base material. In the case in which a polyfunctional photopolymerizable low-molecular compound is contained, a (D) photopolymerization initiator described below is preferably contained, for example. The photopolymerizable low-molecular compound may be a monofunctional monomer or a polyfunctional monomer. Next, the monofunctional monomer and the polyfunctional monomer are described in order.

Examples of the monofunctional monomer include (meth)acrylamide, methylol (meth)acrylamide, methoxymethyl (meth)acrylamide, ethoxymethyl (meth)acrylamide, propoxymethyl (meth)acrylamide, butoxymethoxymethyl (meth)acrylamide, N-methylol (meth)acrylamide, N-hydroxymethyl (meth)acrylamide, (meth)acrylic acid, fumaric acid, maleic acid, maleic anhydride, itaconic acid, itaconic anhydride, citraconic acid, citraconic anhydride, crotonic acid, 2-acrylamide-2-methylpropanesulfonic acid, tert-butyl acrylamide sulfonic acid, methyl (meth)acrylate, ethyl (meth)acrylate, butyl (meth)acrylate, 2-ethylhexyl (meth)acrylate, cyclohexyl (meth)acrylate, 2-hydroxyethyl (meth)acrylate, 2-hydroxypropyl (meth)acrylate, 2-hydroxybutyl (meth)acrylate, 2-phenoxy-2-hydroxypropyl (meth)acrylate, 2-(meth)acryloyloxy-2-hydroxypropyl phthalate, glycerol mono(meth)acrylate, tetrahydrofurfuryl (meth)acrylate, dimethylaminoethyl (meth)acrylate, glycidyl (meth)acrylate, 2,2,2-trifluoroethyl (meth)acrylate, 2,2,3,3-tetrafluoropropyl (meth)acrylate, and half (meth)acrylates of phthalic acid derivatives. The monofunctional monomer may be used singly, or two or more thereof may be used in combination.

Examples of the polyfunctional monomer include polyfunctional monomers such as ethylene glycol di(meth)acrylate, diethylene glycol di(meth)acrylate, tetraethylene glycol di(meth)acrylate, propylene glycol di(meth)acrylate, polypropylene glycol di(meth)acrylate, butylene glycol di(meth)acrylate, neopentyl glycol di(meth)acrylate, 1,6-hexane glycol di(meth)acrylate, trimethylolpropane tri(meth)acrylate, glycerol di(meth)acrylate, pentaerythritol triacrylate, pentaerythritol tetraacrylate, dipentaerythritol pentaacrylate, dipentaerythritol hexaacrylate, pentaerythritol di(meth)acrylate, pentaerythritol tri(meth)acrylate, pentaerythritol tetra (meth)acrylate, dipentaerythritol penta(meth)acrylate, dipentaerythritol hexa(meth)acrylate, 2,2-bis(4-(meth)acryloxydiethoxyphenyl)propane, 2,2-bis(4-(meth)acryloxypolyethoxyphenyl)propane, 2-hydroxy-3-(meth)acryloyloxypropyl (meth)acrylate, ethylene glycol diglycidyl ether di(meth)acrylate, diethylene glycol diglycidyl ether di(meth)acrylate, phthalic acid diglycidyl ester di(meth)acrylate, glycerol triacrylate, glycerol polyglycidyl ether poly(meth)acrylate, urethane (meth)acrylate (in other words, a reaction product of tolylene diisocyanate, trimethylhexamethylene diisocyanate, hexamethylene diisocyanate, or the like with 2-hydroxyethyl (meth)acrylate), methylenebis(meth)acrylamide, (meth)acrylamide methylene ether, condensates of a polyhydric alcohol and N-methylol (meth)acrylamide, and triacrylformal. The polyfunctional monomer may be used singly, or two or more thereof may be used in combination.

[Photopolymerizable Polymer Compound]

The composition may contain a photopolymerizable polymer compound as the base material. As the photopolymerizable polymer compound, a resin containing an ethylenically unsaturated group is preferably used. Examples of the resin containing an ethylenically unsaturated group include oligomers derived from polymerization of (meth)acrylic acid, fumaric acid, maleic acid, monomethyl fumarate, monoethyl fumarate, 2-hydroxyethyl (meth)acrylate, ethylene glycol monomethyl ether (meth)acrylate, ethylene glycol monoethyl ether (meth)acrylate, glycerol (meth)acrylate, (meth)acrylamide, acrylonitrile, methacrylonitrile, methyl (meth)acrylate, ethyl (meth)acrylate, isobutyl (meth)acrylate, 2-ethylhexyl (meth)acrylate, benzyl (meth)acrylate, ethylene glycol di(meth)acrylate, diethylene glycol di(meth)acrylate, triethylene glycol di(meth)acrylate, tetraethylene glycol di(meth)acrylate, butylene glycol di(meth)acrylate, propylene glycol di(meth)acrylate, trimethylolpropane tri(meth)acrylate, tetramethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, 1,6-hexanediol di(meth)acrylate, and cardo epoxy diacrylate; polyester (meth)acrylates obtained by subjecting a polyester prepolymer derived from condensation between a polyhydric alcohol and a monobasic acid or a polybasic acid to reaction with (meth)acrylic acid; polyurethane (meth)acrylates obtained by subjecting a polyol and a compound having two isocyanate groups to reaction and then subjecting the resulting product to reaction with (meth)acrylic acid; and epoxy (meth)acrylate resins obtained by subjecting an epoxy resin such as a bisphenol A type epoxy resin, a bisphenol F type epoxy resin, a bisphenol S type epoxy resin, a phenol or cresol novolac type epoxy resin, a resole type epoxy resin, a triphenol methane type epoxy resin, a polycarboxylic acid polyglycidyl ester, a polyol polyglycidyl ester, an aliphatic or alicyclic epoxy resin, an amine epoxy resin, or a dihydroxybenzene type epoxy resin to reaction with (meth)acrylic acid. A resin obtained by subjecting an epoxy (meth)acrylate resin to reaction with a polybasic acid anhydride may also be suitable for use. In the present specification, "(meth)acryl" means "acryl or methacryl".

A preferable resin containing an ethylenically unsaturated group is a resin obtained by subjecting a product of reaction between an epoxy compound and a carboxylic acid compound containing an unsaturated group to another reaction with a polybasic acid anhydride or a resin obtained by subjecting at least some of the carboxy groups of a polymer containing a unit derived from an unsaturated carboxylic acid to reaction with a (meth)acrylic acid ester having an alicyclic epoxy group and/or a (meth)acrylic acid epoxyalkyl ester (hereinafter, these resins are collectively called "resin containing a constituent unit having an ethylenically unsaturated group"). The ethylenically unsaturated group of the constituent unit having an ethylenically unsaturated group is preferably a (meth)acryloyloxy group.

Among these, a resin containing a constituent unit having an ethylenically unsaturated group or a compound represented by the following formula (c7) is preferable. This compound represented by the formula (c7) is preferable because it itself is highly photocurable.

[Chem. 35]

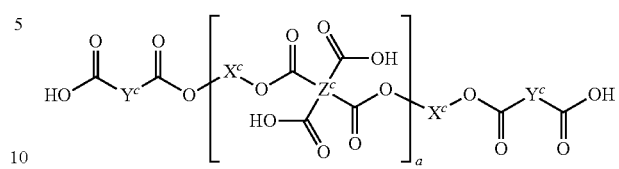

(c7)

In the formula (c7), $X^c$ represents a group represented by the following formula (c8).

[Chem. 36]

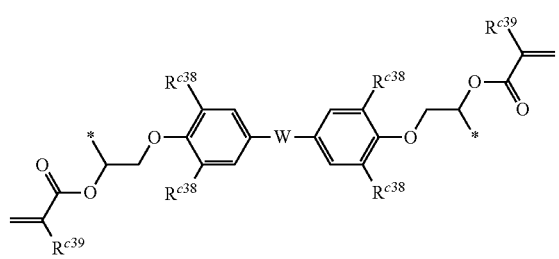

(c8)

In the formula (c8), $R^{c38}$ represents each independently a hydrogen atom, a hydrocarbon group having 1 to 6 carbon atoms, or a halogen atom; $R^{c39}$ represents each independently a hydrogen atom or a methyl group; and W represents a single bond or a group represented by the following structural formula (c9). In the formulae (c8) and (c9), "*" represents the position where a divalent group is bonded.

[Chem. 37]

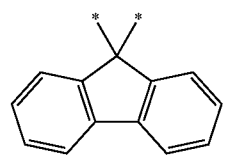

(c9)

In the formula (c7), $Y^c$ represents a residue that is obtained by removing an acid anhydride group (—CO—O—CO—) from a dicarboxylic anhydride. Examples of the dicarboxylic anhydride include maleic anhydride, succinic anhydride, itaconic anhydride, phthalic anhydride, tetrahydrophthalic anhydride, hexahydrophthalic anhydride, methylendomethylene tetrahydrophthalic anhydride, chlorendic anhydride, methyltetrahydrophthalic anhydride, and glutaric anhydride.

In the formula (c7), $Z^c$ represents a residue that is obtained by removing two acid anhydride groups from a tetracarboxylic dianhydride. Examples of the tetracarboxylic dianhydride include pyromellitic anhydride, benzophenone tetracarboxylic dianhydride, biphenyltetracarboxylic dianhydride, and biphenyl ether tetracarboxylic dianhydride. In the formula (c7), a represents an integer of 0 to 20.

The acid value of the resin containing an ethylenically unsaturated group is preferably 10 to 150 mgKOH/g, more preferably 70 to 110 mgKOH/g in terms of resin solid content. The acid value is preferably not lower than 10 mgKOH/g to obtain sufficient solubility in a developing solution. The acid value is preferably not higher than 150 mgKOH/g to obtain sufficient curability and excellent surface properties.

The mass average molecular weight of the resin containing an ethylenically unsaturated group is preferably 1000 to 40000, more preferably 2000 to 30000. The mass average molecular weight is preferably not lower than 1000 to obtain excellent heat resistance and excellent film strength. The mass average molecular weight is preferably not higher than 40000 to achieve excellent development.

In the case in which the composition contains the (C) base material, the content of the (C) base material in the composition is preferably 50 to 95% by mass, more preferably 60 to 90% by mass, particularly preferably 65 to 80% by mass with respect to the solid content (mass) of the composition.

<(D) Photopolymerization Initiator, Acid Generator, or Curing Agent>

In the case in which the composition contains the (C) thermosetting base material such as an epoxy compound or an oxetane compound or the (C) photocurable base material, the composition may contain a photopolymerization initiator, an acid generator, or a curing agent as a component for curing the (C) base material. In the case in which the (C) base material in the composition is an epoxy compound or an oxetane compound having a functional group (such as a carboxy group, a carboxylic anhydride group, or an amino group) that is reactive with an epoxy group or an oxetanyl group, it is not necessary that the composition contain an acid generator or a curing agent. In the specification of the present application, a compound that initiates photopolymerization of a compound containing an unsaturated double bond is called "photopolymerization initiator"; a compound that generates an acid by the action of light or heat and then by the action of the resulting acid, cures a compound containing an epoxy group or an oxetanyl group is called "acid generator"; and a compound that is not an acid generator and is conventionally used as a curing agent for curing an epoxy compound and an oxetane compound is called "curing agent".

[(D1) Photopolymerization Initiator]

A (D1) photopolymerization initiator is used in combination with the (C) photocurable base material and cures the (C) photocurable base material through light exposure. The (D1) photopolymerization initiator is not particularly limited and may be a conventionally known photopolymerization initiator.

Specific examples of the photopolymerization initiator include 1-hydroxycyclohexylphenyl ketone, 2-hydroxy-2-methyl-1-phenylpropan-1-one, 1-[4-(2-hydroxyethoxy)phenyl]-2-hydroxy-2-methyl-1-propan-1-one, 1-(4-isopropylphenyl)-2-hydroxy-2-methylpropan-1-one, 1-(4-dodecylphenyl)-2-hydroxy-2-methylpropan-1-one, 2,2-dimethoxy-1,2-diphenylethan-1-one, bis(4-dimethylaminophenyl) ketone, 2-methyl-1-[4-(methylthio)phenyl]-2-morpholinopropan-1-one, 2-benzyl-2-dimethylamino-1-(4-morpholinophenyl)-butan-1-one, O-acetyl-1-[6-(2-methylbenzoyl)-9-ethyl-9H-carbazol-3-yl] ethanone oxime, (9-ethyl-6-nitro-9H-carbazol-3-yl) [4-(2-methoxy-1-methylethoxy)-2-methylphenyl]methanon O-acetyloxime, 2-(benzoyloxyimino)-1-[4-(phenylthio)phenyl]-1-octanone, 2,4,6-trimethylbenzoyldiphenylphosphine oxide, 4-benzoyl-4'-methyldimethyl sulfide, 4-dimethylaminobenzoic acid, methyl 4-dimethylaminobenzoate, ethyl 4-dimethylaminobenzoate, butyl 4-dimethylaminobenzoate, 4-dimethylamino-2-ethylhexylbenzoic acid, 4-dimethylamino-2-isoamylbenzoic acid, benzyl-β-methoxyethyl acetal, benzyl dimethyl ketal, 1-phenyl-1,2-propanedion-2-(O-ethoxycarbonyl) oxime, methyl o-benzoylbenzoate, 2,4-diethylthioxanthone, 2-chlorothioxanthone, 2,4-dimethylthioxanthone, 1-chloro-4-propoxythioxanthone, thioxanthene, 2-chlorothioxanthene, 2,4-diethylthioxanthene, 2-methylthioxanthene, 2-isopropylthioxanthene, 2-ethylanthraquinone, octamethylanthraquinone, 1,2-benzanthraquinone, 2,3-diphenylanthraquinone, azobisisobutyronitrile, benzoyl peroxide, cumene hydroperoxide, 2-mercaptobenzimidazole, 2-mercaptobenzoxazole, 2-mercaptobenzothiazole, 2-(o-chlorophenyl)-4,5-di(m-methoxyphenyl)-imidazolyl dimer, benzophenone, 2-chlorobenzophenone, p,p'-bisdimethylaminobenzophenone, 4,4'-bisdiethylaminobenzophenone, 4,4'-dichlorobenzophenone, 3,3-dimethyl-4-methoxybenzophenone, benzyl, benzoin, benzoin methyl ether, benzoin ethyl ether, benzoin isopropyl ether, benzoin-n-butyl ether, benzoin isobutyl ether, benzoin butyl ether, acetophenone, 2,2-diethoxyacetophenone, p-dimethylacetophenone, p-dimethylaminopropiophenone, dichloroacetophenone, trichloroacetophenone, p-tert-butylacetophenone, p-dimethylaminoacetophenone, p-tert-butyltrichloroacetophenone, p-tert-butyldichloroacetophenone, α,α-dichloro-4-phenoxyacetophenone, thioxanthone, 2-methylthioxanthone, 2-isopropylthioxanthone, dibenzosuberone, pentyl-4-dimethylamino benzoate, 9-phenylacridine, 1,7-bis-(9-acridinyl)heptane, 1,5-bis-(9-acridinyl)pentane, 1,3-bis-(9-acridinyl)propane, p-methoxytriazine, 2,4,6-tris(trichloromethyl)-s-triazine, 2-methyl-4,6-bis(trichloromethyl)-s-triazine, 2-[2-(5-methylfuran-2-yl) ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis (trichloromethyl)-s-triazine, 2-[2-(3,4-dimethoxyphenyl) ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, 2-(4-n-butoxyphenyl)-4,6-bis(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(3-bromo-4-methoxy) styrylphenyl-s-triazine, and 2,4-bis-trichloromethyl-6-(2-bromo-4-methoxy)styrylphenyl-s-triazine. The (D1) photopolymerization initiator may be used either singly or in combination of two or more.

Among these, an oxime-type photopolymerization initiator is particularly preferable from the viewpoint of sensitivity. Particularly preferable examples of the oxime-type photopolymerization initiator include O-acetyl-1-[6-(2-methylbenzoyl)-9-ethyl-9H-carbazol-3-yl]ethanone oxime, ethanone, 1-[9-ethyl-6-(pyrrol-2-ylcarbonyl)-9H-carbazol-3-yl], 1-(O-acetyloxime), and 2-(benzoyloxyimino)-1-[4-(phenylthio)phenyl]-1-octanone.

The content of the (D1) photopolymerization initiator is preferably 0.5 to 30 parts by mass, more preferably 1 to 20 parts by mass with respect to 100 parts by mass of the solid content of the composition.

The (D1) photopolymerization initiator may be used in combination with a photoinitiator aid. Examples of the photoinitiator aid include triethanolamine, methyldiethanolamine, triisopropanolamine, methyl 4-dimethylaminobenzoate, ethyl 4-dimethylaminobenzoate, isoamyl 4-dimethylaminobenzoate, 2-ethylhexyl 4-dimethylaminobenzoate, 2-dimethylaminoethyl benzoate, N,N-dimethyl p-toluidine, 4,4'-bis(dimethylamino) benzophenone, 9,10-dimethoxyanthracene, 2-ethyl-9,10-dimethoxyanthracene, 9,10-diethoxyanthracene, 2-ethyl-9,10-diethoxyanthracene, and thiol compounds such as 2-mercaptobenzothiazole, 2-mercaptobenzoxazole, 2-mercaptobenzimidazole, 2-mercapto-5-methoxybenzothiazole, 3-mercaptopropionic acid, methyl 3-mercaptopropionate, pentaerythritol tetramercaptoacetate, and 3-mercaptopropionate. The photoinitiator aid may be used either singly or in combination of two or more.

[(D2) Acid Generator]

As the (D2) acid generator, a photoacid generator that generates an acid in response to active ray irradiation or radiation or a thermal acid generator that generates an acid in response to heat may be preferably used. The (D2) acid generator may be used in combination with an epoxy-group-containing resin, an epoxy compound, an oxetane compound, or the like and generates an acid by the action of light or heat to thereby contribute to curing.

As the photoacid generator, acid generators of the first to the fifth aspects described below are preferable. Next, the suitable photoacid generators of the first to the fifth aspects are described.

Examples of the photoacid generator of the first aspect include a compound represented by the following formula (d1).

[Chem. 38]

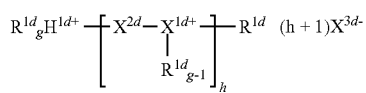

(d1)

In the formula (d1), $X^{1d}$ represents a sulfur atom or an iodine atom having a valence of g; g is 1 or 2; h represents the number of repeating units of the structure in parentheses; $R^{1d}$ represents an organic group bonded to $X^{1d}$ and represents an aryl group having 6 to 30 carbon atoms, a heterocyclic group having 4 to 30 carbon atoms, an alkyl group having 1 to 30 carbon atoms, an alkenyl group having 2 to 30 carbon atoms, or an alkynyl group having 2 to 30 carbon atoms; $R^{1d}$ may be substituted with at least one selected from the group consisting of an alkyl group, a hydroxy group, an alkoxy group, an alkylcarbonyl group, an arylcarbonyl group, an alkoxycarbonyl group, an aryloxycarbonyl group, an arylthiocarbonyl group, an acyloxy group, an arylthio group, an alkylthio group, an aryl group, a heterocycle group, an aryloxy group, an alkylsulfinyl group, an arylsulfinyl group, an alkylsulfonyl group, an arylsulfonyl group, an alkyleneoxy group, an amino group, a cyano group, a nitro group, and a halogen; the number of $R^{1d}$ is g+h(g−1)+1; each $R^{1d}$ may be the same or different from each other; two or more $R^{1d}$s may be bonded to each other directly or via —O—, —S—, —SO—, —SO$_2$—, —NH—, —NR$^{2d}$—, —CO—, —COO—, —CONH—, an alkylene group having 1 to 3 carbon atoms, or a phenylene group to form a ring structure containing $X^{1d}$; and $R^{2d}$ is an alkyl group having 1 to 5 carbon atoms or an aryl group having 6 to 10 carbon atoms.

$X^{2d}$ is a structure represented by the following formula (d2).

[Chem. 39]

(d2)

In the formula (d2), $X^{4d}$ represents an alkylene group having 1 to 8 carbon atoms, an arylene group having 6 to 20 carbon atoms, or a divalent group of a heterocyclic compound having 8 to 20 carbon atoms, and $X^{4d}$ may be substituted with at least one selected from the group consisting of an alkyl group having 1 to 8 carbon atoms, an alkoxy group having 1 to 8 carbon atoms, an aryl group having 6 to 10 carbon atoms, a hydroxy group, a cyano group, a nitro group, and halogen. $X^{5d}$ represents —O—, —S—, —SO—, —SO$_2$—, —NH—, —NR$^{2d}$—, —CO—, —COO—, —CONH—, an alkylene group having 1 to 3 carbon atoms, or a phenylene group. h represents the number of repeating units of the structure in parentheses. $X^{4d}$s in the number of h+1 and $X^{5d}$s in the number of h may be identical to or different from each other. $R^{2d}$ has the same definition as described above.

$X^{3d}$— represents a counterion of an onium, and examples thereof include an alkylfluorophosphoric acid anion represented by the following formula (d17) or a borate anion represented by the following formula (d18).

[Chem. 40]

(d17)

In the formula (d17), $R^{3d}$ represents an alkyl group that is optionally substituted with a fluorine atom. In the case in which $R^{3d}$ is an alkyl group substituted with a fluorine atom, 80% or more of the hydrogen atoms in the alkyl group are preferably substituted by fluorine atoms. j represents the number of $R^{3d}$s and is an integer of 1 to 5. $R^{3d}$s in the number of j may be respectively identical to or different from each other.

[Chem. 41]

(d18)

In the formula (d18), $R^{4d}$ to $R^{7d}$ each independently represents a fluorine atom or a phenyl group, and a part or all of the hydrogen atoms of the phenyl group may be substituted by at least one selected from the group consisting of a fluorine atom and a trifluoromethyl group.

Examples of the onium ion in the compound represented by the formula (d1) include triphenylsulfonium, tri-p-tolylsulfonium, 4-(phenylthio)phenyldiphenylsulfonium, bis[4-(diphenylsulfonio)phenyl] sulfide, bis[4-{bis[4-(2-hydroxyethoxy)phenyl]sulfonio}phenyl] sulfide, bis{4-[bis(4-fluorophenyl)sulfonio]phenyl} sulfide, 4-(4-benzoyl-2-chlorophenylthio)phenylbis(4-fluorophenyl)sulfonium, 7-isopropyl-9-oxo-10-thia-9,10-dihydroanthran-2-yldi-p-tolylsulfonium, 7-isopropyl-9-oxo-10-thia-9,10-dihydroanthracen-2-yldiphenylsulfonium, 2-[(diphenyl)sulfonio]thioxanthone, 4-[4-(4-tert-butylbenzoyl)phenylthio]phenyldi-p-tolylsulfonium, 4-(4-benzoylphenylthio)

phenyldiphenylsulfonium, diphenylphenacylsulfonium, 4-hydroxyphenylmethylbenzylsulfonium, 2-naphthylmethyl(1-ethoxycarbonyl)ethylsulfonium, 4-hydroxyphenylmethylphenacylsulfonium, phenyl[4-(4-biphenylthio)phenyl]4-biphenylsulfonium, phenyl[4-(4-biphenylthio)phenyl]3-biphenylsulfonium, [4-(4-acetophenylthio)phenyl]diphenylsulfonium, octadecylmethylphenacylsulfonium, diphenyliodonium, di-p-tolyliodonium, bis(4-dodecylphenyl)iodonium, bis(4-methoxyphenyl)iodonium, (4-octyloxyphenyl)phenyliodonium, bis(4-decyloxy)phenyliodonium, 4-(2-hydroxytetradecyloxy)phenylphenyliodonium, 4-isopropylphenyl(p-tolyl)iodonium, and 4-isobutylphenyl(p-tolyl)iodonium.

Among the onium ions in the compound represented by the formula (d1), a preferred onium ion may be a sulfonium ion represented by the following formula (d19).

[Chem. 42]

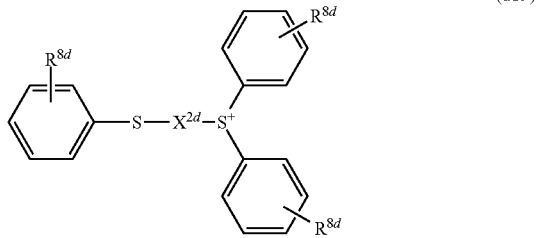

(d19)

In the formula (d19), $R^{8d}$ each independently represents a hydrogen atom or a group selected from the group consisting of alkyl, hydroxyl, alkoxy, alkylcarbonyl, alkylcarbonyloxy, alkyloxycarbonyl, a halogen atom, an aryl, which may be substituted, and arylcarbonyl. $X^{2d}$ has the same definition as $X^{2d}$ in the formula (d1).

Specific examples of the sulfonium ion represented by the formula (d19) include 4-(phenylthio)phenyldiphenylsulfonium, 4-(4-benzoyl-2-chlorophenylthio)phenylbis(4-fluorophenyl)sulfonium, 4-(4-benzoylphenylthio)phenyldiphenylsulfonium, phenyl[4-(4-biphenylthio)phenyl]4-biphenylsulfonium, phenyl[4-(4-biphenylthio)phenyl]3-biphenylsulfonium, [4-(4-acetophenylthio)phenyl]diphenylsulfonium, and diphenyl[4-(p-terphenylthio)phenyl]diphenylsulfonium.

In regard to the alkylfluorophosphoric acid anion represented by the formula (d17), $R^{3d}$ represents an alkyl group substituted with a fluorine atom, and a preferred number of carbon atoms is 1 to 8, while a more preferred number of carbon atoms is 1 to 4. Specific examples of the alkyl group include linear alkyl groups such as methyl, ethyl, propyl, butyl, pentyl and octyl; branched alkyl groups such as isopropyl, isobutyl, sec-butyl and tert-butyl; and cycloalkyl groups such as cyclopropyl, cyclobutyl, cyclopentyl, and cyclohexyl. The proportion of hydrogen atoms substituted by fluorine atoms in the alkyl groups is usually 80% or more, preferably 90% or more, and even more preferably 100%. If the substitution ratio of fluorine atoms is less than 80%, the acid strength of the onium alkylfluorophosphate represented by the formula (d1) decreases.

A particularly preferred example of $R^{3d}$ is a linear or branched perfluoroalkyl group having 1 to 4 carbon atoms and a substitution ratio of fluorine atoms of 100%. Specific examples thereof include $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)$ CF, and $(CF_3)_3C$. j which is the number of $R^{3d}$s is an integer of 1 to 5, and is preferably 2 to 4, and particularly preferably 2 or 3.

Specific examples of a preferable alkylfluorophosphoric acid anion include $[(CH_3CH_2)_2PF_4]^-$, $[(CH_3CH_2)_3PF_3]^-$, $[((CH_3)_2CH)_2PF_4]^-$, $[((CH_3)_2CH)_3PF_3]^-$, $[(CH_3CH_2CH_2)_2PF_4]^-$, $[(CH_3CH_2CH_2)_3PF_3]^-$, $[((CH_3)_2CHCH_2)_2PF_4]^-$, $[((CH_3)_2CHCH_2)_3PF_3]^-$, $[(CH_3CH_2CH_2CH_2)_2PF_4]^-$, or $[(CH_3CH_2CH_2)_3PF_3]^-$, $[(CF_3CF_2)_2PF_4]^-$, $[(CF_3CF_2)_3PF_3]^-$, $[((CF_3)_2CF)_2PF_4]^-$, $[((CF_3)_2CF)_3PF_3]^-$, $[(CF_3CF_2CF_2)_2PF_4]^-$, $[(CF_3CF_2CF_2)_3PF_3]^-$, $[((CF_3)_2CFCF_2)_2PF_4]^-$, $[((CF_3)_2CFCF_2)_3PF_3]^-$, $[(CF_3CF_2CF_2CF_2)_2PF_4]^-$, or $[(CF_3CF_2CF_2)_3PF_3]^-$. Among these, $[(CH_3CH_2)_3PF_3]^-$, $[(CH_3CH_2CH_2)_3PF_3]^-$, $[((CH_3)_2CH)_3PF_3]^-$, $[((CH_3)_2CH)_2PF_4]^-$, $[((CH_3)_2CHCH_2)_3PF_3]^-$, or $[((CH_3)_2CHCH_2)_2PF_4]^-$, $[(CF_3CF_2)_3PF_3]^-$, $[(CF_3CF_2CF_2)_3PF_3]^-$, $[((CF_3)_2CF)_3PF_3]^-$, $[((CF_3)_2CF)_2PF_4]^-$, $[((CF_3)_2CFCF_2)_3PF_3]^-$, or $[((CF_3)_2CFCF_2)_2PF_4]$ is particularly preferable.

Preferred specific examples of the borate anion represented by the formula (d18) include tetrakis(pentafluorophenyl)borate ($[B(C_6F_5)_4]^-$), tetrakis[(trifluoromethyl)phenyl]borate ($[B(C_6H_4CF_3)_4]^-$), difluorobis(pentafluorophenyl)borate ($[(C_6F_5)_2BF_2]^-$), trifluoro (pentafluorophenyl)borate ($[(C_6F_5)BF_3]^-$), and tetrakis(difluorophenyl)borate ($[B(C_6H_3F_2)_4]^-$). Among these, tetrakis(pentafluorophenyl)borate ($[B(C_6F_5)_4]^-$) is particularly preferred.

Examples of the photoacid generator of the second aspect include halogen-containing triazine compounds such as 2,4-bis(trichloromethyl)-6-piperonyl-1,3,5-triazine, 2,4-bis(trichloromethyl)-6-[2-(2-furyl)ethenyl]-s-triazine, 2,4-bis(trichloromethyl)-6-[2-(5-methyl-2-furyl)ethenyl]-s-triazine, 2,4-bis(trichloromethyl)-6-[2-(5-ethyl-2-furyl)ethenyl]-s-triazine, 2,4-bis(trichloromethyl)-6-[2-(5-propyl-2-furyl)ethenyl]-s-triazine, 2,4-bis(trichloromethyl)-6-[2-(3,5-dimethoxyphenyl)ethenyl]-s-triazine, 2,4-bis(trichloromethyl)-6-[2-(3,5-diethoxyphenyl)ethenyl]-s-triazine, 2,4-bis(trichloromethyl)-6-[2-(3,5-dipropoxyphenyl)ethenyl]-s-triazine, 2,4-bis(trichloromethyl)-6-[2-(3-methoxy-5-ethoxyphenyl)ethenyl]-s-triazine, 2,4-bis(trichloromethyl)-6-[2-(3-methoxy-5-propoxyphenyl)ethenyl]-s-triazine, 2,4-bis(trichloromethyl)-6-[2-(3,4-methylenedioxyphenyl)ethenyl]-s-triazine, 2,4-bis(trichloromethyl)-6-(3,4-methylenedioxyphenyl)-s-triazine, 2,4-bis-trichloromethyl-6-(3-bromo-4-methoxy)phenyl-s-triazine, 2,4-bis-trichloromethyl-6-(2-bromo-4-methoxy)phenyl-s-triazine, 2,4-bis-trichloromethyl-6-(2-bromo-4-methoxy)styrylphenyl-s-triazine, 2,4-bis-trichloromethyl-6-(3-bromo-4-methoxy)styrylphenyl-s-triazine, 2-(4-methoxyphenyl)-4,6-bis(trichloromethyl)-1,3,5-triazine, 2-(4-methoxynaphthyl)-4,6-bis(trichloromethyl)-1,3,5-triazine, 2-[2-(2-furyl)ethenyl]-4,6-bis(trichloromethyl)-1,3,5-triazine, 2-[2-(5-methyl-2-furyl)ethenyl]-4,6-bis(trichloromethyl)-1,3,5-triazine, 2-[2-(3,5-dimethoxyphenyl)ethenyl]-4,6-bis(trichloromethyl)-1,3,5-triazine, 2-[2-(3,4-dimethoxyphenyl)ethenyl]-4,6-bis(trichloromethyl)-1,3,5-triazine, 2-(3,4-methylenedioxyphenyl)-4,6-bis(trichloromethyl)-1,3,5-triazine, tris(1,3-dibromopropyl)-1,3,5-triazine and tris(2,3-dibromopropyl)-1,3,5-triazine, and halogen-containing triazine compounds represented by the following formula (d3) such as tris(2,3-dibromopropyl)isocyanurate.

[Chem. 43]

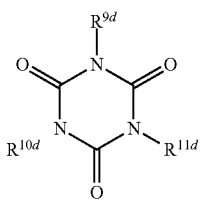
(d3)

In the formula (d3), $R^{9d}$, $R^{10d}$, and $R^{11d}$ each independently represent a halogenated alkyl group.

Examples of the photoacid generator of the third aspect include α-(p-toluenesulfonyloxyimino)-phenylacetonitrile, α-(benzenesulfonyloxyimino)-2,4-dichlorophenylacetonitrile, α-(benzenesulfonyloxyimino)-2,6-dichlorophenylacetonitrile, α-(2-chlorobenzenesulfonyloxyimino)-4-methoxyphenylacetonitrile and α-(ethylsulfonyloxyimino)-1-cyclopentenylacetonitrile, and compounds represented by the following formula (d4) having an oximesulfonate group.

[Chem. 44]

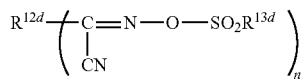
(d4)

In the formula (d4), $R^{12d}$ represents a monovalent, bivalent or trivalent organic group, $R^{13d}$ represents a substituted or unsubstituted saturated hydrocarbon group, an unsaturated hydrocarbon group, or an aromatic compound group, and n represents the number of repeating units of the structure in the parentheses.

In the formula (d4), the aromatic compound group indicates a group of compounds having physical and chemical properties characteristic of aromatic compounds, and examples thereof include aryl groups such as a phenyl group and a naphthyl group, and heteroaryl groups such as a furyl group and a thienyl group may be exemplified. These may have one or more appropriate substituents such as halogen atoms, alkyl groups, alkoxy groups and nitro groups on the rings. It is particularly preferable that $R^{13d}$ is an alkyl group having 1 to 6 carbon atoms such as a methyl group, an ethyl group, a propyl group, and a butyl group. In particular, compounds in which $R^{12d}$ represents an aromatic compound group, and $R^{13d}$ represents an alkyl group having 1 to 4 carbon atoms are preferred.

In the case in which n=1, the acid generator represented by the formula (d4) is a compound in which $R^{12d}$ is one of a phenyl group, a methylphenyl group, and a methoxyphenyl group and $R^{13d}$ is a methyl group, and specific examples thereof include α-(methylsulfonyloxyimino)-1-phenylacetonitrile, α-(methylsulfonyloxyimino)-1-(p-methylphenyl)acetonitrile, α-(methylsulfonyloxyimino)-1-(p-methoxyphenyl)acetonitrile, and [2-(propylsulfonyloxyimino)-2,3-dihydroxythiophen-3-ylidene] (o-tolyl)acetonitrile. In the case in which n=2, specific examples of the photoacid generator represented by the formula (d4) include photoacid generators represented by the following formulae.

[Chem. 45]

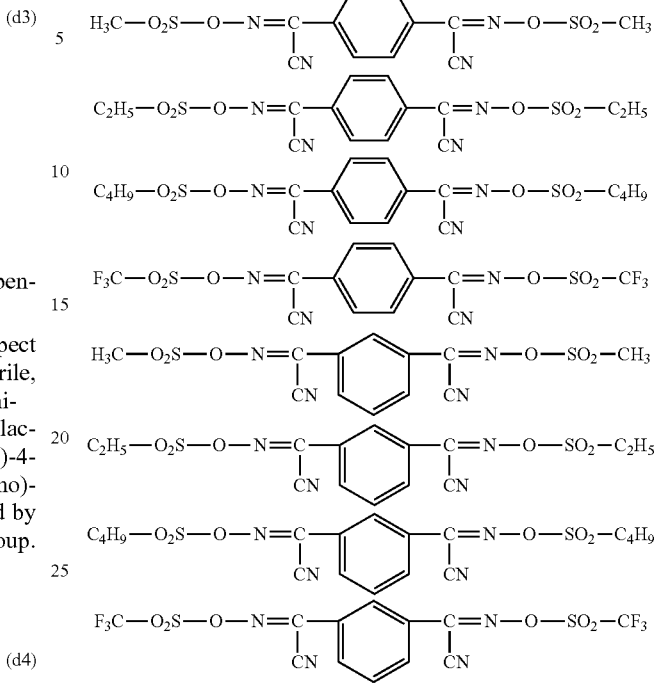

Examples of the photoacid generator of the fourth aspect include onium salts that have a naphthalene ring at their cation moiety. The expression "have a naphthalene ring" indicates having a structure derived from naphthalene and also indicates at least two ring structures and their aromatic properties are maintained. The naphthalene ring may have a substituent such as a linear or branched alkyl group having 1 to 6 carbon atoms, a hydroxy group, a linear or branched alkoxy group having 1 to 6 carbon atoms or the like. The structure derived from the naphthalene ring, which may be of a monovalent group (one free valance) or of a bivalent group (two free valences), is desirably of a monovalent group (in this regard, the number of free valance is counted except for the portions connecting with the substituents described above). The number of naphthalene rings is preferably 1 to 3.

Preferably, the cation moiety of the onium salt having a naphthalene ring at the cation moiety is of the structure represented by the following formula (d5).

[Chem. 46]

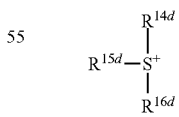
(d5)

In the formula (d5), at least one of $R^{14d}$, $R^{15d}$, and $R^{16d}$ represents a group represented by the following formula (d6), and the remaining represents a linear or branched alkyl group having 1 to 6 carbon atoms, a phenyl group which may have a substituent, a hydroxy group, or a linear or branched alkoxy group having 1 to 6 carbon atoms. Alternatively, one of $R^{14d}$, $R^{15d}$, and $R^{16d}$ is a group represented by the following formula (d6), and the remaining two are each independently a linear or branched alkylene group having 1 to 6 carbon atoms, and these terminals may bond to form a ring structure.

[Chem. 47]

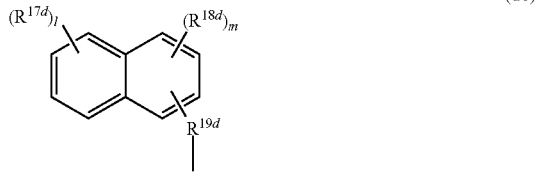

(d6)

In the formula (d6), $R^{17d}$ and $R^{18d}$ each independently represent a hydroxy group, a linear or branched alkoxy group having 1 to 6 carbon atoms, or a linear or branched alkyl group having 1 to 6 carbon atoms, and $R^{19d}$ represents a single bond or a linear or branched alkylene group having 1 to 6 carbon atoms that may have a substituent. l and m each independently represent an integer of 0 to 2, and l+m is no greater than 3. In this regard, when there exists a plurality of $R^{17d}$, they may be identical or different from each other. Furthermore, when there exist a plurality of $R^{18d}$, they may be identical or different from each other.

Preferably, among $R^{14d}$, $R^{15d}$, and $R^{16d}$ as above, the number of groups represented by the formula (d6) is one in view of the stability of the compound, and the remaining are linear or branched alkylene groups having 1 to 6 carbon atoms of which the terminals may bond to form a ring. In this case, the two alkylene groups described above form a 3 to 9 membered ring including sulfur atom(s). Preferably, the number of atoms to form the ring (including sulfur atom(s)) is 5 or 6.

The substituent, which the alkylene group may have, is exemplified by an oxygen atom (in this case, a carbonyl group is formed together with a carbon atom that constitutes the alkylene group), a hydroxy group or the like.

Alternatively, the substituent, which the phenyl group may have, is exemplified by a hydroxy group, a linear or branched alkoxy groups having 1 to 6 carbon atoms, linear or branched alkyl groups having 1 to 6 carbon atoms, or the like.

Examples of suitable cation moiety include those represented by the following formulae (d7) and (d8), and the structure represented by the following formula (d8) is particularly preferable.

[Chem. 48]

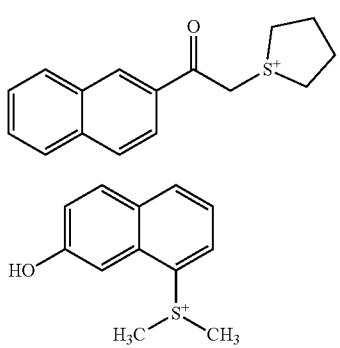

(d7)

(d8)

The cation moieties, which may be of an iodonium salt or a sulfonium salt, are desirably of a sulfonium salt in view of acid-producing efficiency or the like.

It is, therefore, desirable that the preferable anion moiety of the onium salt having a naphthalene ring at the cation moiety is an anion capable of forming a sulfonium salt.

The anion moiety of the acid generator is exemplified by fluoroalkylsulfonic acid ions, of which hydrogen atom(s) being partially or entirely fluorinated, or aryl sulfonic acid ions.

The alkyl group of the fluoroalkylsulfonic acid ions may be linear, branched or cyclic and have 1 to 20 carbon atoms. Preferably, the carbon number is 1 to 10 in view of bulkiness and diffusion distance of the produced acid. In particular, branched or cyclic groups are preferable due to shorter diffusion length. Also, methyl, ethyl, propyl, butyl, octyl groups and the like are preferable due to being inexpensively synthesizable.

The aryl group of the aryl sulfonic acid ions may be an aryl group having 6 to 20 carbon atoms, and is exemplified by a phenol group or a naphthyl group that may be substituted or unsubstituted with an alkyl group or a halogen atom. In particular, aryl groups having 6 to 10 carbon atoms are preferred since they can be synthesized inexpensively. Specific examples of preferable aryl group include phenyl, toluenesulfonyl, ethylphenyl, naphthyl, methylnaphthyl groups and the like.

When hydrogen atoms in the fluoroalkylsulfonic acid ion or the aryl sulfonic acid ion are partially or entirely substituted with a fluorine atom, the fluorination rate is preferably 10% to 100%, and more preferably 50% to 100%; it is particularly preferable that all hydrogen atoms are each substituted with a fluorine atom in view of higher acid strength. Specific examples thereof include trifluoromethane sulfonate, perfluorobutane sulfonate, perfluorooctane sulfonate, perfluorobenzene sulfonate, and the like.

Among these, examples of a preferable anion moiety include one represented by the following formula (d9).

[Chem. 49]

$$R^{20d}SO_3^-  \quad (d9)$$

In the formula (d9), $R^{20d}$ is a group represented by the following formula (d10) or (d11) or a group represented by the following formula (d12).

[Chem. 50]

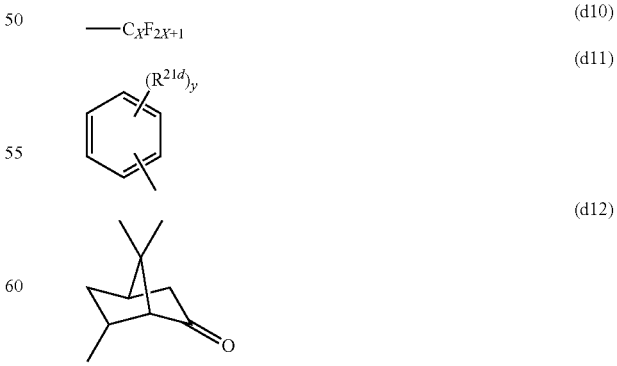

In the formula (d10), x represents an integer of 1 to 4. In the formula (d11), $R^{21d}$ represents a hydrogen atom, a hydroxy group, a linear or branched alkyl group having 1 to 6 carbon atoms, or a linear or branched alkoxy group having 1 to 6 carbon atoms; and y is an integer of 1 to 3. Among these, trifluoromethanesulfonate and perfluorobutanesulfonate are preferable from the viewpoint of safety.

The anion moiety may be those represented by the following formulae (d13) and (d14) containing nitrogen.

[Chem. 51]

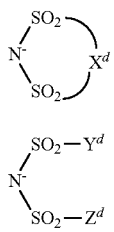

In the formulae (d13) and (d14), $X^d$ represents a linear or branched alkylene group in which at least one hydrogen atom is substituted with a fluorine atom; the number of carbon atoms in the alkylene group is 2 to 6, preferably 3 to 5, most preferably 3; $Y^d$ and $Z^d$ represent each independently a linear or branched alkyl group in which at least one hydrogen atom is substituted with a fluorine atom; and the number of carbon atoms in the alkyl group is 1 to 10, preferably 1 to 7, more preferably 1 to 3.

The number of carbon atoms in the alkylene group as $X^d$ and the number of carbon atoms in the alkyl group as $Y^d$ or $Z^d$ is preferably as small as possible because in this case, excellent solubility in an organic solvent is obtained.

The number of hydrogen atoms substituted with fluorine atoms in the alkylene group as $X^d$ or in the alkyl group as $Y^d$ or $Z^d$ is preferably as great as possible because in this case, strong acidity is obtained. The proportion of fluorine atoms in the alkylene group or the alkyl group, more specifically the fluorination rate, is preferably 70 to 100%, more preferably 90 to 100%. A perfluoroalkylene group or a perfluoroalkyl group is most preferable, in which all the hydrogen atoms are substituted with fluorine atoms.

Examples of a preferable onium salt having a naphthalene ring at the cation moiety include compounds represented by the following formulae (d15) and (d16).

[Chem. 52]

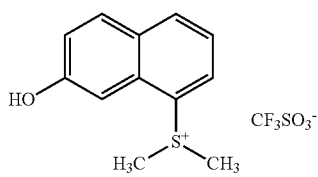

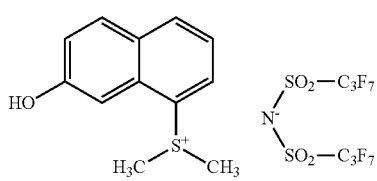

Examples of the photoacid generator of the fifth aspect include bissulfonyldiazomethanes such as bis(p-toluenesulfonyl)diazomethane, bis(1,1-dimethyl ethylsulfonyl)diazomethane, bis(cyclohexylsulfonyl)diazomethane and bis(2,4-dimethylphenylsulfonyl)diazomethane; nitrobenzyl derivatives such as 2-nitrobenzyl p-toluenesulfonate, 2,6-dinitrobenzyl p-toluenesulfonate, nitrobenzyl tosylate, dinitrobenzyl tosylate, nitrobenzyl sulfonate, nitrobenzyl carbonate and dinitrobenzyl carbonate; sulfonates such as pyrogalloltrimesylate, pyrogalloltritosylate, benzyltosylate, benzylsulfonate, N-methylsulfonyloxysuccinimide, N-trichloromethylsulfonyloxysuccinimide, N-phenylsulfonyloxymaleimide and N-methylsulfonyloxyphthalimide; trifluoromethane sulfonates such as N-hydroxyphthalimide and N-hydroxynaphthalimide; onium salts such as diphenyliodonium hexafluorophosphate, (4-methoxyphenyl)phenyliodonium trifluoromethanesulfonate, bis(p-tert-butylphenyl)iodonium trifluoromethanesulfonate, triphenylsulfonium hexafluorophosphate, (4-methoxyphenyl)diphenylsulfonium trifluoromethanesulfonate and (p-tert-butylphenyl)diphenylsulfonium trifluoromethanesulfonate; benzointosylates such as benzointosylate and α-methylbenzointosylate; other diphenyliodonium salts, triphenylsulfonium salts, phenyldiazonium salts, benzylcarbonates and the like.

Examples of a preferable thermal acid generator include oxime ester compounds of an organic sulfonic acid and organic sulfonic acid alkyl esters such as 2,4,4,6-tetrabromocyclohexadienone, benzoin tosylate, and 2-nitrobenzyl tosylate. Additionally, an onium salt such as a sulfonium salt, an iodonium salt, a benzothiazonium salt, an ammonium salt, or a phosphonium salt, for example, may also be preferably used, as appropriate, as the thermal acid generator. Among these, an oxime ester compound of an organic sulfonic acid is preferable because it has excellent stability in a non-heated state.

The content of the acid generator in the resulting cured article is not particularly limited as long as the object of the present invention is not impaired. The content of the acid generator in the composition is preferably 0.1 to 50 parts by mass, more preferably 0.5 to 30 parts by mass, particularly preferably 1 to 20 parts by mass with respect to the total mass (100) of the epoxy compound and the oxetanyl compound in the composition.

[(D3) Curing Agent]

A (D3) curing agent may be selected as appropriate from conventionally known ones except for the (D2) acid generator. The (D3) curing agent may be used in combination with an epoxy-group-containing resin, an epoxy compound, or an oxetane compound and contributes to curing when heated.

Examples of the (D3) curing agent include a phenol-based curing agent, an acid-anhydride-based curing agent, a polyamine-based curing agent, and a catalyst type curing agent. Next, the phenol-based curing agent, the acid-anhydride-based curing agent, the polyamine-based curing agent, and the catalyst type curing agent are described in order.

Examples of the phenol-based curing agent include novolac phenolic type resins such as a phenol novolac resin, a phenol aralkyl resin, a cresol novolac resin, a tert-butylphenol novolac resin, and a nonylphenol novolac resin, resole phenolic type resins, and polyoxystyrenes such as poly(p-oxystyrene). The amount of the phenol-based curing agent used is preferably 1 to 200 parts by mass, more preferably 50 to 150 parts by mass, particularly preferably 80 to 120 parts by mass with respect to the mass (100) of the base material in the composition (in particular, the total amount of the epoxy compound and the oxetanyl compound (including the resin containing an epoxy group and/or an oxetanyl group). The phenol-based curing agent may be used either singly or in combination of two or more.

Examples of the acid-anhydride-based curing agent include maleic anhydride, tetrahydrophthalic anhydride, hexahydrophthalic anhydride, methylhexahydrophthalic anhydride, hexahydrotrimellitic anhydride, phthalic anhydride, trimellitic anhydride, and a styrene-(maleic anhydride) copolymer. The amount of the acid-anhydride-based curing agent used is preferably 1 to 200 parts by mass, more preferably 50 to 150 parts by mass, particularly preferably 80 to 120 parts by mass with respect to the mass (100) of the base material in the composition (in particular, the total amount of the epoxy compound and the oxetanyl compound (including the resin containing an epoxy group and/or an oxetanyl group). The acid-anhydride-based curing agent may be used either singly or in combination of two or more.

Examples of the polyamine-based curing agent include polyamine-based curing agents such as diethylenetriamine, triethylenetetramine, tetraethylenepentamine, polyamidoamine (polyamide resin), ketimine compounds, isophoronediamine, m-xylenediamine, m-phenylenediamine, 1,3-bis(aminomethyl)cyclohexane, N-aminoethylpiperazine, 4,4'-diaminodiphenylmethane, 4,4'-diamino-3,3'-diethyldiphenylmethane, and diaminodiphenyl sulfone; aromatic diamines such as o-phenylenediamine, m-phenylenediamine, p-phenylenediamine, 3,3'-diaminodiphenyl ether, 3,4'-diaminodiphenyl ether, 4,4'-diaminodiphenyl ether, 3,3'-diaminodiphenylmethane, 3,4'-diaminodiphenylmethane, 4,4'-diaminodiphenylmethane, bis(4-amino-3,5-dimethylphenyl)methane, bis(4-amino-3,5-diisopropylphenyl)methane, 3,3'-diaminodiphenyldifluoromethane, 3,4'-diaminodiphenyldifluoromethane, 4,4'-diaminodiphenyldifluoromethane, 3,3'-diaminodiphenyl sulfone, 3,4'-diaminodiphenyl sulfone, 4,4'-diaminodiphenyl sulfone, 3,3'-diaminodiphenyl sulfide, 3,4'-diaminodiphenyl sulfide, 4,4'-diaminodiphenyl sulfide, 3,3'-diaminodiphenylketone, 3,4'-diaminodiphenylketone, 4,4'-diaminodiphenylketone, 2,2-bis(3-aminophenyl)propane, 2-(3-aminophenyl)-2-(4-aminophenyl)propane, and 2,2-bis(4-aminophenyl)propane; substituted guanidines described below; substituted biguanidines described below; substituted urea described below; and guanamine derivatives described below.

The substituted guanidine is a compound in which hydrogen atoms to be combined with nitrogen atoms included in guanidine are substituted with an organic group. The organic group may have heteroatoms such as N, O, S, P, and halogen atoms. The organic group to be combined with nitrogen atoms possessed by the substituted guanidine is preferably a hydrocarbon group or a cyano group. The hydrocarbon group is preferably an alkyl group, more preferably an alkyl group having 1 to 6 carbon atoms, and still more preferably a methyl group.

Suitable specific examples of the substituted guanidine include methylguanidine, dimethylguanidine, trimethylguanidine, tetramethylguanidine, and dicyandiamide. Of these, dicyandiamide is preferable.

The substituted biguanidine is a compound in which hydrogen atoms to be combined with nitrogen atoms included in biguanidine are substituted with an organic group. The organic group may have heteroatoms such as N, O, S, P, and halogen atoms. The organic group to be combined with nitrogen atoms possessed by the substituted biguanidine is preferably a hydrocarbon group or a cyano group. The hydrocarbon group is preferably an alkyl group, more preferably an alkyl group having 1 to 6 carbon atoms, and still more preferably a methyl group.

Suitable specific examples of the substituted biguanidine include methyl biguanidine, dimethyl biguanidine, tetramethyl biguanidine, hexamethyl biguanidine, and heptamethyl biguanidine.

The substituted urea is a compound in which hydrogen atoms to be combined with nitrogen atoms included in urea are substituted with an organic group. The organic group may have heteroatoms such as N, O, S, P, and halogen atoms. The substituted urea may be a urea dimer represented by the following formula (B1):

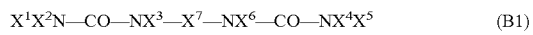

$$X^1X^2N\text{—}CO\text{—}NX^3\text{—}X^7\text{—}NX^6\text{—}CO\text{—}NX^4X^5 \quad (B1)$$

wherein, in the formula (B1), $X^1$ to $X^6$ each independently represents a hydrogen atom or an organic group, and $X^7$ is a divalent organic group.

Suitable specific examples of the substituted urea include N,N-dimethyl-N'-(3-chloro-4-methylphenyl)urea, N,N-dimethyl-N'-(4-chlorophenyl)urea, N,N-dimethyl-N'-(3,4-dichlorophenyl)urea, N,N-dimethyl-N'-phenylurea, 2,4-bis(N',N'-dimethylureide)toluene, 1,4-bis(N',N'-dimethylureide)benzene, dimethylpropyleneurea, and 1,3-hydroxymethylurea.

Suitable specific examples of the guanamine derivative include an alkylated benzoguanamine resin, a benzoguanamine resin, and a methoxymethylethoxymethylbenzoguanamine resin. Among these, an aromatic diamine or a substituted guanidine (in particular, dicyandiamide) is preferable from the viewpoint of curing of the composition at low temperature.

The amount of the polyamine-based curing agent used is preferably 0.1 to 50 parts by mass, more preferably 0.5 to 30 parts by mass, particularly preferably 1 to 15 parts by mass with respect to the mass (100) of the base material in the composition (in particular, the total amount of the epoxy compound and the oxetanyl compound (including the resin containing an epoxy group and/or an oxetanyl group). The polyamine-based curing agent may be used either singly or in combination of two or more.

The catalyst type curing agent is not particularly limited and examples thereof include imidazole compounds except for the component (A). Examples of the imidazole compound include 1-cyanoethyl-2-phenylimidazole, 2,4-diamino-6-[2'-methylimidazolyl-(1')]-ethyl-s-triazineisocyanuric acid adduct (2MA-OK, manufactured by SHIKOKU CHEMICALS CORPORATION), 2,4-diamino-6-[2'-methylimidazolyl-(1')]-ethyl-s-triazine (2MZ-A, manufactured by SHIKOKU CHEMICALS CORPORATION), 2-phenyl-4,5-dihydroxymethylimidazole (2PHZ, manufactured by SHIKOKU CHEMICALS CORPORATION), 2-phenyl-4-methyl-5-hydroxymethylimidazole (2P4MHZ, manufactured by SHIKOKU CHEMICALS CORPORATION), and the like. The amount of the catalyst type curing agent used is preferably 1 to 100 parts by mass, more preferably 1 to 80 parts by mass, particularly preferably 1 to 50 parts by mass with respect to the mass (100) of the base material in the composition (in particular, the total amount of the epoxy compound and the oxetanyl compound (including the resin containing an epoxy group and/or an oxetanyl group). The catalyst type curing agent may be used either singly or in combination of two or more.

<(E) Organic Solvent>

The composition may contain an (E) organic solvent (hereinafter, also called "component (E)" for improved application and viscosity adjustment.

Specific examples of the organic solvent include (poly)alkylene glycol monoalkyl ethers such as ethyleneglycol monomethyl ether, ethyleneglycol monoethyl ether, ethyleneglycol mono-n-propylether, ethyleneglycol mono-n-butyl ether, diethyleneglycol monomethyl ether, diethyleneglycol monoethyl ether, diethyleneglycol mono-n-propyl ether, diethyleneglycol mono-n-butyl ether, triethyleneglycol monomethyl ether, triethyleneglycol monoethyl ether, propyleneglycol monomethyl ether, propyleneglycol monoethyl ether, propyleneglycol mono-n-propyl ether, propyleneglycol mono-n-butyl ether, dipropyleneglycol monomethyl ether, dipropyleneglycol monoethyl ether, dipropyleneglycol mono-n-propyl ether, dipropyleneglycol mono-n-butyl ether, tripropyleneglycol monomethyl ether, and tripropyleneglycol monoethyl ether; (poly) alkylene glycols monoalkyl ether acetates such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate (PGMEA), and propylene glycol monoethyl ether acetate; other ethers such as diethyleneglycol dimethylether, diethyleneglycol methylethyl ether, diethyleneglycol diethylether, and tetrahydrofuran; ketones such as methyl ethyl ketone, cyclohexanone, 2-heptanone, and 3-heptanone; alkyl lactate esters such as methyl 2-hydroxypropionate and ethyl 2-hydroxypropionate; other esters such as ethyl 2-hydroxy-2-methylpropionate, methyl 3-methoxypropionate, ethyl 3-methoxypropionate, methyl 3-ethoxypropionate, ethyl 3-ethoxypropionate, ethoxy-ethylacetate, hydroxy ethylacetate, methyl 2-hydroxy-3-methylbutanoate, 3-methoxybutyl acetate, 3-methyl-3-methoxybutyl acetate, 3-methyl-3-methoxybutyl propionate, ethylacetate, n-propyl acetate, i-propyl acetate, n-butyl acetate, i-butyl acetate, n-pentyl formate, i-pentyl acetate, n-butyl propionate, ethyl butyrate, n-propyl butyrate, i-propyl butyrate, n-butyl butyrate, methyl pyruvate, ethyl pyruvate, n-propyl pyruvate, methyl acetoacetate, ethyl acetoacetate, and ethyl 2-oxobutanoate; aromatic hydrocarbons such as toluene and xylene; and nitrogen-containing organic solvents such as N,N,N',N'-tetramethylurea, N,N,2-trimethylpropionamide, N,N-dimethylacetamide, N,N-dimethylformamide, N,N-diethylacetamide, N,N-diethylformamide, 1,3-dimethyl-2-imidazolidinone, N-methylpyrrolidone, and N-ethylpyrrolidone. Among these, alkylene glycol monoalkyl ethers, alkylene glycols monoalkyl ether acetates, other ethers described above, alkyl lactate esters, other esters described above, or nitrogen-containing organic solvents are preferable, and alkylene glycols monoalkyl ether acetates, other ethers described above, other esters described above, or nitrogen-containing organic solvents are more preferable. Among these solvents, a solvent that has a low boiling point and/or that is highly volatile may be suitably selected. The solvent may be used either singly or in combination of two or more.

The content of the (E) organic solvent in the composition is not particularly limited. In the case in which the composition is subjected to application to form a coating film, for example, the content of the (E) organic solvent in the composition is determined depending on the thickness of the coating film without departing the range that allows application of the composition to the base material.

<(F) Other Components>

The composition may contain various additives other than the components described above. Examples of the additives include thickeners such as silica, organic bentonite, and montmorillonite, an antifoaming agent, a leveling agent, a silane coupling agent, an antioxidant, an anti-rust agent, a dispersant, a curing aid, a carboxy-group-containing resin, and a metal phosphinate. Among these additives, a carboxy-group-containing resin and a metal phosphinate are described below.

(Carboxy-Group-Containing Resin)

In the case in which the composition contains the (C) thermosetting or photocurable base material, the composition preferably contains a carboxy-group-containing resin. The carboxy-group-containing resin is not particularly limited provided that it is a resin containing a carboxy group and it can be uniformly mixed with the composition. In the case in which the carboxy-group-containing resin is blended in the composition and then the composition is cured in a position selective manner, development can be carried out with the use of an alkaline developing solution. In addition, in the case in which the carboxy-group-containing resin is blended in the composition, adhesion of a cured article derived from the composition to the base material can be improved.

Suitable examples of the carboxy-group-containing resin include copolymers of the unsaturated carboxylic acid described above with a monomer that has neither an epoxy group nor an carboxy group, such as an alicyclic-group-containing unsaturated compound with no epoxy group, a (meth)acrylic acid ester, a (meth)acrylamide, an allyl compound, a vinyl ether, a vinyl ester, and a styrene.

As the carboxy-group-containing resin, carboxy-group-containing urethane resins obtained by polyaddition of a diisocyanate such as an aliphatic diisocyanate, a branched aliphatic diisocyanate, an alicyclic diisocyanate, and an aromatic diisocyanate, a carboxy-group-containing dialcohol compound such as dimethylol propionic acid and dimethylol butanoic acid, and a diol compound such as a polycarbonate type polyol, a polyether type polyol, a polyester type polyol, a polyolefin type polyol, an acryl type polyol, and a bisphenol A type alkylene oxide adduct diol are also preferably used.

A urethane resin is generally a flexible material. Therefore, by blending a carboxy-group-containing urethane resin with the composition, a cured article derived from the composition may have flexibility.

(Metal Phosphinate)

In the case in which the composition contains the (C) thermosetting or photocurable base material, the composition may contain a metal phosphinate for enhancing flame retardancy of the cured article. The metal phosphinate is preferably an organic phosphinate in which two organic groups are bonded to a phosphorus atom. The organic groups that are bonded to a phosphorus atom is preferably an alkyl group having 1 to 6 carbon atoms and an aryl group having 6 to 12 carbon atoms. The metal phosphinate is preferably calcium phosphinate, aluminum phosphinate, or calcium phosphinate.

Examples of commercially available products of the metal phosphinate include EXOLIT OP 1230, EXOLIT OP 930, and EXOLIT OP 935 manufactured by Clariant.

By uniformly mixing the components described above at a predetermined ratio, the composition is obtained.

<<Method for Forming Cured Article>>

In the case in which the composition contains the (C) thermosetting or photocurable base material, a cured article may be formed by shaping the composition into a predetermined shape and then subjecting the shaped composition to heating or light exposure.

Typically, the composition is applied to the surface of the base material and shaped into a film. Examples of a suitable method for applying the composition to the surface of the base material include a dip coating method, a flow coating method, a roll coating method, a bar coating method, a screen printing method, and a curtain coating method. After the composition is applied to the surface of the base material by such a method, in the case in which the component (S) is contained, the coating film is heated as needed at a temperature of 60 to 100° C. (preferably 60 to 95° C.).

The base material is not particularly limited and selected as appropriate depending on the type of the (B) fine particle and the (C) base material contained in the composition and the intended use of the composition. Examples of the base material include printed wiring boards and flexible printed wiring boards with a circuit formed thereon in advance, paper phenol, paper/(phenolic resin), paper/(epoxy resin), (glass cloth)/(epoxy resin), (nonwoven glass fabric)/(epoxy resin), (synthetic fiber)/(epoxy resin), (glass cloth)/(polyimide resin), (glass cloth)/(epoxy-modified polyimide resin), (glass cloth)/bismaleimide/triazine/(epoxy resin), (glass cloth)/(fluorine type resin), (glass cloth)/PPO (polyphenylene oxide), (glass cloth)/PPE (polyphenylene ether), copper-clad laminates, polyimide films, PET films, glass substrates, ceramic substrates, and various wafers.

In the case in which the composition is a composition that contains a combination of a polymerizable compound containing an unsaturated double bond such as the (C) photocurable base material and the (D1) photopolymerization initiator or a composition that contains a combination of an epoxy compound or an oxetane compound and the (D2) acid generator that generates an acid by the action of light, light exposure is carried out for curing the curable composition. Light exposure is carried out, for example, by the use of a conveyor-type photo-curing device that emits an active energy ray. Light exposure to the coating film derived from the composition may also be carried out in a position selectively manner by a method such as light exposure via a photomask or light exposure with the use of a laser direct light exposure device. The light exposure dose is selected as appropriate in consideration of the composition of the composition.

The light exposure device that is used for irradiating the composition with an active energy ray may be a device that is equipped with a high-pressure mercury lamp, an ultra-high-pressure mercury lamp, a metal halide lamp, a mercury short arc lamp, or the like and is capable of emitting ultraviolet light with a wavelength within the range from 350 to 450 nm. The light exposure dose varies depending on the thickness of the composition but typically, it is preferably 20 to 2000 mJ/cm$^2$, preferably 20 to 1500 mJ/cm$^2$.

In the case in which the composition is a composition that contains a combination of an epoxy compound or an oxetane compound and the (D3) curing agent, a composition that contains a self-curing polymer containing a carboxy group and an epoxy group, or a composition that contains a precursor resin such as polyamic acid or other polyimide resins or a polybenzoxazole resin, heating is carried out for curing the composition. The temperature at which the heating is carried out is not particularly limited provided that the temperature achieves thorough curing of the curable composition and the curable composition does not undergo thermal degradation or the like, but is preferably 100 to 180° C., more preferably 120 to 180° C. In the case in which the composition contains a curing agent, it is easy to cure the composition at a temperature within the range from 100 to 180° C. The upper limit to the curing temperature is not limited to 180° C. The curing temperature is preferably 180° C. or less because in this case, only a small amount of energy is consumed for heating for curing and the cured article tends not to undergo thermal degradation, for example.

In the case in which the composition contains the (C) thermosetting base material and the (C) photocurable base material in combination, the curable composition may be subjected to both of light exposure and heating.

In the case in which the composition contains an alkali-soluble component such as a carboxy-group-containing resin and the composition is exposed to light in a position selective manner, the curable composition after light exposure is subjected to development in a well-known alkaline developing solution such as an aqueous sodium carbonate solution at a concentration of 0.3 to 3% by mass. Other alkaline developing solutions that may be used are aqueous solutions of, for example, basic nitrogen-containing compounds such as sodium hydroxide, potassium hydroxide, potassium carbonate, sodium phosphate, sodium silicate, and ammonia. Examples of the method for development include a dipping method, a shower method, a spraying method, and a brush method.

The cured article described above is formed by using the composition that contains the (B) fine particle dispersed by the action of the component (A) without aggregating, and therefore the cured article is uniform. The cured article is suitably used in various purposes depending on the type of the (B) fine particle and the type of the (C) base material.

EXAMPLES

The present invention will be described in more detail by way of Examples. The present invention is not limited to the scope of Examples.

Examples 1 to 25 and Comparative Examples 1 to 9

In Examples, A1 and A2 obtained in the following Preparation Examples 1 and 2 were used as the (A) imidazole compound (component (A)). In Comparative Examples, the following A'1 and A'2 were used as a nitrogen-containing compound (component (A')) similar to the (A) imidazole compound.
A'1: 1-Methylimidazole
A'2: N,N-Dimethyl-N'-phenylurea Preparation Example 1

In Preparation Example 1, an imidazole compound (A1) having the following structure was synthesized.

[Chem. 53]

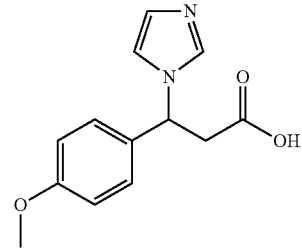

First, 30 g of a cinnamic acid derivative having a structure represented by the following formula was dissolved in 200 g of methanol, and then 7 g of potassium hydroxide was added in the methanol. Next, the methanol solution was stirred at 40° C. Methanol was distilled off and the residue was suspended in 200 g of water. In the suspension thus obtained, 200 g of tetrahydrofuran was mixed, followed by stirring and further separation of the aqueous phase. Under ice cooling, 4 g of hydrochloric acid was added. After stirring, 100 g of ethyl acetate was mixed, followed by stirring. After the mixed solution was left to stand, the oil phase was isolated. The object was crystallized from the oil phase and the precipitate was recovered to obtain an imidazole compound (A1) having the above-mentioned structure.

[Chem. 54]

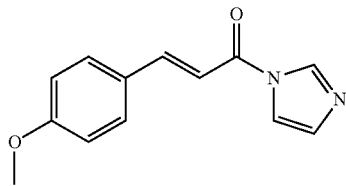

The results of the measurement of $^1$H-NMR of the imidazole compound (A1) are as follows.

$^1$H-NMR (DMSO): 11.724 (s, 1H), 7.838 (s, 1H), 7.340 (d, 2H, J=4.3 Hz), 7.321 (d, 1H, J=7.2 Hz), 6.893 (d, 2H, J=4.3 Hz), 6.876 (d, 1H, J=6.1 Hz), 5.695 (dd, 1H, J=4.3 J, 3.2 J), 3.720 (s, 3H), 3.250 (m, 2H)

Preparation Example 2

In Preparation Example 2, an imidazole compound (A2) having a structure represented by the following formula was synthesized.

[Chem. 55]

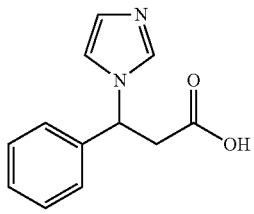

More specifically, the imidazole compound (A2) having the above structure was obtained in the same manner as in Preparation Example 1 except that the raw material compound was a cinnamic acid derivative having a structure represented by the following formula.

[Chem. 56]

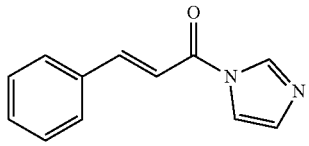

In Examples and Comparative Examples, the following B1 to B10 were used as the (B) fine particle (component (B)).

B1: Titanium oxide (rutile-type, with a volume average particle diameter of 50 nm)

B2: Titanium oxide (rutile-type, with a volume average particle diameter of 700 nm)

B3: Titanium oxide (rutile-type, with a volume average particle diameter of 3500 nm)

B4: Titanium oxide (anatase-type, with a volume average particle diameter of 50 nm)

B5: Barium sulfate (with a volume average particle diameter of 50 nm)

B6: Inorganic black color pigment (with a volume average particle diameter of 50 nm)

B7: $CeO_2$: (with a volume average particle diameter of 50 nm)

B8: $La_2O_3$: (with a volume average particle diameter of 50 nm)

B9: Carbon black: (with a volume average particle diameter of 50 nm)

B10: Carbon black: (with a volume average particle diameter of 700 nm)

B11: Carbon black: (with a volume average particle diameter of 3500 nm)

B12: Styrene-(methyl methacrylate) copolymer fine particle: (with a volume average particle diameter of 50 nm)

B13: Styrene-(methyl methacrylate) copolymer fine particle: (with a volume average particle diameter of 700 nm)

B14: Styrene-(methyl methacrylate) copolymer fine particle: (with a volume average particle diameter of 3500 nm)

In Examples and Comparative Examples, thermosetting base materials C1 to C9 having the following structure and the following C10 and C11 were used as the (C) base material (component (C)). In the following formulae C1 to C4, the numerical value at the bottom right of each constituent unit shows the content (% by mass) of the constituent unit in the resin.

C10: Polyamic acid obtained by reaction of 3,3',4,4'-biphenyltetracarboxylic dianhydride with phenylenediamine at a molar ratio of 1:1

C11: Polybenzoxazole resin precursor obtained by reaction of terephthaloyl dichloride with 4,4'-diamino-3,3'-dihydroxybiphenyl at a molar ratio of 1:1

[Chem. 57]

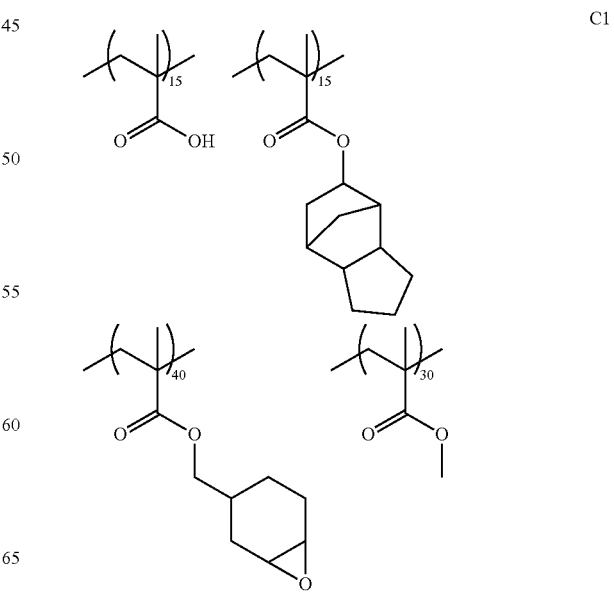

-continued

C2

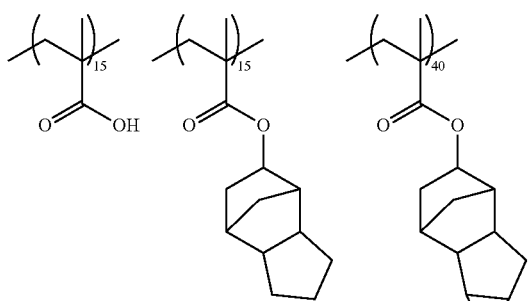

C3

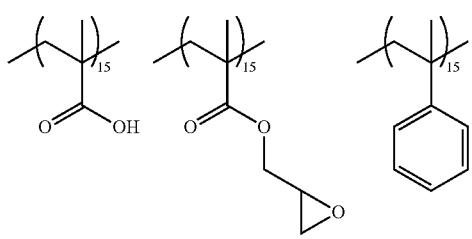

C4

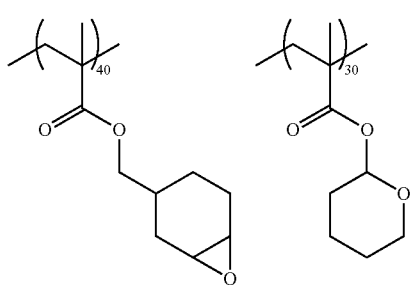

C5

-continued

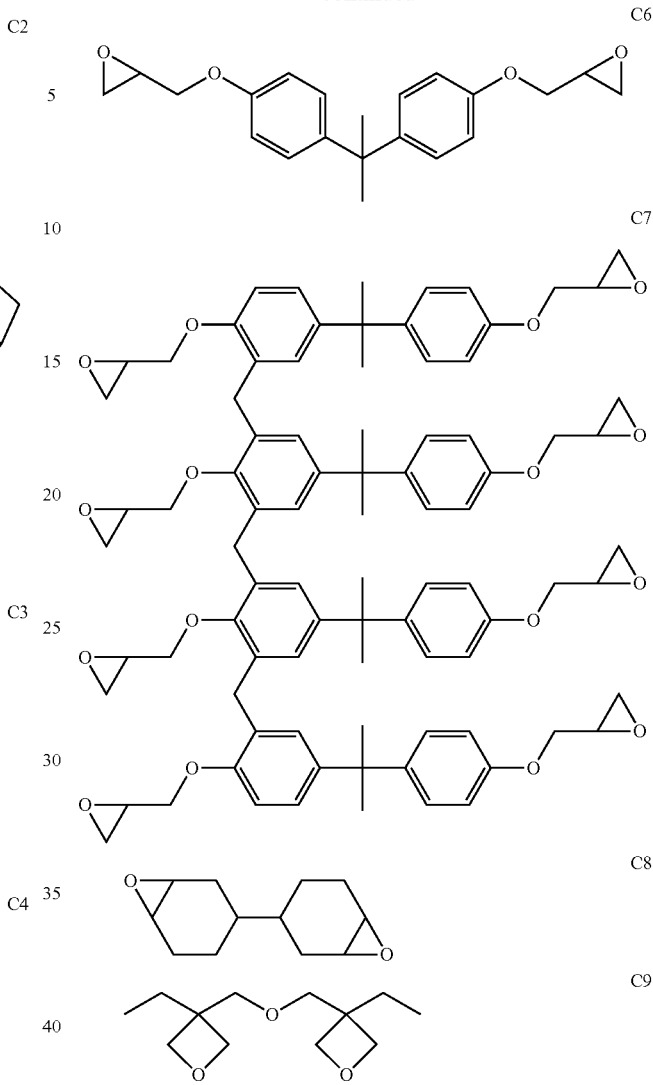

In Examples and Comparative Examples, the following D1 (dicyandiamide) was used as a curing agent.

A component (A) or (A'), a component (B), a component (C), and a component (D) of a type and in an amount specified in Table 1 were mixed (dissolved and/or dispersed) to obtain a composition of each Example or Comparative Example. In the case in which any of the resins C1 to C4 was used as the (C) base material, propylene glycol monomethyl ether acetate was used as a solvent (E) so as to adjust the solid content concentration to 25% by mass. The resulting composition was evaluated by the following methods for storage stability and curing properties. Examples 6, 11 to 13, 15, and 16 and Comparative Examples 4 and 5 were also evaluated for tensile elongation of the cured article.

<Evaluation of Storage Stability>

The composition of each Example or Comparative Example was left still standing at room temperature for 7 days, followed by visual examination of the composition. A composition with precipitation observed was evaluated as Good. A composition with no precipitation observed was evaluated as Poor.

<Curing Properties at Low Temperature>

Two molds were prepared. A curable composition was injected into one of the molds, and the other mold was put on them. In an Example in which any of the resins C1 to C4 was used as the (C) base material, the other mold was put after prebaking was carried out at 90° C. for 2 minutes. Then, the curable composition injected into the mold was heated for 5 minutes at a temperature specified in Table 1, followed by removing the molds. Thus, a plate-like specimen with a thickness of 2 mm was obtained. Successful curing was confirmed when the surface of the specimen was not sticky, namely when the surface of the specimen was tack-free (a specimen that was cured was evaluated as Good, and a specimen that was not cured was evaluated as Poor).

<Tensile Elongation>

The composition of each of Examples 6, 11 to 13, 15, and 16 and Comparative Examples 4 and 5 was applied to a wafer substrate with an applicator (manufactured by YOSHIMITSU SEIKI, model TBA-7). The resulting coating film on the wafer substrate was heated at 160° C. for 5 minutes to obtain a cured film with a film thickness of about 10 μm. The resulting cured film was cut into a dumbbell-shaped specimen the shape of which is specified by IEC450. The specimen was to be used as a specimen for tensile elongation measurement. The resulting specimen was subjected to measurement of elongation at break of the cured article with a universal testing machine (TENSILON manufactured by ORIENTEC Co., Ltd.) under conditions of a chuck-to-chuck distance of 20 mm and a strain rate of 2 mm/minute. The values of elongation at break are shown in Table 1.

TABLE 1

| | Component (type/(parts by mass)) | | | | Storage | Curing properties | | | Tensile |
| | (A) or (A') | (B) | (C) | (D) | stability | 120° C. | 140° C. | 160° C. | elongation (%) |
|---|---|---|---|---|---|---|---|---|---|
| Example 1 | A1/2 | B1/40 | C1/100 | D1/5 | Good | Good | Good | Good | — |
| Example 2 | A1/2 | B1/40 | C2/100 | D1/5 | Good | Good | Good | Good | — |
| Example 3 | A1/2 | B1/40 | C3/100 | D1/5 | Good | Good | Good | Good | — |
| Example 4 | A1/2 | B1/40 | C4/100 | D1/5 | Good | Good | Good | Good | — |
| Example 5 | A1/2 | B1/40 | C5/100 | D1/5 | Good | Good | Good | Good | — |
| Example 6 | A1/2 | B1/40 | C6/100 | D1/5 | Good | Good | Good | Good | 5 |
| Example 7 | A1/2 | B1/40 | C7/100 | D1/5 | Good | Good | Good | Good | — |
| Example 8 | A1/2 | B1/40 | C8/100 | D1/5 | Good | Good | Good | Good | — |
| Example 9 | A1/2 | B1/40 | C5/80 C9/20 | D1/5 | Good | Good | Good | Good | — |
| Example 10 | A1/2 | B1/40 | C6/100 | —/0 | Good | Good | Good | Good | — |
| Example 11 | A1/2 | B1/40 | C10/100 | D1/5 | Good | Good | Good | Good | 10 |
| Example 12 | A1/2 | B1/40 | C11/100 | D1/5 | Good | Good | Good | Good | 10 |
| Example 13 | A1/2 | B2/40 | C11/100 | D1/5 | Good | Good | Good | Good | 5 |
| Example 14 | A2/2 | B1/40 | C6/100 | D1/5 | Good | Good | Good | Good | — |
| Example 15 | A1/2 | B9/40 | C10/100 | D1/5 | Good | Good | Good | Good | 10 |
| Example 16 | A1/2 | B9/40 | C11/100 | D1/5 | Good | Good | Good | Good | 10 |
| Example 17 | A1/2 | B10/40 | C11/100 | D1/5 | Good | Good | Good | Good | — |
| Example 18 | A1/2 | B13/40 | C11/100 | D1/5 | Good | Good | Good | Good | — |
| Example 19 | A1/2 | B5/40 | C6/100 | D1/5 | Good | Good | Good | Good | — |
| Example 20 | A1/2 | B6/40 | C6/100 | D1/5 | Good | Good | Good | Good | — |
| Example 21 | A1/2 | B7/40 | C6/100 | D1/5 | Good | Good | Good | Good | — |
| Example 22 | A1/2 | B8/40 | C6/100 | D1/5 | Good | Good | Good | Good | — |
| Example 23 | A1/2 | B9/40 | C6/100 | D1/5 | Good | Good | Good | Good | — |
| Example 24 | A1/2 | B12/40 | C6/100 | D1/5 | Good | Good | Good | Good | — |
| Example 25 | A1/2 | B13/40 | C6/100 | D1/5 | Good | Good | Good | Good | — |
| Comparative Example 1 | A'1/2 | B1/40 | C6/100 | D1/5 | Poor | Poor | Good | Good | — |
| Comparative Example 2 | A'2/2 | B1/40 | C6/100 | D1/5 | Poor | Poor | Good | Good | — |
| Comparative Example 3 | A1/2 | B3/40 | C6/100 | D1/5 | Poor | Good | Good | Good | — |
| Comparative Example 4 | —/0 | B1/40 | C11/100 | D1/5 | Poor | Poor | Poor | Good | 1 |
| Comparative Example 5 | —/0 | B1/40 | C6/100 | D1/5 | Poor | Poor | Poor | Good | 1 |
| Comparative Example 6 | —/0 | B9/40 | C6/100 | D1/5 | Poor | Poor | Poor | Good | — |
| Comparative Example 7 | —/0 | B12/40 | C6/100 | D1/5 | Poor | Poor | Poor | Good | — |
| Comparative Example 8 | A1/2 | B11/40 | C6/100 | D1/5 | Poor | Good | Good | Good | — |
| Comparative Example 9 | A1/2 | B14/40 | C6/100 | D1/5 | Poor | Good | Good | Good | — |

Table 1 shows the following findings. According to Examples, in a composition containing a combination of the component (A) with a predetermined structure and the (B) fine particle with a volume average particle diameter of 3000 nm or less, aggregation of the (B) fine particle is inhibited.

According to Examples, in a composition containing a combination of the component (A) with a predetermined structure, the (B) fine particle with a volume average particle diameter of 3000 nm or less, and the (C) thermosetting base material, aggregation of the (B) fine particle is inhibited and the composition is cured at low temperature. According to Examples, even in a composition containing a nitrogen-containing compound, if the structure of the nitrogen-containing compound is different from the structure of the component (A), aggregation of the (B) fine particle cannot be inhibited and the temperature required for thermosetting the component (C) is slightly high.

According to Comparative Examples 4 to 7, in a composition containing no nitrogen-containing compound, aggregation of the (B) fine particle cannot be inhibited and the temperature required for thermosetting the component (C) is high.

According to Comparative Examples 3, 8, and 9, in a composition in which the volume average particle diameter of the component (B) is higher than 3000 nm, aggregation of the (B) fine particle tends not to be inhibited even by the action of the component (A).

From comparison between the compositions of Examples 6, 11 to 13, 15, and 16 and the compositions of Comparative Examples 4 and 5, a cured article has excellent tensile elongation when it is obtained by thermosetting a composition containing the component (A) and the (C) thermosetting base material.

The invention claimed is:

1. A composition comprising an (A) imidazole compound represented by the following formula (1) and a (B) fine particle, wherein the (B) fine particle has a volume average particle diameter of 3000 nm or less,

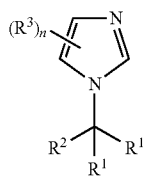

(1)

wherein one $R^1$ is a hydrogen atom and the other $R^1$ is an optionally substituted alkyl group or an optionally substituted aromatic group; $R^2$ represents an optionally substituted aromatic group; each $R^3$ independently represents a halogen atom, a hydroxy group, a mercapto group, a sulfide group, a silyl group, a silanol group, a nitro group, a nitroso group, a sulfonato group, a phosphino group, a phosphinyl group, a phosphonato group, or an organic group; and n is an integer of 0 to 3, and one of the $R^1$ is optionally bonded to the $R^2$ to form a ring structure.

2. The composition according to claim 1, further comprising a (C) thermosetting or photocurable base material.

3. The composition according to claim 1, wherein the (B) fine particle comprises one or more types selected from the group consisting of an inorganic particle and an organic particle.

4. The composition according to claim 2, wherein the (B) fine particle comprises one or more types selected from the group consisting of an inorganic particle and an organic particle.

5. A cured article comprising the composition according to claim 2.

6. A method for producing a cured article, comprising shaping the composition according to claim 2 into a predetermined shape and then subjecting the shaped composition to heating or light exposure to form a cured article.

7. The method according to claim 6, wherein the composition contains the thermosetting base material and the heating is carried out at a temperature within a range of 100 to 180° C.

* * * * *